US 11,192,924 B2

(12) United States Patent
Petronijevic et al.

(10) Patent No.: US 11,192,924 B2
(45) Date of Patent: Dec. 7, 2021

(54) PROCESS FOR MAKING ARYLOMYCIN RING ANALOGS

(71) Applicant: Genentech, Inc., South San Francisco, CA (US)

(72) Inventors: Filip Petronijevic, South San Francisco, CA (US); Ngiap-Kie Lim, South San Francisco, CA (US); Nicholas Wong, South San Francisco, CA (US); Allen Hong, South San Francisco, CA (US); Haiyun Hou, Detroit, MI (US); Xin Linghu, South San Francisco, CA (US); Francis Gosselin, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 16/581,116

(22) Filed: Sep. 24, 2019

(65) Prior Publication Data

US 2020/0255476 A1    Aug. 13, 2020

Related U.S. Application Data

(63) Continuation of application No. PCT/US2018/024351, filed on Mar. 26, 2018.

(60) Provisional application No. 62/477,268, filed on Mar. 27, 2017.

(51) Int. Cl.
*C07K 7/64*     (2006.01)
*C07K 1/06*     (2006.01)

(52) U.S. Cl.
CPC .............. *C07K 7/64* (2013.01); *C07K 1/061* (2013.01)

(58) Field of Classification Search
CPC ........... C07K 7/64; C07K 1/061; A61P 31/04; C07D 245/02
See application file for complete search history.

(56) References Cited

PUBLICATIONS

Seechurn et al, The Journal of Organic Chemistry, 2011,76, 7918-7932 (Year: 2011).*

Dufour et al., Chem. Eur. J., 2010, 16, 10523-10534 (Year: 2010).*
International Search Report and Written Opinion for PCT/US2018/024351, dated Jun. 11, 2018, 10 pages.
International Preliminary Report on Patentability for PCT/US2018/024351, dated Oct. 1, 2019, 8 pages.
Tan et al., "Latent antibiotics and the potential of the arylomycins for broad-spectrum antibacterial activity" Med. Chem. Commun. 3(8):916-925 (2012).
Liu et al., "Synthesis and Characterization of the Arylomycin Lipoglyeopeptide Antibiotics and the Crystallographic Analysis of Their Complex with Signal Peptidase," J. Am. Chem. Soc. 133(44):17869-17877 (2011).
DeAngelis et al., "Generating Active 'L-Pd(0)' via Neutral or Cationic π-Allylpalladium Complexes Featuring Biaryl/Bipyrazolylphosphines: Synthetic, Mechanistic, and Structure-Activity Studies in Challenging Cross-Coupling Reactions," J. Org. Chem. 80(13):6794-6813 (2015).
Roberts et al., "Structural and initial biological analysis of synthetic arylomycin $A_2$," J. Am. Chem. Soc. 129(51):15830-15838 (2007).
Wong et al., "Stereocontrolled Synthesis of Arylomycin-Based Gram-Negative Antibiotic GDC-5338," Org. Lett. 21:9099-9103 (2019).

* cited by examiner

*Primary Examiner* — Sudhakar Katakam
(74) *Attorney, Agent, or Firm* — Andre T Krammer

(57) ABSTRACT

Methods for making an arylomycin ring of formula t or salts or solvates thereof, wherein R, $R^1$, $R^2$, $R^3$, $R^4$, $R^5$, $R^6$, $R^7$, $R^8$, $R^9$, $R^5$, $R^{10}$ and $Pg^1$ are as defined herein.

11 Claims, No Drawings

PROCESS FOR MAKING ARYLOMYCIN RING ANALOGS

CROSS-REFERENCE TO RELATED APPLICATIONS

This application is a continuation of International Application No. PCT/US2018/024351, filed Mar. 26, 2018, which claims benefit of priority to U.S. Provisional Application No. 62/477,268, filed Mar. 27, 2017, each of which is incorporated by reference herein in its entirety for all purposes.

BACKGROUND

Antibiotic resistance is a serious and growing phenomenon in contemporary medicine and has emerged as a major public health concern of the 21st century. Arylomycin-like compounds have been identified as inhibitors of bacterial signal peptidases and show potential for treatment of infection involving gram-positive and gram-negative bacterials strains that are resistant to existing antibiotics. Synthesis of new arylomycin analogs and in particular preparation of the ring portion of arylomycin, is difficult however. There is accordingly a need for new synthetic procedures for arylomycin analogs and the ring portion thereof.

SUMMARY

The disclosure provides methods for making the arylomycin ring and variants thereof, and for making arylomycin analogs from the ring. In on aspect, it is provided a method for making an arylomycin ring of formula o

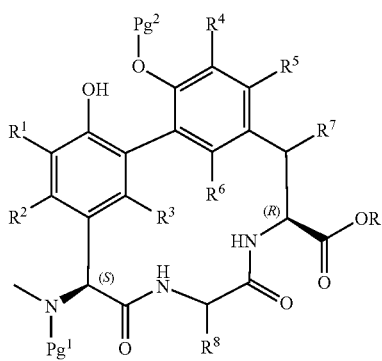

wherein:

Y is halogen;

R is: hydrogen; or $C_{1-4}$alkyl; and may be the same or different on each occurrence, or two R groups may form a $C_{2-6}$alkylene that, together with the atoms to which they are attached, may form a five- or six-membered ring;

$R^1$, $R^2$, $R^3$, $R^4$, $R^5$ and $R^6$ each independently is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; cyano-$C_{1-6}$alkyl; or nitro, wherein the amino and hydroxyl moieties may optionally include a protecting group;

$R^7$ is: hydrogen; or $C_{1-4}$alkyl;

$R^8$ is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; or cyano-$C_{1-6}$alkyl, wherein the amino and hydroxyl moieties may optionally include a protecting group;

$Pg^1$ is an optional amine protecting group; and $Pg^2$ is an optional hydroxyl protecting group;

the method comprising:

reacting a phenyl boronate compound of formula m:

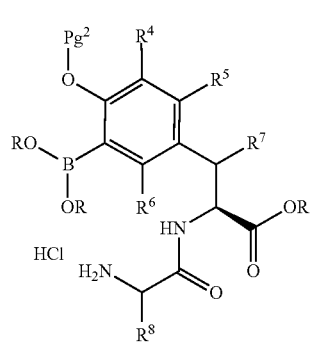

or a salt or solvate thereof, with a phenyl halide compound of formula e;

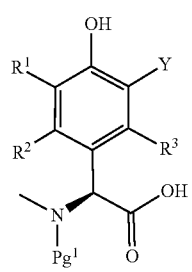

or a salt or solvate thereof, to form a compound of formula n;

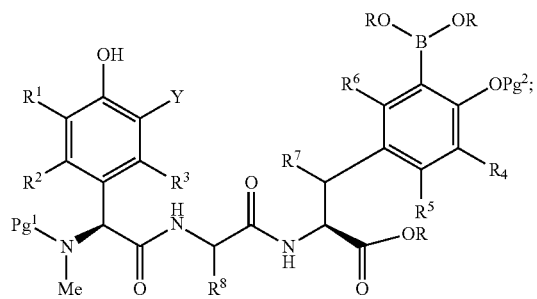

or a salt or solvate thereof; and treating the compound of formula n with chloro(crotyl)(tri-tert-butylphosphine)palladium(II), to make the compound of formula o; or a salt or solvate thereof.

In another embodiment, it is provided a method of making an arylomycin ring of formula o

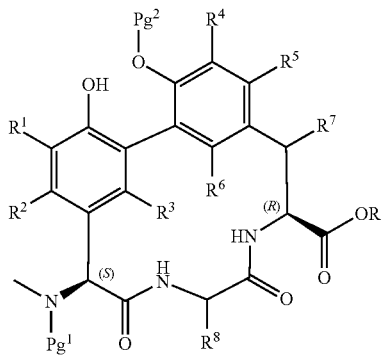

wherein Y, R, $R^1$, $R^2$, $R^3$, $R^4$, $R^5$, $R^6$, $R^7$, $R^8$, $Pg^1$ and $Pg^2$ are as defined herein;

the method comprising:

reacting a phenyl boronate compound of formula m:

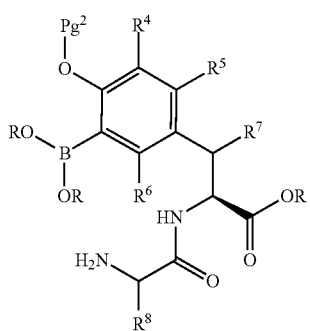

or a salt or solvate thereof, with a phenyl halide compound of formula e;

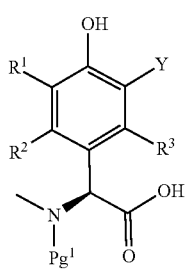

or a salt or solvate thereof, in the presence of chloro(crotyl)(tri-tert-butylphosphine)palladium(II), to form a compound of formula v;

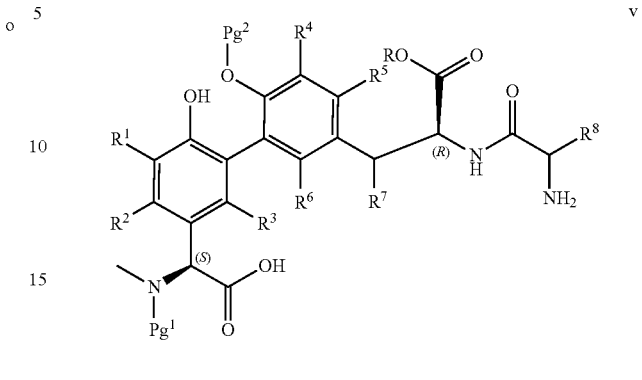

or a salt or solvate thereof; and cyclizing compound v by forming an amide bond to make the compound o; or a salt or solvate thereof.

The subject methods provide unexpectedly better overall yield in producing the ring compound n as well as improved chiral purity via avoidance of potential racemization events. Additional embodiments and details are provided below.

DETAILED DESCRIPTION

Definitions

As used in the specification and the appended claims, the singular forms "a," "an" and "the" include plural referents unless the context clearly dictates otherwise.

The term "about" as used herein, when referring to a numerical value or range, allows for a degree of variability in the value or range, for example, within 10%, or within 5% of a stated value or of a stated limit of a range.

All percent compositions are given as weight-percentages, unless otherwise stated.

All average molecular weights of polymers are weight-average molecular weights, unless otherwise specified.

As used herein:

"Alkyl" means the monovalent linear or branched saturated hydrocarbon moiety, consisting solely of carbon and hydrogen atoms, having from one to twelve carbon atoms. "Lower alkyl" refers to an alkyl group of one to six carbon atoms, i.e. $C_1$-$C_6$alkyl. Examples of alkyl groups include, but are not limited to, methyl, ethyl, propyl, isopropyl, isobutyl, sec-butyl, tert-butyl, pentyl, n-hexyl, octyl, dodecyl, and the like.

"Alkenyl" means a linear monovalent hydrocarbon radical of two to six carbon atoms or a branched monovalent hydrocarbon radical of three to six carbon atoms, containing at least one double bond, e.g., ethenyl, propenyl, and the like.

"Alkynyl" means a linear monovalent hydrocarbon radical of two to six carbon atoms or a branched monovalent hydrocarbon radical of three to six carbon atoms, containing at least one triple bond, e.g., ethynyl, propynyl, and the like.

"Alkylene" means a linear saturated divalent hydrocarbon radical of one to six carbon atoms or a branched saturated divalent hydrocarbon radical of three to six carbon atoms, e.g., methylene, ethylene, 2,2-dimethylethylene, propylene, 2-methylpropylene, butylene, pentylene, and the like.

"Alkoxy" and "alkyloxy", which may be used interchangeably, mean a moiety of the formula —OR, wherein R is an alkyl moiety as defined herein. Examples of alkoxy moieties include, but are not limited to, methoxy, ethoxy, isopropoxy, and the like.

"Alkoxyalkyl" means a moiety of the formula $R^a$—O—$R^b$—, where $R^a$ is alkyl and $R^b$ is alkylene as defined herein. Exemplary alkoxyalkyl groups include, by way of example, 2-methoxyethyl, 3-methoxypropyl, 1-methyl-2-methoxyethyl, 1-(2-methoxyethyl)-3-methoxypropyl, and 1-(2-methoxyethyl)-3-methoxypropyl.

"Alkoxyalkoxy" means a group of the formula —O—R—R' wherein R is alkylene and R' is alkoxy as defined herein.

"Alkylcarbonyl" means a moiety of the formula —C(O)—R, wherein R is alkyl as defined herein.

"Alkoxycarbonyl" means a group of the formula —C(O)—R wherein R is alkoxy as defined herein.

"Alkylcarbonylamino" means a group of the formula —R—C(O)—NR'— wherein R is alkyl and R' is hydrogen or alkyl.

"Alkylcarbonylalkyl" means a group of the formula —R—C(O)—R' wherein R is alkylene and R' is alkyl as defined herein.

"Alkoxyalkylcarbonyl" means a moiety of the formula —C(O)—R—R', wherein R is alkylene and R' is alkoxy as defined herein.

"Alkoxycarbonylalkyl" means a group of the formula —R—C(O)—R' wherein R is alkylene and R' is alkoxy as defined herein.

"Alkoxycarbonylamino" means a moiety of the formula R—C(O)—NR'—, wherein R is alkoxy and R' is hydrogen or alkyl as defined herein.

"Alkoxycarbonylaminoalkyl" means a moiety of the formula R—C(O)—NR'—R"—, wherein R is alkoxy, R' is hydrogen or alkyl, and R" is alkylene as defined herein.

"Alkoxycarbonylalkoxy" means a group of the formula —O—R—C(O)—R' wherein R is alkylene and R' is alkoxy as defined herein.

"Hydroxycarbonylalkoxy" means a group of the formula —O—R—C(O)—OH wherein R is alkylene as defined herein.

"Alkylaminocarbonylalkoxy" means a group of the formula —O—R—C(O)—NHR' wherein R is alkylene and R' is alkyl as defined herein.

"Dialkylaminocarbonylalkoxy" means a group of the formula —O—R—C(O)—NR'R" wherein R is alkylene and R' and R" are alkyl as defined herein.

"Alkylaminoalkoxy" means a group of the formula —O—R—NHR' wherein R is alkylene and R' is alkyl as defined herein.

"Dialkylaminoalkoxy" means a group of the formula —O—R—NR'R" wherein R is alkylene and R' and R" are alkyl as defined herein.

"Alkylsulfonyl" means a moiety of the formula —$SO_2$—R, wherein R is alkyl as defined herein.

"Alkylsulfonylalkyl" means a moiety of the formula —R'—$SO_2$—R" where R' is alkylene and R" is alkyl as defined herein.

"Alkylsulfonylalkoxy" means a group of the formula —O—R—$SO_2$—R' wherein R is alkylene and R' is alkyl as defined herein.

"Amino" means a moiety of the formula —NRR' wherein R and R' each independently is hydrogen or alkyl as defined herein. "Amino" also includes "alkylamino" (where one of R and R' is alkyl and the other is hydrogen) and "dialkylamino" (where R and R' are both alkyl.

"Aminocarbonyl" means a group of the formula —C(O)—R wherein R is amino as defined herein.

"N-hydroxy-aminocarbonyl" means a group of the formula —C(O)—NR—OH wherein R is hydrogen or alkyl as defined herein.

"N-alkoxy-aminocarbonyl" means a group of the formula —C(O)—NR—R' wherein R is hydrogen or alkyl and R' is alkoxy as defined herein.

"Aminocarbonylaminoalkyl" means a group of the formula R2N—C(O)—NR'—R"— wherein each R is independently hydrogen or alkyl, R' is hydrogen or alkyl, and R" is alkylene as defined herein.

"N-alkyl-aminocarbonyl means a group of the formula —C(O)—NH—R wherein R is alkyl as defined herein.

"N-hydroxy-N-alkylaminocarbonyl means a group of the formula —C(O)—NRR' wherein R is alkyl as defined herein and R' is hydroxy.

"N-alkoxy-N-alkylaminocarbonyl" means a group of the formula —C(O)—NRR' wherein R is alkyl and R' is alkoxy as defined herein.

"N,N-di-$C_{1-6}$alkyl-aminocarbonyl" means a group of the formula —C(O)—NRR' wherein R and R' are alkyl as defined herein.

"Aminosulfonyl" means a group of the formula —$SO_2$—$NH_2$.

"N-alkylaminosulfonyl" means a group of the formula —$SO_2$—NHR wherein R is alkyl as defined herein.

"N,N-dialkylaminosulfonyl" means a group of the formula —$SO_2$—NRR' wherein R and R' are alkyl as defined herein.

"Alkylsulfonylamino" means a group of the formula —NR'—$SO_2$—R wherein R id alkyl and R' is hydrogen or alkyl as defined herein.

"N-(alkylsulfonyl)-aminoalkyl" means a group of the formula —R—NH—$SO_2$-R' wherein R is alkylene and R' is alkyl as defined herein.

"N-(Alkylsulfonyl)aminocarbonyl" means a group of the formula —C(O)—NH—$SO_2$—R wherein R is alkyl as defined herein.

"N-(Alkylsulfonyl)-N-alkylaminocarbonyl" means a group of the formula —C(O)—NR—$SO_2$—R' wherein R and R' are alkyl as defined herein.

"N-Alkoxyalkyl-aminocarbonyl" means a group of the formula —C(O)—NR—R'—OR" wherein R is hydrogen or alkyl, R' is alkylene, and R" is alkyl as defined herein.

"N-Hydroxyalkyl-aminocarbonyl" means a group of the formula —C(O)—NR—R'—OH" wherein R is hydrogen or alkyl and R' is alkylene as defined herein.

"Alkoxyamino" means a moiety of the formula —NR—OR' wherein R is hydrogen or alkyl and R' is alkyl as defined herein.

"Alkylsulfanyl" means a moiety of the formula —SR wherein R is alkyl as defined herein.

"Aminoalkyl" means a group —R—R' wherein R' is amino and R is alkylene as defined herein.

"Aminoalkyl" includes aminomethyl, aminoethyl, 1-aminopropyl, 2-aminopropyl, and the like. The amino moiety of "aminoalkyl" may be substituted once or twice with alkyl to provide "alkylaminoalkyl" and "dialkylaminoalkyl" respectively. "Alkylaminoalkyl" includes methylaminomethyl, methylaminoethyl, methylaminopropyl, ethylaminoethyl and the like. "Dialkylaminoalkyl" includes dimethylaminomethyl, dimethylaminoethyl, dimethylaminopropyl, N-methyl-N-ethylaminoethyl, and the like.

"Aminoalkoxy" means a group —OR—R' wherein R' is amino and R is alkylene as defined herein.

"Alkylsulfonylamido" means a moiety of the formula —NR'$SO_2$-R wherein R is alkyl and R' is hydrogen or alkyl.

"Aminocarbonyloxyalkyl" or "carbamylalkyl" means a group of the formula —R—O—C(O)—NR'R" wherein R is alkylene and R', R" each independently is hydrogen or alkyl as defined herein.

"Alkynylalkoxy" means a group of the formula —O—R—R' wherein R is alkylene and R' is alkynyl as defined herein.

"Aryl" means a monovalent cyclic aromatic hydrocarbon moiety consisting of a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, of which may be optionally substituted as defined herein.

"Arylalkyl" and "Aralkyl", which may be used interchangeably, mean a radical-$R^aR^b$ where $R^a$ is an alkylene group and $R^b$ is an aryl group as defined herein; e.g., phenylalkyls such as benzyl, phenylethyl, 3-(3-chlorophenyl)-2-methylpentyl, and the like are examples of arylalkyl.

"Arylsulfonyl" means a group of the formula —$SO_2$—R wherein R is aryl as defined herein.

"Aryloxy" means a group of the formula —O—R wherein R is aryl as defined herein.

"Aralkyloxy" means a group of the formula —O—R—R" wherein R is alkylene and R' is aryl as defined herein.

"Carboxy" or "hydroxycarbonyl", which may be used interchangeably, means a group of the formula —C(O)—OH.

"Cyanoalkyl" means a moiety of the formula —R'—R", where R' is alkylene as defined herein and R" is cyano or nitrile.

"Cycloalkyl" means a monovalent saturated carbocyclic moiety consisting of mono- or bicyclic rings. Particular cycloalkyl are unsubstituted or substituted with alkyl. Cycloalkyl can optionally be substituted as defined herein. Unless defined otherwise, cycloalkyl may be optionally substituted with one or more substituents, wherein each substituent is independently hydroxy, alkyl, alkoxy, halo, haloalkyl, amino, monoalkylamino, or dialkylamino. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

"Cycloalkenyl" means a cycloalkyl as defined herein that includes at least one double bond or unsaturation. Exemplary cycloalkenyl include cyclohexenyl, cyclopentenyl, cyclobutenyl and the like.

"Cycloalkylalkyl" means a moiety of the formula —R'—R", where R' is alkylene and R" is cycloalkyl as defined herein.

"Cycloalkylalkoxy" means a group of the formula —O—R—R' wherein R is alkylene and R' is cycloalkyl as defined herein.

"Cycloalkylcarbonyl" means a moiety of the formula —C(O)—R, wherein R is cycloalkyl as defined herein.

"$C_{3-6}$cycloalkyl-$C_{1-6}$alkyl-carbonyl" means a moiety of the formula —C(O)—R, wherein R is cycloalkylalkyl as defined herein.

"Cyanoalkylcarbonyl" means a moiety of the formula —C(O)—R—R', wherein R is alkylene as defined herein and R' is cyano or nitrile.

"N-Cyano-aminocarbonyl" means a moiety of the formula —C(O)—NHR, wherein R is cyano or nitrile.

"N-Cyano-N-alkyl-aminocarbonyl" means a moiety of the formula —C(O)—NRR'—R, wherein R' is alkyl as defined herein and R is cyano or nitrile.

"Cycloalkylsulfonyl" means a group of the formula —$SO_2$—R wherein R is cycloalkyl as defined herein.

"Cycloalkylalkylsulfonyl" means a group of the formula —$SO_2$—R wherein R is cycloalkylalkyl as defined herein.

"Formyl" means a moiety of the formula —C(O)—H.

"Heteroaryl" means a monocyclic or bicyclic radical of 5 to 12 ring atoms having at least one aromatic ring containing one, two, or three ring heteroatoms selected from N, O, or S, the remaining ring atoms being C, with the understanding that the attachment point of the heteroaryl radical will be on an aromatic ring. The heteroaryl ring may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, each of which may be optionally substituted as defined herein.

"Heteroarylalkyl" or "heteroaralkyl" means a group of the formula -R-R' wherein R is alkylene and R' is heteroaryl as defined herein.

"Heteroarylsulfonyl" means a group of the formula —$SO_2$-R wherein R is heteroaryl as defined herein.

"Heteroaryloxy" means a group of the formula —O—R wherein R is heteroaryl as defined herein.

"Heteroarylcarbonyl" means a group of the formula —C(O)—R wherein R is heteroaryl as defined herein.

"Heteroaralkyloxy" means a group of the formula —O—R—R" wherein R is alkylene and R' is heteroaryl as defined herein.

The terms "halo", "halogen" and "halide", which may be used interchangeably, refer to a substituent fluoro, chloro, bromo, or iodo.

"Haloalkyl" means alkyl as defined herein in which one or more hydrogen has been replaced with same or different halogen. Exemplary haloalkyls include —$CH_2Cl$, —$CH_2CF_3$, —$CH_2CCl_3$, perfluoroalkyl (e.g., —CF3), and the like.

"Haloalkoxy" means a moiety of the formula —OR, wherein R is a haloalkyl moiety as defined herein. An exemplary haloalkoxy is difluoromethoxy.

"Heterocycloamino" means a saturated ring wherein at least one ring atom is N, NH or N-alkyl and the remaining ring atoms form an alkylene group.

"Heterocyclyl" means a monovalent saturated moiety, consisting of one to three rings, incorporating one, two, or three or four heteroatoms (chosen from nitrogen, oxygen or sulfur). The heterocyclyl ring may be optionally substituted as defined herein. Examples of heterocyclyl moieties include, but are not limited to, optionally substituted piperidinyl, piperazinyl, morpholinyl, thiomorpholinyl, azepinyl, pyrrolidinyl, azetidinyl, tetrahydropyranyl, tetrahydrofuranyl, oxetanyl and the like. Such heterocyclyl may be optionally substituted as defined herein.

"Heterocyclylalkyl" means a moiety of the formula —R—R' wherein R is alkylene and R' is heterocyclyl as defined herein.

"Heterocyclyloxy" means a moiety of the formula —OR wherein R is heterocyclyl as defined herein.

"Heterocyclylalkoxy" means a moiety of the formula —OR—R' wherein R is alkylene and R' is heterocyclyl as defined herein.

"Hydroxyalkoxy" means a moiety of the formula —OR wherein R is hydroxyalkyl as defined herein.

"Hydroxyalkylamino" means a moiety of the formula —NR—R' wherein R is hydrogen or alkyl and R' is hydroxyalkyl as defined herein.

"Hydroxyalkylaminoalkyl" means a moiety of the formula —R—NR'—R" wherein R is alkylene, R' is hydrogen or alkyl, and R" is hydroxyalkyl as defined herein.

"Hydroxycarbonylalkyl" or "carboxyalkyl" means a group of the formula —R—(CO)—OH where R is alkylene as defined herein.

"Hydroxycarbonylalkoxy" means a group of the formula —O—R—C(O)—OH wherein R is alkylene as defined herein.

"Hydroxyalkylcarbonyl" means a moiety of the formula —C(O)—R—R', wherein R is alkylene as defined herein and R' is hydroxy.

"Hydroxyalkyloxycarbonylalkyl" or "hydroxyalkoxycarbonylalkyl" means a group of the formula —R—C(O)—O—R—OH wherein each R is alkylene and may be the same or different.

"Hydroxyalkyl" means an alkyl moiety as defined herein, substituted with one or more, for example, one, two or three hydroxy groups, provided that the same carbon atom does not carry more than one hydroxy group. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl, and 2-(hydroxymethyl)-3-hydroxypropyl.

"Hydroxycycloalkyl" means a cycloalkyl moiety as defined herein wherein one, two or three hydrogen atoms in the cycloalkyl radical have been replaced with a hydroxy substituent. Representative examples include, but are not limited to, 2-, 3-, or 4-hydroxycyclohexyl, and the like.

"Oxo" means a group of the formula =O (i.e., an oxygen with a double bond). Thus, for example, a 1-oxo-ethyl group is an acetyl group.

"Alkoxy hydroxyalkyl" and "hydroxy alkoxyalkyl", which may be used interchangeably, means an alkyl as defined herein that is substituted at least once with hydroxy and at least once with alkoxy.

"Alkoxy hydroxyalkyl" and "hydroxy alkoxyalkyl" thus encompass, for example, 2-hydroxy-3-methoxy-propan-1-yl and the like.

"Urea" or "ureido" means a group of the formula —NR'—C(O)—NR"R'" wherein R', R" and R'" each independently is hydrogen or alkyl.

"Carbamate" means a group of the formula —O—C(O)—NR'R" wherein R' and R" each independently is hydrogen or alkyl.

"Carboxy" means a group of the formula —O—C(O)—OH.

"Sulfonamido" means a group of the formula —SO$_2$-NR'R" wherein R', R" and R'" each independently is hydrogen or alkyl.

"Optionally substituted" when used in association with an "aryl", "phenyl", "heteroaryl" "cycloalkyl" or "heterocyclyl" moiety means that such moiety may be unsubstituted (i.e., all open valencies are occupied by a hydrogen atom) or substituted with specific groups as related herein.

"Leaving group" means the group with the meaning conventionally associated with it in synthetic organic chemistry, i.e., an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

"Modulator" means a molecule that interacts with a target. The interactions include, but are not limited to, agonist, antagonist, and the like, as defined herein.

"Optional" or "optionally" means that the subsequently described event or circumstance may but need not occur, and that the description includes instances where the event or circumstance occurs and instances in which it does not.

"Disease" and "Disease state" means any disease, condition, symptom, disorder or indication.

"Inert organic solvent" or "inert solvent" means the solvent is inert under the conditions of the reaction being described in conjunction therewith, including for example, benzene, toluene, acetonitrile, tetrahydrofuran, N,N-dimethylformamide, chloroform, methylene chloride or dichloromethane, dichloroethane, diethyl ether, ethyl acetate, acetone, methyl ethyl ketone, methanol, ethanol, propanol, isopropanol, tent-butanol, dioxane, pyridine, and the like. Unless specified to the contrary, the solvents used in the reactions of some embodiments are inert solvents.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

"Pharmaceutically acceptable salts" of a compound means salts that are pharmaceutically acceptable, as defined herein, and that possess the desired pharmacological activity of the parent compound.

It should be understood that all references to pharmaceutically acceptable salts include solvent addition forms (solvates) or crystal forms (polymorphs) as defined herein, of the same acid addition salt.

"Protective group" or "protecting group" means the group which selectively blocks one reactive site in a multifunctional compound such that a chemical reaction can be carried out selectively at another unprotected reactive site in the meaning conventionally associated with it in synthetic chemistry. Certain processes of some embodiments rely upon the protective groups to block reactive nitrogen and/or oxygen atoms present in the reactants. For example, the terms "amino-protecting group" and "nitrogen protecting group" are used interchangeably herein and refer to those organic groups intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. The artisan in the art will know how to chose a group for the ease of removal and for the ability to withstand the following reactions.

"Solvates" means solvent additions forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H₂O, such combination being able to form one or more hydrate.

"Arthritis" means a disease or condition that causes damage to joints of the body and pain associated with such joint damage. Arthritis includes rheumatoid arthritis, osteoarthritis, psoriatic arthritis, septic arthritis, spondyloarthropathies, gouty arthritis, systemic lupus erythematosus and juvenile arthritis, osteoarthritis, and other arthritic conditions.

"Respiratory disorder" refers to, without limitation, chronic obstructive pulmonary disease (COPD), asthma, bronchospasm, and the like.

"Subject" means mammals and non-mammals. Mammals means any member of the mammalia class including, but not limited to, humans; non-human primates such as chimpanzees and other apes and monkey species; farm animals such as cattle, horses, sheep, goats, and swine; domestic animals such as rabbits, dogs, and cats; laboratory animals including rodents, such as rats, mice, and guinea pigs; and the like. Examples of non-mammals include, but are not limited to, birds, and the like. The term "subject" does not denote a particular age or sex.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The terms "those defined above" and "those defined herein" when referring to a variable incorporates by reference the broad definition of the variable as well as particular definitions, if any.

"Treating" or "treatment" of a disease state includes, inter alia, inhibiting the disease state, i.e., arresting the development of the disease state or its clinical symptoms, and/or relieving the disease state, i.e., causing temporary or permanent regression of the disease state or its clinical symptoms.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

The disclosure provides and methods for making the ring portion of arylomycin, and hence methods for making arylomycin analogs, with unexpectedely improved yields and improved chiral purity. The subject methods utilize the palladium catalyst chloro(crotyl)(tri-tert-butylphosphine)palladium(II), also known as "Pd162", in a Suzuki coupling reaction to make the arylomycin ring in high overall yield. Pd162 has the structure:

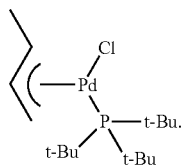

Pd162 is commercially available from Johnson Matthey Fine Chemicals and other sources, and may be prepared according to the procedure reported by DeAnglis et al., J. Org. Chem. Vol. 80, pp 6794-6813 (2015). Use of Pd162-based coupling in accordance with some embodiments results in yields of about 85% in an important step in the formation of the arylomycin ring.

Amide coupling reactions are utilized in many of the synthetic procedures described herein and the reagents involved can be used interchangeably in many instances. Amide coupling as described herein may in many embodiments utilize carbodiimide reagents such as dicyclohexylcarbodiimide (DCC), diisopropylcarbodiimide (DIC) and ethyl-(N',N'-dimethylamino)propylcarbodiimide hydrochloride (EDC or EDCI). 1-Hydroxybenzotriazole (HOBt) or 1-hydroxy-7-azabenzotriazole (HOAt) may be used with carbodiimide based coupling reactions to mimize racemization. In other embodiments additional reagents that may be used for amide coupling, include (Benzotriazol-1-yloxy)tris(dimethylamino)phosphonium hexafluorophosphate (BOP), (Benzotriazol-1-yloxy)tripyrrolidinophosphonium hexafluorophosphate (PyBOP), (7-Azabenzotriazol-1-yloxy)tripyrrolidinophosphonium hexafluorophosphate (PyAOP) and Bromotripyrrolidinophosphonium hexafluorophosphate (PyBrOP). In still other embodiments amide coupling reagents usable include O-(Benzotriazol-1-yl)-N,N,N',N'-tetramethyluronium hexafluorophosphate (HBTU) and O-(Benzotriazol-1-yl)-N,N,N',N'-tetramethyluronium tetrafluoroborate (TBTU), O-(7-azabenzotriazol-1-yl)-N,N,N',N'-tetramethyluronium hexafluorophosphate (HATU), O-(7-Azabenzotriazol-1-yl)-N,N,N',N'-tetramethyluronium tetrafluoroborate (TATU), O-(6-Chlorobenzotriazol-1-yl)-N,N,N',N'-tetramethyluronium hexafluorophosphate (HCTU), O-(N-Suc-cinimidyl)-1,1,3,3-tetramethyl-uronium tetrafluoroborate (TSTU), O-(5-Norbornene-2,3-dicarboximido)-N,N,N',N'-tetramethyluronium tetrafluoroborate (TNTU) and O-(1,2-Dihydro-2-oxo-1-pyridyl-N,N,N',N'-tetramethyluronium tetrafluoroborate (TPTU), 3-(Diethylphosphoryloxy)-1,2,3-benzotriazin-4(3H)-one (DEPBT), isobutyl chloroformate (IBCF), and 6-chloro-2,4-dimethoxy-s-triazine (CDMT). Specific examples disclosed herein utilize some of the above amide coupling reagents, but it should be understood that many of the above amide compiling reagents may alternatively be used.

The subject methods will be more fully understood with reference to the several reaction schemes below, wherein:

R is: hydrogen; or $C_{1-4}$alkyl; and may be the same or different on each occurrence;

$R^1$, $R^2$, $R^3$, $R^4$, $R^5$ and $R^6$ each independently is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; cyano-$C_{1-6}$alkyl; or nitro, wherein the amino and hydroxyl moieties each may optionally include a protecting group;

$R^7$ is: hydrogen; or $C_{1-4}$alkyl;

$R^8$ is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; or cyano-$C_{1-6}$alkyl, wherein the amino and hydroxyl moieties may optionally include a protecting group;

$R^9$ is: $C_{1-4}$alkyl; halo-$C_{1-4}$alky; hydroxyl-$C_{1-4}$alkyl; amino-$C_{1-4}$alkyl, aminosulfonyl-$C_{1-4}$alkyl; or $C_{1-4}$alkoxy-$C_{1-4}$alkyl, wherein the amino and hydroxyl moieties each may optionally include a protecting group;

$R^{10}$ is: hydroxyl-$C_{1-4}$alkyl; amino-$C_{1-4}$alkyl; aminosulfonyl-$C_{1-4}$alkyl; or $C_{1-4}$alkoxy-$C_{1-4}$alkyl, wherein the amino and hydroxyl moieties each may optionally include a protecting group;

$R^a$ is: hydrogen; or $C_{1-4}$alkyl; and may be the same or different on each occurrence, or two R groups may form a $C_{2-6}$alkylene that, together with the atoms to which they are attached, may form a five- or six-membered ring;

X is a leaving group;

Y is halogen (fluoro, chloro, bromo or iodo);

$Pg^1$ is an optional amine protecting group and may be the same or different in each occurrence;

$Pg^2$ is an optional hydroxyl protecting group and may be the same or different in each occurrence;

TG is a "tail group" and is defined further herein; and

WG is a "warhead group" and is defined further herein.

Protecting groups are shown generically in several of the reaction schemes herein, and those skilled in the art will recognize that various different protection and deprotection schemes can in many instances be used alternatively, as described in "Greene's Protective Groups in Organic Synthesis," Fifth Edition, 2014 by John Wiley& Sons, Inc. In some instances amine or hydroxyl substituents may present in the variables $R^1$ through $R^{10}$ described herein, and it should be understood that suitable protecting groups may be utilized in association with such substituents.

Scheme 1A

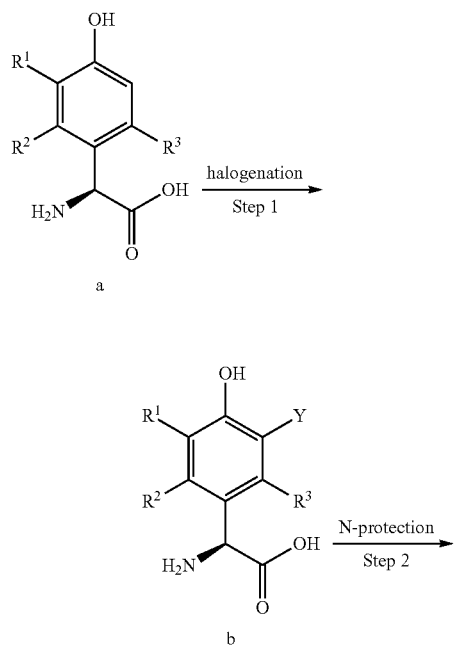

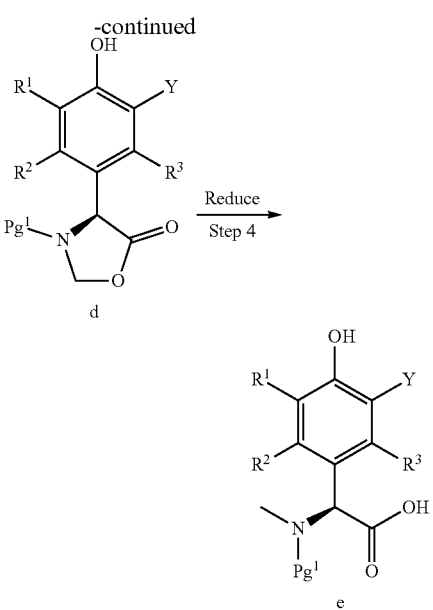

Referring now to Scheme 1A, synthesis of an intermediate halodophenol compound e is shown. In step 1 of Scheme 1A, phenol aminoacid compound a undergoes halogenation to afford halophenol aminoacid compound b. halogenation of step 1 may be carried out using $Fl_2$, $Cl_2$, $Br_2$ or $I_2$ in aqueous ammonia solution at reduced temperature. In many embodiments $I_2$ is used in this step.

In step 2, an amine protecting group may be introduced to provide amine-protected halophenol aminoacid compound c. The protecting groups in many embodiments can be a carboxybenzyl (cbz) group, with the reaction of step 2 achieved using carboxybenzyl chloride with compound b under basic aqueous conditions.

A ring formation is carried out in step 3 by reaction of compound c with trioxane to afford halophenol oxooxazoldine compound d. The reaction of step 3 may occur in polar aprotic solvent such as THF or methyl-THF and in the presence of tosylic acid.

A reduction reaction is then carried out in step 4 to give N-methyl aminoacid intermediate compound e. The reaction of step 4 may be done using a hydrosilane reagent such as triethylsilane under acidic conditions using trifluoroacetic acid in polar aprotic solvent such as dichloromethane. Compound e may then be used as shown below in Scheme 1C or 1D.

Scheme 1B

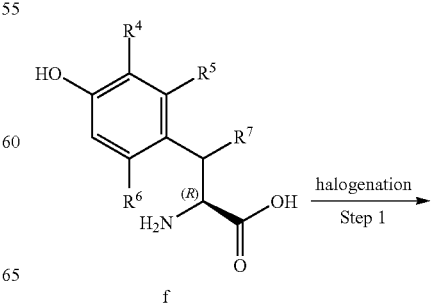

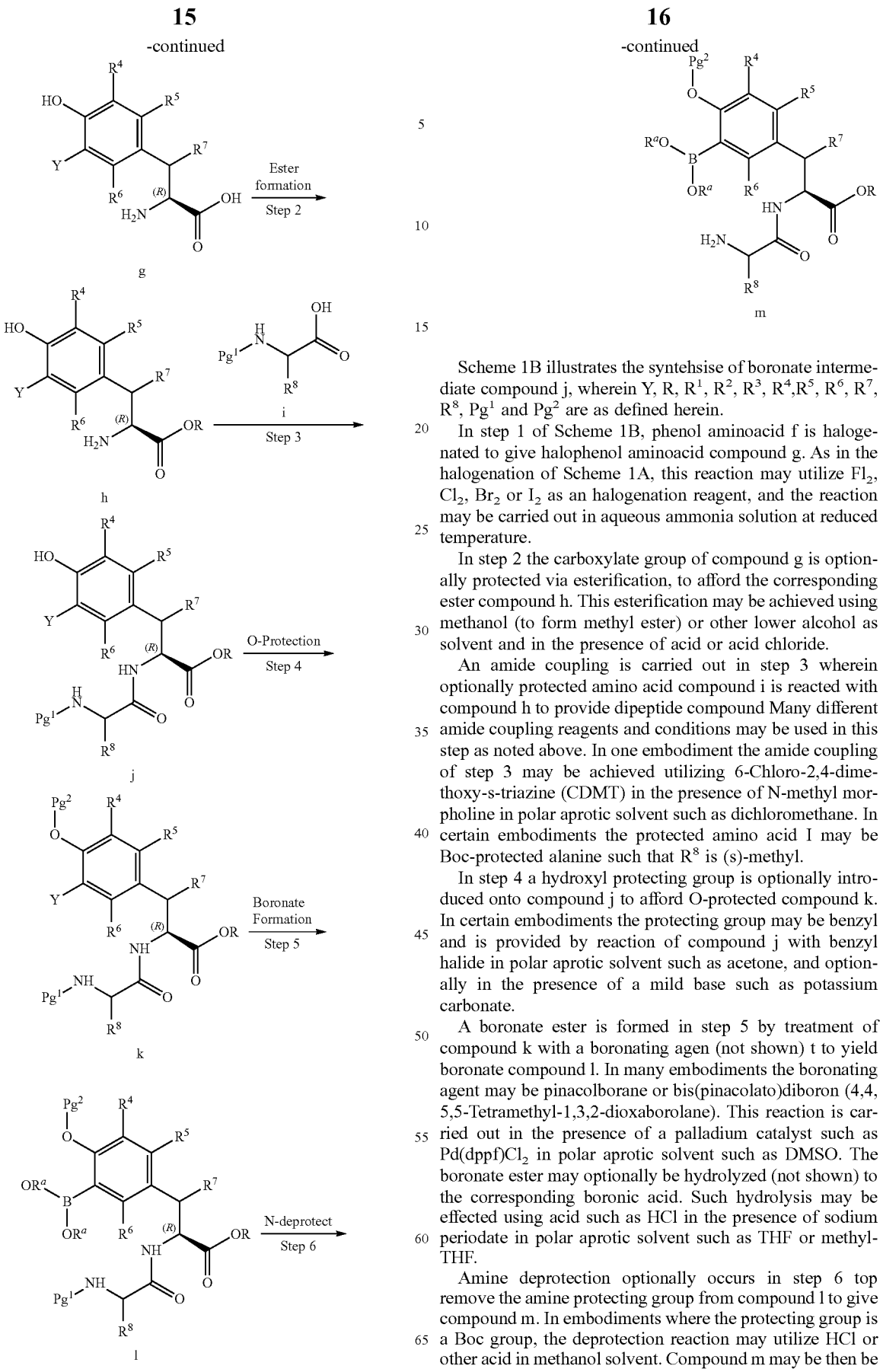

Scheme 1B illustrates the syntehsise of boronate intermediate compound j, wherein Y, R, $R^1$, $R^2$, $R^3$, $R^4$, $R^5$, $R^6$, $R^7$, $R^8$, $Pg^1$ and $Pg^2$ are as defined herein.

In step 1 of Scheme 1B, phenol aminoacid f is halogenated to give halophenol aminoacid compound g. As in the halogenation of Scheme 1A, this reaction may utilize $Fl_2$, $Cl_2$, $Br_2$ or $I_2$ as an halogenation reagent, and the reaction may be carried out in aqueous ammonia solution at reduced temperature.

In step 2 the carboxylate group of compound g is optionally protected via esterification, to afford the corresponding ester compound h. This esterification may be achieved using methanol (to form methyl ester) or other lower alcohol as solvent and in the presence of acid or acid chloride.

An amide coupling is carried out in step 3 wherein optionally protected amino acid compound i is reacted with compound h to provide dipeptide compound Many different amide coupling reagents and conditions may be used in this step as noted above. In one embodiment the amide coupling of step 3 may be achieved utilizing 6-Chloro-2,4-dimethoxy-s-triazine (CDMT) in the presence of N-methyl morpholine in polar aprotic solvent such as dichloromethane. In certain embodiments the protected amino acid I may be Boc-protected alanine such that $R^8$ is (s)-methyl.

In step 4 a hydroxyl protecting group is optionally introduced onto compound j to afford O-protected compound k. In certain embodiments the protecting group may be benzyl and is provided by reaction of compound j with benzyl halide in polar aprotic solvent such as acetone, and optionally in the presence of a mild base such as potassium carbonate.

A boronate ester is formed in step 5 by treatment of compound k with a boronating agen (not shown) t to yield boronate compound l. In many embodiments the boronating agent may be pinacolborane or bis(pinacolato)diboron (4,4,5,5-Tetramethyl-1,3,2-dioxaborolane). This reaction is carried out in the presence of a palladium catalyst such as Pd(dppf)$Cl_2$ in polar aprotic solvent such as DMSO. The boronate ester may optionally be hydrolyzed (not shown) to the corresponding boronic acid. Such hydrolysis may be effected using acid such as HCl in the presence of sodium periodate in polar aprotic solvent such as THF or methyl-THF.

Amine deprotection optionally occurs in step 6 top remove the amine protecting group from compound l to give compound m. In embodiments where the protecting group is a Boc group, the deprotection reaction may utilize HCl or other acid in methanol solvent. Compound m may be then be used as described in Scheme 1C and 1D below.

Scheme 1C

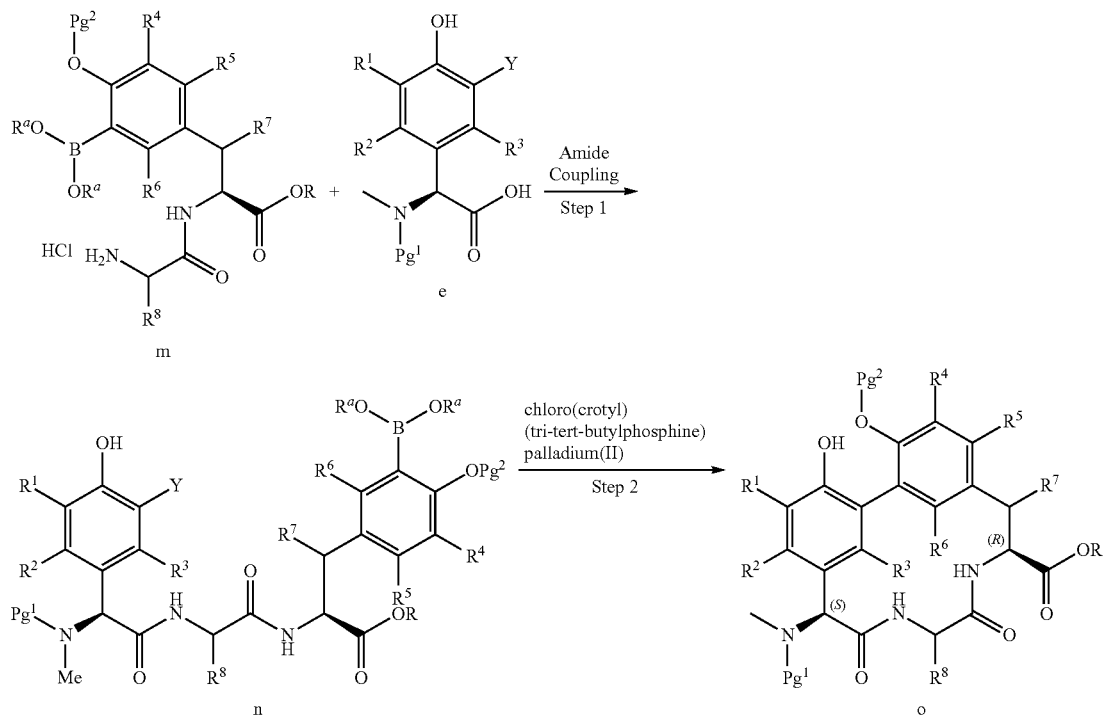

Scheme 1C illustrates the synthesis of arylomycin ring compound o, wherein R, $R^1$, $R^2$, $R^3$, $R^4$, $R^5$, $R^6$, $R^7$, $R^8$, $Pg^1$ and $Pg^2$ are as defined herein.

In step 1 of Scheme 1C, the phenyl halo N-methyl aminoacid compound e is reacted with boronate dipeptide compound m from Scheme 1B, via an amide coupling reaction, to give tripeptide compound n.

Many different amide coupling reagents and conditions may be used in this step, and in one embodiment the reaction is carried out using isobutyl chloroformate (IBCF) in the presence of N-methyl morpholine, in polar aprotic solvent such as DMF, THF, or a mixture thereof.

In step 2, a Suzuki-type coupling reaction is carried out to effect a ring closure in compound n, in the presence of chloro(crotyl)(tri-tert-butylphosphine)palladium(II) ("Pd162"), and thus afford arylomycin ring compound o in accordance with some embodiments. The reaction of step 2 may be done in aqueous acetonitrile and in the presence of mild base such as potassium bicarbonate.

The reaction of step 2 occurs in high yield, and in many embodiments a yield of at least 60-70% under kilogram scale conditions, and in some embodiments 75% is achieved, and certain embodiments at least 80%, and in some embodiments 85%, which are substantially and unexpectedly better yields than has previously been achieved utilizing several different palladium catalysts under different conditions. Previously reported synthetic yields for arylomycin ring formation are substantially lower than are achieved by some embodiments. For example, Dufour et al., *Chem. Eur. J.* 2010, 16, 10523-10534 reported yields ranging from O-54% using multiple different Pd catalysts, and such yields have not been reproducible beyond benchtop scale reactions. Romesburg et al., *J. Am. Chem. Soc.*, 2007. 129, 15830-15838 report yields of only 19-40% utilizing various different Pd catalysts and different solvent conditions and, again, the reported yields are not repeatable in larger scale reactions. Some embodiments also unexpected provide chiral purity of >99% de.

Scheme 1D

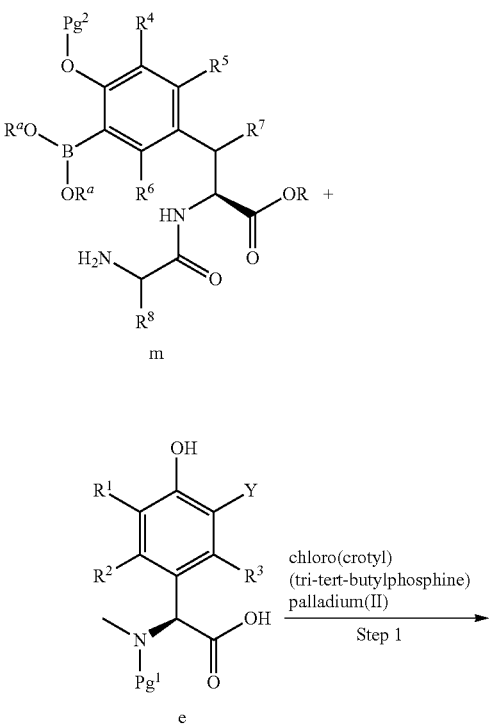

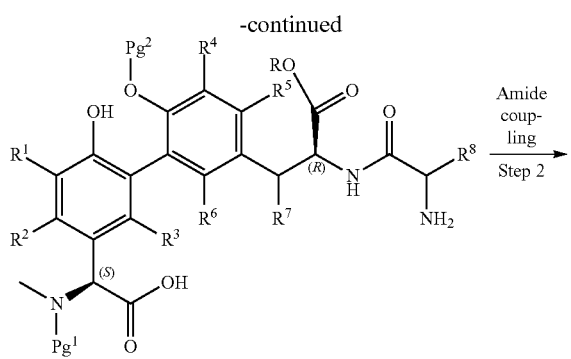

Scheme 1D demonstrates the synthesis of arylomycin ring compound o via an alternate route, wherein Y, R, $R^1$, $R^2$, $R^3$, $R^4$, $R^5$, $R^6$, $R^7$, $R^8$, $Pg^1$ and $Pg^2$ are as defined herein.

In step 1, a Suzuki-type coupling reaction is used with compound m from Scheme 1B and compound e from Scheme 1A, in the presence of chloro(crotyl)(tri-tert-butylphosphine)palladium(II) ("Pd162"), to afford bispehnol compound x. The reaction of step 1 may be carried out in aqueous THF and in the presence of potassium phosphate. This reaction occurs in high yield, and in many embodiments a yield of at least 75% is achieved, and certain embodiments at least 80%, and in some embodiments 85%, which are substantially and unexpectedly better yields than has previously been achieved utilizing several different palladium catalysts under different conditions. For example, Romesburg et al., *J. Am. Chem. Soc.*, 2007. 129, 15830-15838 reports a yield of 36% using PdCl2(dppf) in DMOS. Some embodiments also unexpected provide chiral purity of >99% de.

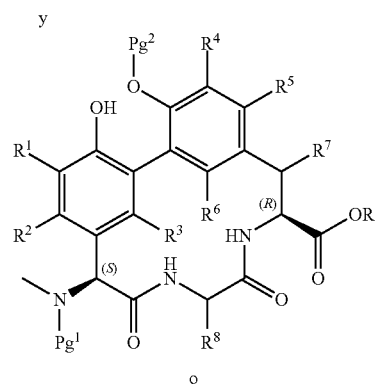

In step 2 compound x undergoes cyclization via amide coupling to afford arylomycin ring compound o in accordance with some embodiments. The amide compling in certain embodiments may be done in the presence of (benzotriazol-1-yloxy)tripyrrolidinophosphonium hexafluorophosphate (PyBOP) and N-methyl morpholine in polar aprotic solvent such as DMF.

Scheme 1E

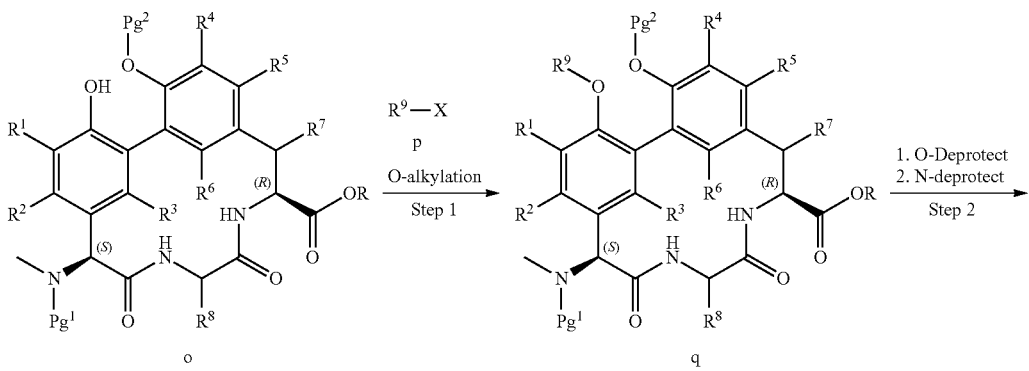

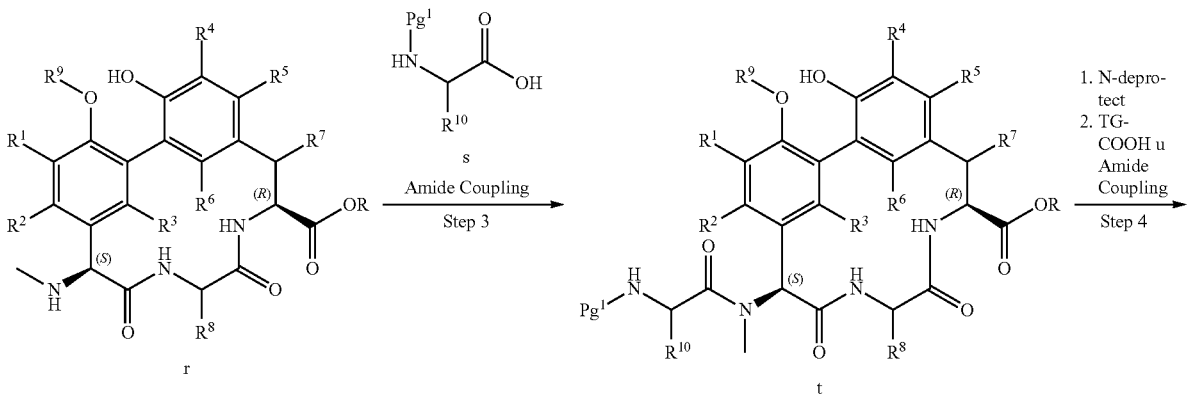

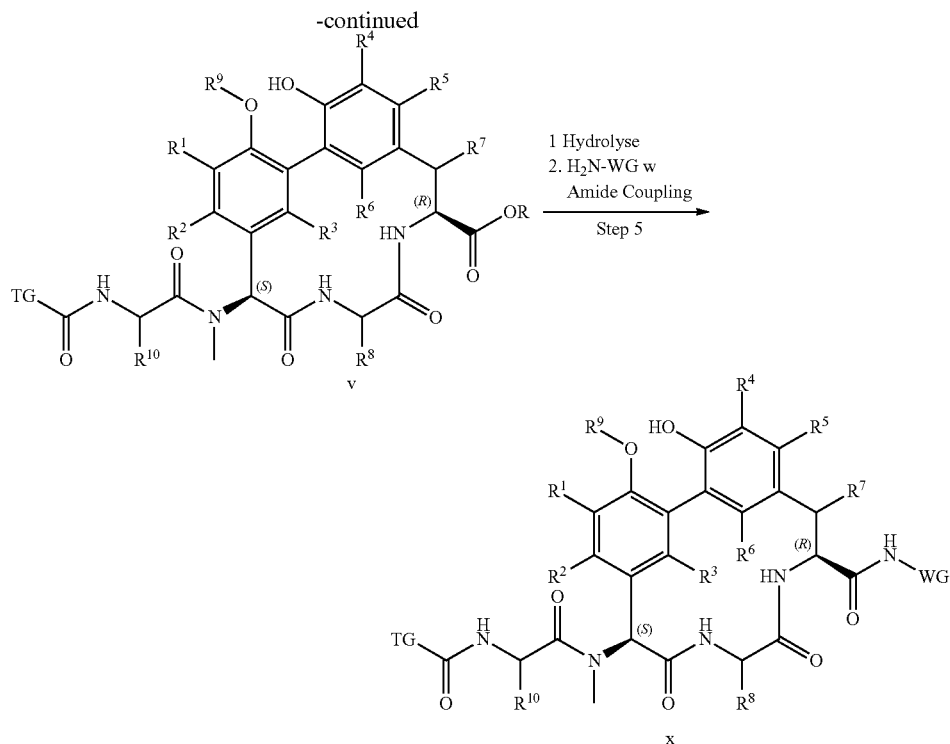

Scheme 1E demonstrates the synthesis of arylomycin analog compounds w from ring compound o, wherein R, $R^1$, $R^2$, $R^3$, $R^4$, $R^5$, $R^6$, $R^7$, $R^8$, $R^9$, $R^{10}$, $Pg^1$ and $Pg^2$ are as defined herein.

In step 1 of Scheme 1E, an optional O-alkylation occurs in which arylomycin ring compound o is treated with alkylating agent p to afford O-alkylated compound q. In certain embodiments reagent p is an amino-$C_{1-4}$alkyl halide wherein the amino includes a protecting group such as Boc. The alkylation reaction may be carried out in dimethylacetamide or other polar aprotic solvent in the presence of potassium phosphate. This step may be omitted such that the phenolic hydroxyl groups of compound o are un-alkylated. Alternatively, protecting group $Pg^2$ may be removed prior to step 1 and both phenolic hydroxyl groups may be reacted with agent p.

In step 2 O-deprotection and/or N-deprotection are optionally carried out to remove groups $Pg^2$ and/or $Pg^1$, to provide compound r. In embodiments wherein $Pg^1$ and $Pg^2$ are carbobenzoxy (Cbz) and benzyl (Bn) respectively, both protecting groups may be removed in a single reaction via reductive debenzylation in the presence of hydrogen gas and Pd/C in dimethylactemide or lake polar aprotic solvent.

In step 3 an amide coupling reaction is carried out by reaction of protected amino acids with compound r to yield compound t. In certain embodiments the amide coupling of step 3 may utilize O-(7-azabenzotriazol-1-yl)-N,N,N',N'-tetramethyluronium hexafluorophosphate (HATU) in the presence of diisopropyl ethylamine (DIPEA) in polar aprotic solvent such as THF or methyl-THF.

In certain embodiments of step 3, amino acid s may be lysine, diaminobutyric acid, or like amino acid wherein $R^{10}$ is an aminoalkyl group (which may be suitably protected). For example, $Pg^1$ of amino acid s may be 9-fluorenyl-methyloxycarbonyl (Fmoc), while $R^{10}$ is —$CH_2$—$CH_2$—NHBoc.

Step 3 may be repeated one or more times to couple additional amino acids s onto compound t. For example, in the preparation of natural arylymycin, step 3 would occur three times: first using glycine, followed by alanine, and last by N-methylserine, to provide the residues found in native arylomycin.

In step 4, the protecting group $Pg^1$ (that was introduced in step 3 on amino acid s) is removed, and amide coupling is carried out by reacting the (deprotected) compound t with "tail group" carboxylate reagent u. In embodiments where $Pg^1$ is an Fmoc group, deprotection may occur using tetrabutylammonium chloride (TBAF) in polar aprotic solvent such as THF or methyl-THF. The amide coupling of step 4 may be effected using ethyl-(N',N'-dimethylamino)propyl-carbodiimide hydrochloride (EDC) in the presence of 1-hydroxy-7-azabenzotriazole (HOAt). Further details for tail group reagent u are provided below.

In step 5, an ester hydrolysis occurs to remove the carboxy protecting group R from compound v, and the resulting carboxylate compound (not shown) is reacted with amine reagent w to introduce a "warhead" group WG and provide compound x. The ester hydrolysis may utilize aqueous lithium hydroxide or other alkalai metal hydroxide in a water miscible polar solvent such as THF. The amide coupling may use O-(7-azabenzotriazol-1-yl)-N,N,N',N'-tetramethyluronium hexafluorophosphate (HATU) in the presence of DIPEA in polar aprotic solvent such as THF or methyl-THF. Further details for warhead group reagent w are provided below.

Many variations on the reactions of Schemes 1A through 1E are possible and will suggest themselves to those skilled in the art. For example, the order of the reactions may be varied in many embodiments. In some instances reaction products need not be isolated but can be used in situ in the following reaction. The amine and hydroxyl protecting group chemistry, as well as the timing of protection and deprotection events, may be varied from the particular embodiments described herein.

The tail group TG is in many embodiments a hydrophobic group or a group including a hydrophobic portion. For example, in natural arylomycin the group TG would be an isoundecyl ($C_{11}$) group, such that reagent u is isododecanoic acid.

In certain embodiments the tail group reagent u may be a carboxy compound of the formula z:

$$R^b \underset{}{-}\underset{(R^c)_m}{\text{phenyl}} \underset{X^2=}{\overset{X^1-}{-}} \underset{(R^d)_n}{\text{phenyl}} -COOH \quad z$$

wherein:
X$^1$ and X$^2$ each independently is N or C;
m and n each independently is 0, 1 or 2;
R$^b$ is:
$C_{1-12}$alkyl which may be unsubstituted or substituted one or more times with halo;
$C_{2-12}$alkenyl which may be unsubstituted or substituted one or more times with halo;
$C_{2-12}$alkynyl which may be unsubstituted or substituted one or more times with halo;
$C_{1-12}$alkoxy which may be unsubstituted or substituted one or more times with halo;
$C_{2-7}$cycloalkyl which may be unsubstituted or substituted one or more times with $C_{1-4}$alkyl, halo-$C_{1-4}$alkyl or halo;
$C_{2-7}$cycloalkyloxy may be unsubstituted or substituted one or more times with $C_{1-4}$alkyl, halo-$C_{1-4}$alkyl or halo;
$C_{1-12}$alkyl-$C_{2-7}$cycloalkyl wherein the cycloalkyl moiety may be unsubstituted or substituted one or more times with $C_{1-4}$alkyl, halo-$C_{1-4}$alkyl or halo;
$C_{2-12}$alkenyl-$C_{2-7}$cycloalkyl wherein the cycloalkyl moiety may be unsubstituted or substituted one or more times with $C_{1-4}$alkyl, halo-$C_{1-4}$alkyl or halo;
$C_{1-12}$alkynyl-$C_{2-7}$cycloalkyl wherein the cycloalkyl moiety may be unsubstituted or substituted one or more times with $C_{1-4}$alkyl, halo-$C_{1-4}$alkyl or halo;
$C_{1-12}$alkyl-$C_{2-7}$cycloalkyloxy wherein the cycloalkyl moiety may be unsubstituted or substituted one or more times with $C_{1-4}$alky, halo-$C_{1-4}$alkyl or halo;
$C_{2-12}$alkenyl-$C_{2-7}$cycloalkyloxy wherein the cycloalkyl moiety may be unsubstituted or substituted one or more times with $C_{1-4}$alkyl, halo-$C_{1-4}$alkyl or halo;
$C_{1-12}$alkynyl-$C_{2-7}$cycloalkyloxy wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkyl wherein the cycloalkyl moiety may be unsubstituted or substituted one or more times with $C_{1-4}$alkyl, halo-$C_{1-4}$alkyl or halo;
$C_{2-7}$cycloalkyl-$C_{2-12}$alkenyl wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkynyl wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkyloxy wherein the cycloalkyl moiety may be unsubstituted or substituted one or more times with $C_{1-4}$alkyl, halo-$C_{1-4}$alkyl or halo;
$C_{2-7}$cycloalkyl-$C_{2-12}$alkenyloxy wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkynyloxy wherein the cycloalkyl moiety may be unsubstituted or substituted one or more times with $C_{1-4}$alkyl, halo-$C_{1-4}$alkyl or halo;
phenyl-$C_{1-12}$alkyl wherein the phenyl moiety may be unsubstituted or substituted one or more times with $C_{1-4}$alkyl, halo-$C_{1-4}$alkyl or halo;
phenyl-$C_{2-12}$alkenyl wherein the phenyl moiety may be unsubstituted or substituted one or more times with $C_{1-4}$alkyl, halo-$C_{1-4}$alkyl or halo;
phenyl-$C_{1-12}$alkynyl wherein the phenyl moiety may be unsubstituted or substituted one or more times with $C_{1-4}$alkyl, halo-$C_{1-4}$alkyl or halo;
phenyl-$C_{1-12}$alkyloxy wherein the phenyl moiety may be unsubstituted or substituted one or more times with $C_{1-4}$alkyl, halo-$C_{1-4}$alkyl or halo;
phenyl-$C_{2-12}$alkenyloxy wherein the phenyl moiety may be unsubstituted or substituted one or more times with $C_{1-4}$alkyl, halo-$C_{1-4}$alkyl or halo; or
phenyl-$C_{1-12}$alkynyloxy wherein the phenol moiety may be unsubstituted or substituted one or more times with $C_{1-4}$alkyl, halo-$C_{1-4}$alkyl or halo; and
R$^c$ and R$^d$ each independently is: $C_{1-4}$alkyl, halo-$C_{1-4}$alkyl or halo.

In certain embodiments the warhead group reagent w may be glycine nitrile ($H_2N$—$CH_2$—$CN$) so that the group WG is —$CH_2CN$. In other embodiments WG may be heteroaryl, amido, epoxy, or other group.

Accordingly, some embodiments provide a method for making an arylomycin ring of formula o o wherein:
Y is halogen (fluoro, chloro, bromo or iodo);
R is: hydrogen; or $C_{1-4}$alkyl; and may be the same or different on each occurrence;
R$^1$, R$^2$, R$^3$, R$^4$, R$^5$ and R$^6$ each independently is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; cyano-$C_{1-6}$alkyl; or nitro, wherein the amino and hydroxyl moieties may optionally include a protecting group;
R$^7$ is: hydrogen; or $C_{1-4}$alkyl;
R$^8$ is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; or cyano-$C_{1-6}$alkyl, wherein the amino and hydroxyl moieties may optionally include a protecting group;
R$^a$ is: hydrogen; or $C_{1-4}$alkyl; and may be the same or different on each occurrence, or two R groups may form a $C_{2-6}$alkylene that, together with the atoms to which they are attached, may form a five- or six-membered ring;

Pg$^1$ is an optional amine protecting group; and

Pg$^2$ is an optional hydroxyl protecting group;

the method comprising:

reacting a phenyl boronate compound of formula m:

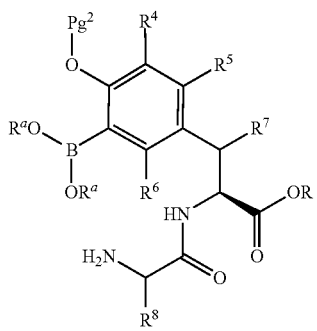

m or a salt or solvate thereof, with a phenyl halide compound of formula e;

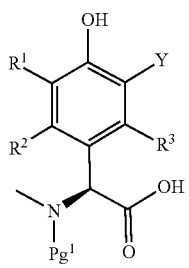

e or a salt or solvate thereof, to form a compound of formula n;

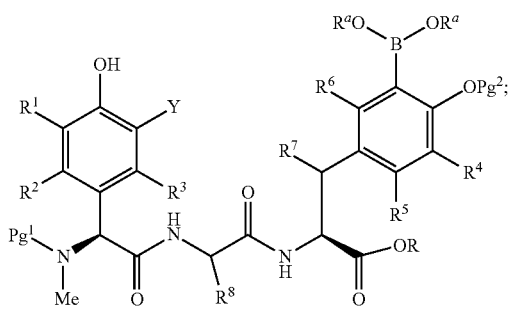

n or a salt or solvate thereof; and treating the compound of formula n with chloro(crotyl)(tri-tert-butylphosphine)palladium(II), to make the compound of formula o; or a salt or solvate thereof.

In another embodiment, it is provided a method of making an arylomycin ring of formula o

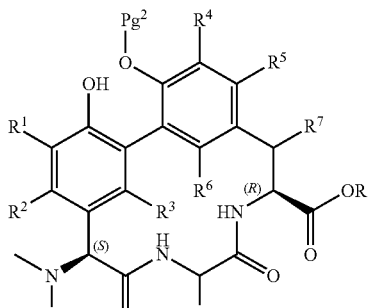

o wherein R, R$^1$, R$^2$, R$^3$, R$^4$, R$^5$, R$^6$, R$^7$, R$^8$, Pg$^1$ and Pg$^2$ are as defined herein;

the method comprising:

reacting a phenyl boronate compound of formula m:

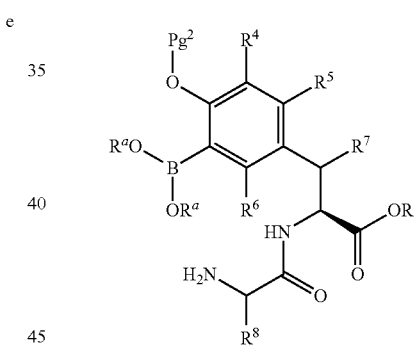

m or a salt or solvate thereof, with a phenyl halide compound of formula e;

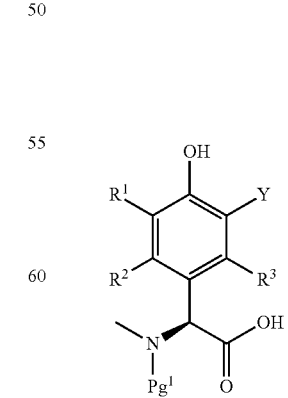

e or a salt or solvate thereof, in the presence of chloro(crotyl)(tri-tert-butylphosphine)palladium(II), to form a compound of formula v;

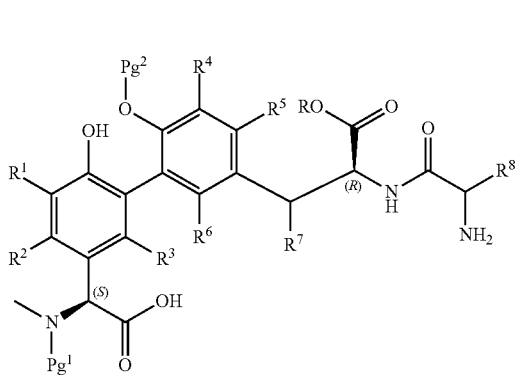

or a salt or solvate thereof; and
cyclizing compound v by forming an amide bond to make the compound o; or a salt or solvate thereof.

In certain embodiments, the subject methods may further comprise:
reacting a compound of formula k

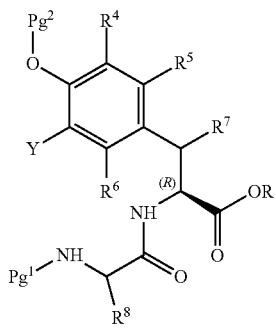

or a salt or solvate thereof,
with a boronating agent to form a compound of formula l

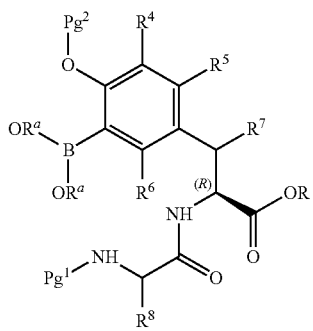

or a salt or solvate thereof; and removing the protecting group $Pg_1$ to form the compound of formula m

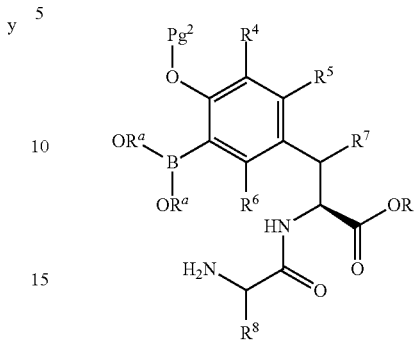

or a salt or solvate thereof,
wherein R, $R^1$, $R^2$, $R^3$, $R^4$, $R^5$, $R^6$, $R^7$, $R^8$, $Pg^1$ and $Pg^2$ are as defined herein.

In certain embodiments, the subject methods may further comprise:
reacting a compound of formula h

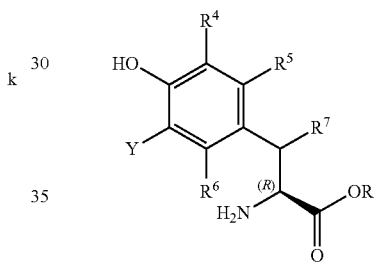

with an amino acid of formula i

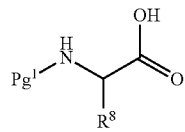

to form a compound of formula j

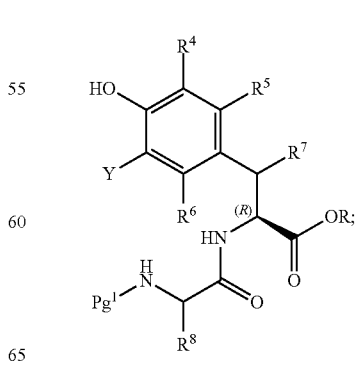

or a salt or solvate thereof; and introducing a hydroxyl protecting group Pg2, to form the compound of formula k

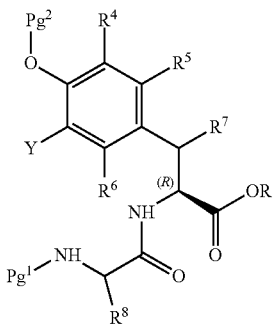

k or a salt or solvate thereof,
wherein Y, R, $R^1$, $R^2$, $R^3$, $R^4$, $R^5$, $R^6$, $R^7$, $R^8$, $Pg^1$ and $Pg^2$ are as defined herein.
In certain embodiments the subject methods may further comprise:
esterifying a compound of formula g

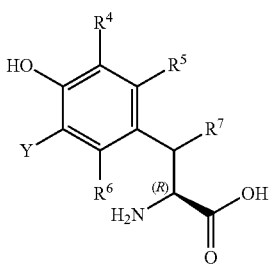

g or a salt or solvate thereof,
to form the compound of formula h

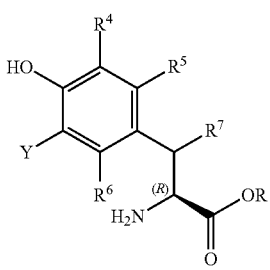

h or a salt or solvate thereof,
wherein Y, R, $R^1$, $R^2$, $R^3$, $R^4$, $R^5$, $R^6$, $R^7$, $Pg^1$ and $Pg^2$ are as defined herein.
In certain embodiments the subject methods may further comprise:

halogenation of a compound formula f

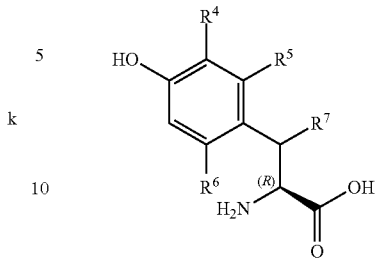

f or a salt or solvate thereof,
to form the compound of formula g

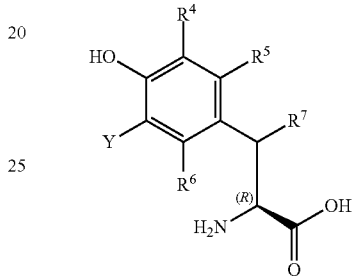

g or a salt or solvate thereof,
wherein Y, R, $R^1$, $R^2$, $R^3$, $R^4$, $R^5$, $R^6$, $R^7$, $Pg^1$ and $Pg^2$ are as defined herein.
In certain embodiments the subject methods may further comprise:
reducing a compound of formula d

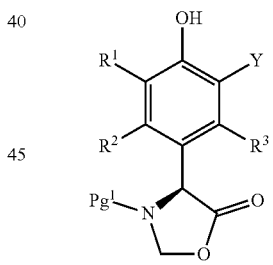

d to form the compound of formula e

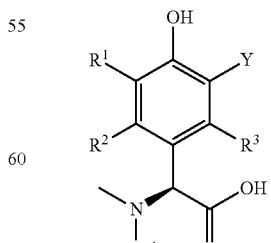

e or a salt or solvate thereof,
wherein Y, R, $R^1$, $R^2$, $R^3$, and $Pg^1$ are as defined herein.

In certain embodiments the subject methods may further comprise:

reacting a compound of formula c

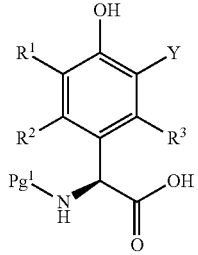

or a salt or solvate thereof,
with trioxane, to form the compound of formula d

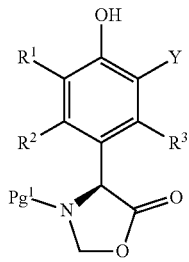

or a salt or solvate thereof,
wherein Y, R, $R^1$, $R^2$, $R^3$, and $Pg^1$ are as defined herein.

In certain embodiments the subject methods may further comprise:

halogenating a compound of formula a

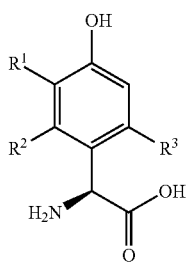

or a salt or solvate thereof,
to form a compound of formula b

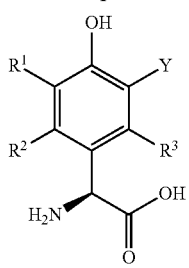

or a salt or solvate thereof; and introducing an amine protecting group to the compound of formula b to form the compound of formula c

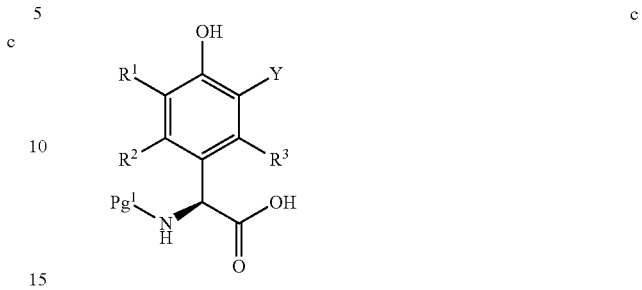

or a salt or solvate thereof;
wherein R, $R^1$, $R^2$, $R^3$, and $Pg^1$ are as defined herein.

In certain embodiments the subject methods may further comprise:

reacting the compound of formula o

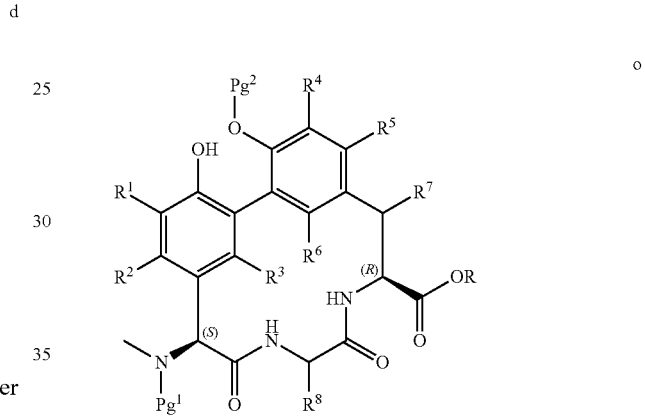

or a salt or solvate thereof;
with an alkylating reagent of formula p $$R^9\text{—}X \qquad p$$

or a salt or solvate thereof,
to form a compound of formula q

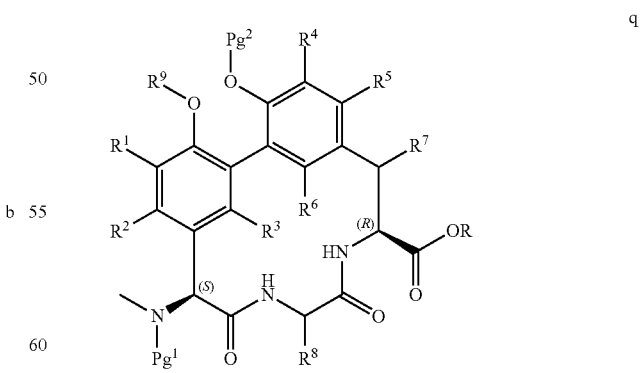

or a salt or solvate thereof;
wherein R, $R^1$, $R^2$, $R^3$, $R^4$, $R^5$, $R^6$, $R^7$, $R^8$, $R^9$, X, $Pg^1$ and $Pg^2$ are as defined herein.

In certain embodiments the subject methods may further comprise:

removing the amine protecting group Pg₁, and optionally removing the hydroxyl protecting group Pg² from the compound of formula q

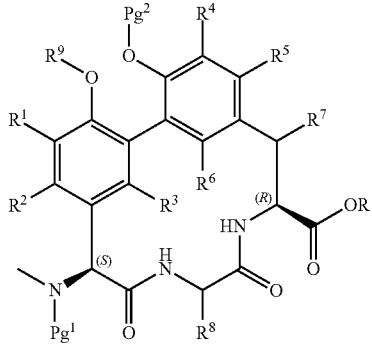

or a salt or solvate thereof;
to form a compound of formula r

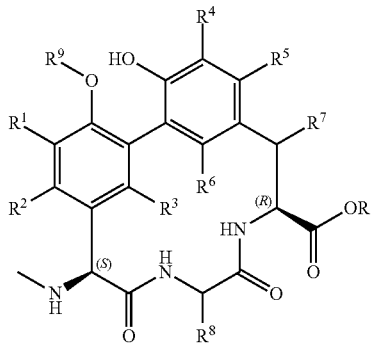

or a salt or solvate thereof;
wherein R, $R^1$, $R^2$, $R^3$, $R^4$, $R^5$, $R^6$, $R^7$, $R^8$, and $R^9$ are as defined herein.

In certain embodiments the subject methods may further comprise:
reacting the compound of formula r

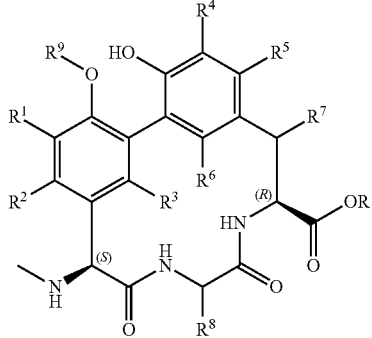

or a salt or solvate thereof;

with an amino acid reagent of formula s

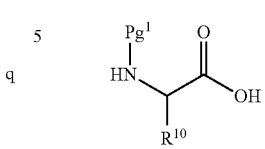

or a salt or solvate thereof,
to form a compound of formula t

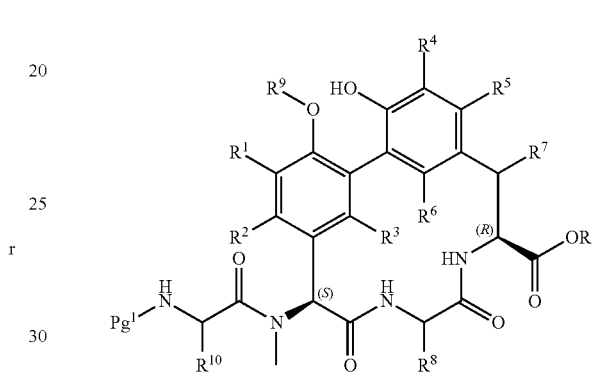

or a salt or solvate thereof;
wherein R, $R^1$, $R^2$, $R^3$, $R^4$, $R^5$, $R^6$, $R^7$, $R^8$, $R^9$, $R^{10}$ and $Pg^1$ are as defined herein.

In certain embodiments the subject methods may further comprise:
removing the amine protecting group $Pg^1$ from, and reacting the compound of formula t

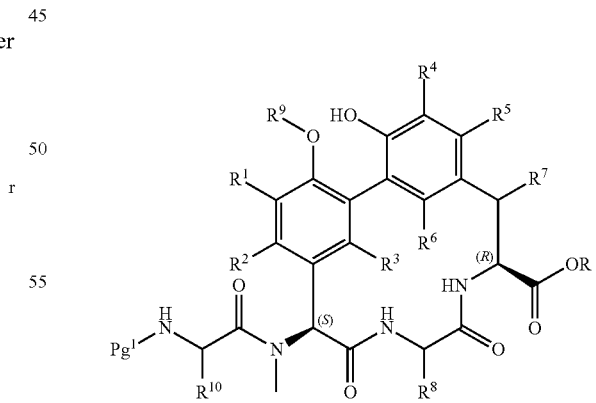

or a salt or solvate thereof;
with a reagent of formula u

TG-COOH        u or a salt or solvate thereof;

to form a compound of formula v

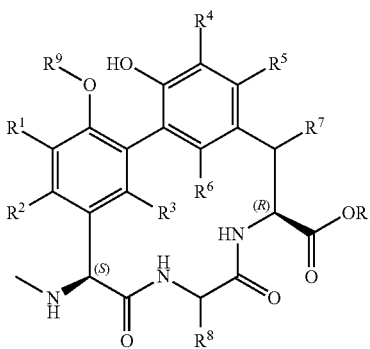
r or a salt or solvate thereof;
wherein R, $R^1$, $R^2$, $R^3$, $R^4$, $R^5$, $R^6$, $R^7$, $R^8$, $R^9$, $R^{10}$ and $Pg^1$ and TG are as defined herein.

In certain embodiments the subject methods may further comprise:
hydrolyzing, and reacting the compound of formula v

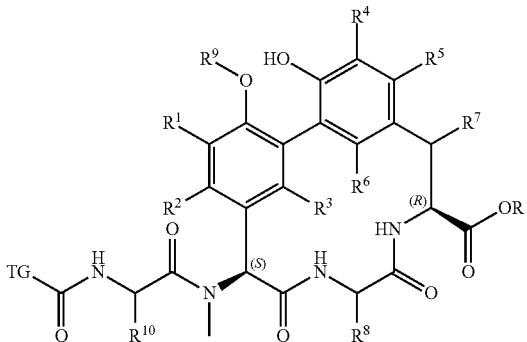
v or a salt or solvate thereof; and
reacting the hydrolysis product of compound v with a reagent of formula u $H_2N$-WG                                        w or a salt or solvate thereof;
to form a compound of formula x

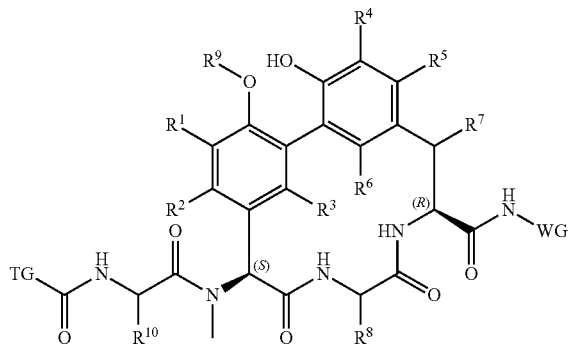
x or a salt or solvate thereof;
wherein R, $R^1$, $R^2$, $R^3$, $R^4$, $R^5$, $R^6$, $R^7$, $R^8$, $R^9$, $R^{10}$ and $Pg^1$, TG and WG are as defined herein.

In certain embodiments of the subject methods, the reagent u is a compound of formula z

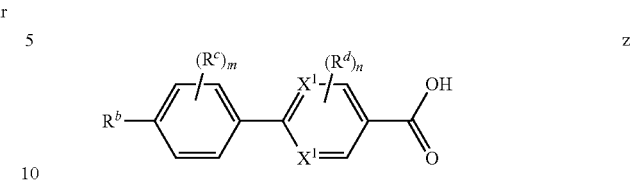
z wherein:
$X^1$ and $X^2$ each independently is N or C;
m and n each independently is 0, 1 or 2;
$R^b$ is:
$C_{1-12}$alkyl which may be unsubstituted or substituted one or more times with halo;
$C_{2-12}$alkenyl which may be unsubstituted or substituted one or more times with halo;
$C_{2-12}$alkynyl which may be unsubstituted or substituted one or more times with halo;
$C_{1-12}$alkoxy which may be unsubstituted or substituted one or more times with halo;
$C_{2-7}$cycloalkyl which may be unsubstituted or substituted one or more times with $C_{1-4}$alkyl, halo-$C_{1-4}$alkyl or halo;
$C_{2-7}$cycloalkyloxy may be unsubstituted or substituted one or more times with $C_{1-4}$alkyl, halo-$C_{1-4}$alkyl or halo;
$C_{1-12}$alkyl-$C_{2-7}$cycloalkyl wherein the cycloalkyl moiety may be unsubstituted or substituted one or more times with $C_{1-4}$alkyl, halo-$C_{1-4}$alkyl or halo;
$C_{2-12}$alkenyl-$C_{2-7}$cycloalkyl wherein the cycloalkyl moiety may be unsubstituted or substituted one or more times with $C_{1-4}$alkyl, halo-$C_{1-4}$alkyl or halo;
$C_{1-12}$alkynyl-$C_{2-7}$cycloalkyl wherein the cycloalkyl moiety may be unsubstituted or substituted one or more times with $C_{1-4}$alkyl, halo-$C_{1-4}$alkyl or halo;
$C_{1-12}$alkyl-$C_{2-7}$cycloalkyloxy wherein the cycloalkyl moiety may be unsubstituted or substituted one or more times with $C_{1-4}$alky, halo-$C_{1-4}$alkyl or halo;
$C_{2-12}$alkenyl-$C_{2-7}$cycloalkyloxy wherein the cycloalkyl moiety may be unsubstituted or substituted one or more times with $C_{1-4}$alkyl, halo-$C_{1-4}$alkyl or halo;
$C_{1-12}$alkynyl-$C_{2-7}$cycloalkyloxy wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkyl wherein the cycloalkyl moiety may be unsubstituted or substituted one or more times with $C_{1-4}$alkyl, halo-$C_{1-4}$alkyl or halo;
$C_{2-7}$cycloalkyl-$C_{2-12}$alkenyl wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkynyl wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkyloxy wherein the cycloalkyl moiety may be unsubstituted or substituted one or more times with $C_{1-4}$alkyl, halo-$C_{1-4}$alkyl or halo;
$C_{2-7}$cycloalkyl-$C_{2-12}$alkenyloxy wherein the cycloalkyl moiety may be unsubstituted or substituted one or more times with $C_{1-4}$alkyl, halo-$C_{1-4}$alkyl or halo;
$C_{2-7}$cycloalkyl-$C_{1-12}$alkynyloxy wherein the cycloalkyl moiety may be unsubstituted or substituted one or more times with $C_{1-4}$alkyl, halo-$C_{1-4}$alkyl or halo;

phenyl-$C_{1-12}$alkyl wherein the phenyl moiety may be unsubstituted or substituted one or more times with $C_{1-4}$alkyl, halo-$C_{1-4}$alkyl or halo;

phenyl-$C_{2-12}$alkenyl wherein the phenyl moiety may be unsubstituted or substituted one or more times with $C_{1-4}$alkyl, halo-$C_{1-4}$alkyl or halo;

phenyl-$C_{1-12}$alkynyl wherein the phenyl moiety may be unsubstituted or substituted one or more times with $C_{1-4}$alkyl, halo-$C_{1-4}$alkyl or halo;

phenyl-$C_{1-12}$alkyloxy wherein the phenyl moiety may be unsubstituted or substituted one or more times with $C_{1-4}$alkyl, halo-$C_{1-4}$alkyl or halo;

phenyl-$C_{2-12}$alkenyloxy wherein the phenyl moiety may be unsubstituted or substituted one or more times with $C_{1-4}$alkyl, halo-$C_{1-4}$alkyl or halo; or phenyl-$C_{1-12}$alkynyloxy wherein the phenol moiety may be unsubstituted or substituted one or more times with $C_{1-4}$alkyl, halo-$C_{1-4}$alkyl or halo; and $R^b$ and $R^c$ each independently is: $C_{1-4}$alkyl, halo-$C_{1-4}$alkyl or halo.

In such embodiments the resulting TG group on compounds v and x is such that TG is

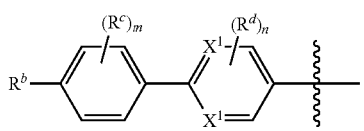

In certain embodiments of the subject methods, the reagent w is cyano-$C_{1-4}$alkylamino, such as glycine nitrile or $H_2N$—$CH_2$—$CN$. so that the group WG is cyano-$C_{1-4}$alkyl such as —$CH_2CN$. In other embodiments WG may be heteroaryl, amido, epoxy, or other group. In such embodiments, the compound of formula x may be of formula A stants in Hz; integration). Mass spectrometry (MS) was performed via electron scatter ionization (ESI) sources.

List of Abbreviations

AcOH Acetic acid
AIBN 2,2'-Azobis(2-methylpropionitrile)
Atm. Atmosphere
(BOC)$_2$O di-tert-Butyl dicarbonate
CbzCl carboxybenzyl chloride
CDMT 6-chloro-2,4-dimethoxy-s-triazine
DCM Dichloromethane/Methylene chloride
DIAD Diisopropyl azodicarboxylate
DIPEA Diisopropylethylamine
DMA Dimethylacetamide
DMAP 4-Dimethylaminopyridine
DME 1,2-Dimethoxyethan
DMF N,N-Dimethylformamide
DMSO Dimethyl sulfoxide
DPPF 1,1'-Bis(diphenylphosphino)ferrocene
EDCI Ethyl-(N',N'-dimethylamino)propylcarbodiimide hydrochloride
Et$_2$O Diethyl ether
EtOH Ethanol/Ethyl alcohol
EtOAc Ethyl acetate
HATU 2-(1H-7-Azabenzotriazol-1-yl)-1,1,3,3-tetramethyl uronium hexafluorophosphate
IBCF Isobutyl chloroformate
HBTU O-Benzotriazol-1-yl-N,N,N',N'-tetramethyluronium hexafluorophosphate
HOAt 1-Hydroxy-7-azabenzotriazole
HOBt 1-Hydroxybenzotriazol
HPLC High pressure liquid chromatograph
KOAc Potassium acetate
METHF Methyltetrahydrofuran
RP HPLC Reverse phase high pressure liquid chromatograph
i-PrOH Isopropanol/isopropyl alcoho

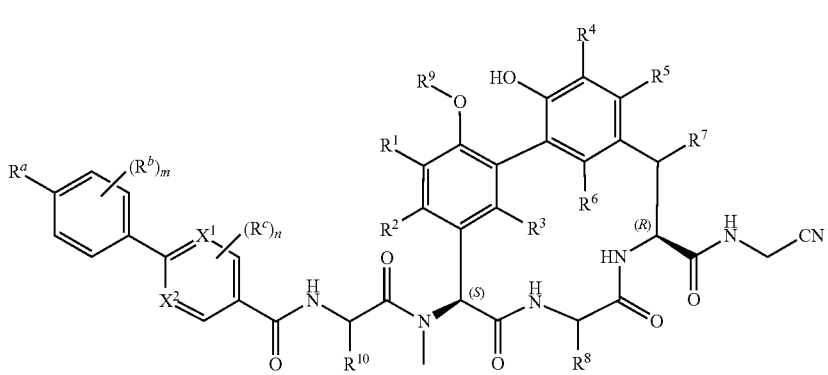

A wherein $R^1$, $R^2$, $R^3$, $R^4$, $R^5$, $R^6$, $R^7$, $R^8$, $R^9$, $R^{10}$, $R^a$, $R^b$, $R^c$, m and n are as defined herein.

Experimental Section

All chemicals, reagents, and solvents were purchased from commercial sources when available and used without further purification. All reactions were carried out under N$_2$ atmosphere and monitored by HPLC. NMR spectra were recorded with a Bruker Avance III spectrometer using a 5 mm BBFO probe at 400 MHz for $^1$H acquisitions. Chemical shifts were referenced to the residual $^1$H solvent signals (DMSO-d6, 2.50). Signals are listed as follows: chemical shift in ppm (multiplicity identified as s=singlet, d=doublet, t=triplet, q=quartet, m=multiplet, br=broad; coupling con- LCMS Liquid Chromatograph/Mass Spectroscopy
MeOH Methanol/Methyl alcohol
MSA Methanesulfonic acid
MW Microwave
NBS N-Bromosuccinimide
NMM N-methylmorpholine
NMP 1-Methyl-2-pyrrolidinone
PSI Pound per square inch
PyBOP (Benzotriazol-1-yloxy)tripyrrolidinophosphonium hexafluorophosphate
r.t. Room temperature
TBAF Tetrabutylammonium chloride
TFA Trifluoroacetic aci THF Tetrahydrofuran
TLC Thin layer chromatography
TSOH Toluenesulfonic acid Example 1

Preparation of (S)-2-(((benzyloxy)carbonyl)(methyl) amino)-2-(4-hydroxy-3-iodophenyl)acetic acid A5

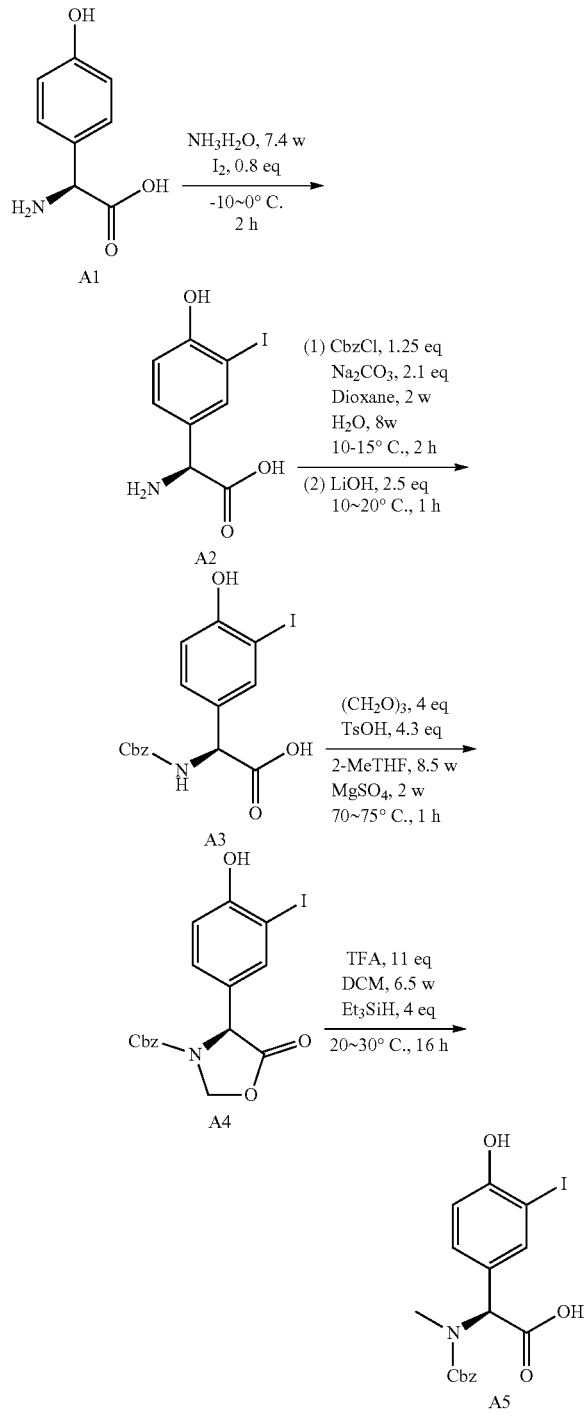

The synthesis of (S)-2-(((benzyloxy)carbonyl)(methyl) amino)-2-(4-hydroxy-3-iodophenyl)acetic acid A5 is illustrated in Scheme 2A.

(S)-2-amino-2-(4-hydroxy-3-iodophenyl) acetic acid (A2)

To a glasslined-reactor (3000 L), were added $NH_3$—$H_2O$ (1246 kg, 7.4 w) and cpd. A1 (167 kg, 999 mol, 1 equiv.). The rxn mixture was cooled to −5° C. $I_2$ was added in 20 portions (202.8 kg, 799 mol, 0.8 equiv.) over a period of 6 h at −10~−5° C. (slightly exotherm was found. max temp. −1° C.). The mixture was stirred at −5~0° C. for 2 h. The mixture was concentrated under vacuum at 50~55° C. jacket temperature (I.T.: 0~42° C.) over 14 h until the pH dropped to 9.7 (9.5~9.8). The residue was diluted with water (2040 kg, 12 w). The solution was acidified by adding 15% HCl aq. (600 kg, 3.6 w) dropwise at 20~32° C. to the pH=~6.3 (5.5~6.4). The mixture was stirred at 25~32° C. for 1 h. The slurry was centrifuged and rinsed with water twice (340 kg, 2 w & 170 kg, 1 w), and acetone twice (100 kg, 0.6 w & 80 kg, 0.5 w). The wet cake was dried under vacuum on 45~50° C. (jacket temperature) for 24 h to afford 141 kg of A2 with 97.9 A % & 87.7 w % (by qNMR) purity & 0.4 w % water content in 48.2% yield (uncorrected) as a light brown solid.
$^1$H NMR (400 MHz; DMSO; $Me_4Si$), δ (ppm): δ 8.25 (s, 2H), 7.71 (d, J=2.0 Hz, 1H), 7.18 (dd, J=8.4, 2.0 Hz, 1H), 6.86 (d, J=8.3 Hz, 1H), 4.20 (s, 1H).

(S)-2-(((benzyloxy)carbonyl)amino)-2-(4-hydroxy-3-iodophenyl)acetic acid (A3)

To a glasslined-reactor (3000 L), were added water (1140 kg, 8 w) and $Na_2CO_3$ (108.2 kg, 1021 mol, 2.1 equiv.) with stirring. A2 (140.1 kg, 478 mol, 1.0 equiv.) was quickly added and the mixture was stirred for 20 min (all A2 dissolved). The rxn mixture was cooled to 10~15° C. A solution of CbzCl (102 kg, 598 mol, 1.25 equiv.) in 1,4-dioxane (280 kg, 2 w) was added dropwise over 4 hrs. while keeping the internal temperature between 10 to 15° C. The reaction mixture was stirred at 10~20° C. for additional 2 hrs. Upon the reaction completion, the rxn mixture was concentrated at 45~55° C. (water batch 55~60° C.) to remove most of 1,4-dioxane (~100 kg 1,4-dioxane & water were collected). The residue was cooled to 20~30° C. and aq. solution of LiOH—$H_2O$ (51 kg, 1215 mol, 2.5 equiv. in 2140 kg of water, 15 w) was added over 1 h. The mixture was stirred for 1 h at 20~30° C. IPC on HPLC: 81.8 A % of A3 (RT=6.1 min), 0.3 A % of bis-Cbz product (RT=7.6 min) & 1.3 A % of A2 remained. The aqueous solution was extracted with the 1st portion of DCM (780 kg, 5.5 w) and the phases were separated. The 2$^{nd}$ portion of DCM (780 kg, 5.5 w) was added to the aqueous phase. About 15% aq. HCl (300 kg) was added dropwise at 20~30° C. adjust the pH to 2~3 (slight exothermic & large amount of gas released as pH dropped to ~6). The phases were separated and the aqueous was extracted with 3$^{rd}$ portion of DCM (500 kg, 3.5 w). The organic phases (the 2$^{nd}$ and 3$^{rd}$ portion of DCM extracts) were combined and dried over $Na_2SO_4$ (50 kg) for 1 hr. The mixture was filtered. The solid was washed with a small amount of DCM and the filtrate was concentrated at 40~50° C. (jacket temperature, 55~60° C.) to remove most of the solvent. EtOAc (210 kg, 1.5 w) was added and the mixture was continuously concentrated under vacuum at 40~50° C. to purge the residual DCM. EtOAc (210 kg, 1.5 w) was again added and then concentrated under vacuum at 40~50° C. to ~300 kg. petroleum ether (600 kg, 4.3 w) was added over 30 min (large amount of white solids precipitated out). The slurry was cooled to 10~15° C. and stirred for 2 h at 10~15° C. The mixture was filtered & the cake was washed with petroleum ether/EtOAc (120 kg, 3/1, w/w, 0.9 w). The wet cake was dried under vacuum at 40~50° C. (water bath, 45~50° C.) for 30 h to afford 205.1 kg of A3 with 94 A % & 79.3 w % (by qNMR) purity in 98.4% yield (uncorrected) as a light-brown solid.

$^1$H NMR (400 MHz; DMSO; Me$_4$Si), δ (ppm): δ 12.80 (s, 1H), 10.39 (s, 1H), 8.04 (d, J=8.0 Hz, 1H), 7.70 (d, J=2.1 Hz, 1H), 7.39-7.26 (m, 5H), 7.22 (dd, J=8.4, 2.1 Hz, 1H), 6.83 (d, J=8.3 Hz, 1H), 5.09-4.99 (m, 3H).

(S)-benzyl 4-(4-hydroxy-3-iodophenyl)-5-oxooxazolidine-3-carboxylate (A4)

To a 3000 L reactor, were charged 2-MeTHF (840 kg, 5 w) and A3 (169.4 kg, 388.6 mol, 1 equiv.). The mixture was stirred for 10 min (all solid was dissolved). TsOH—H$_2$O (317.8 kg, 1671 mol, 4.3 equiv.) was then added and followed by MgSO$_4$ (332 kg, 2 w). The reactor was degassed and refilled with N$_2$ 3 times. The suspension was heated to 70~75° C. A solution of (CH$_2$O)$_3$ (140 kg, 1554 mol, 4 equiv.) in 2-MeTHF (580 kg, 3.5 w) was added dropwise over 3 hrs. at 70~75° C. The rxn mixture was stirred at 70~75° C. for another 1 hr. (a sample was taken for HPLC analysis: A3<5 A %). The rxn mixture was cooled to 25~30° C. and 2700 kg (16 w) of water (15~20° C.) was added over 3 hrs. (mild exothermic. IT rose to 28° C. from 20° C.). Stopped agitation and allowed separation of phases. The aqueous phase was extracted with EtOAc (800 kg, 5 w). The organic phases were combined and washed with aq. Na$_2$CO$_3$ which was made by dissolving 29 kg Na$_2$CO$_3$ in 1600 kg of water (the pH of the resulting aqueous was ~9). The phases were separated and the organic phase was washed with brine (50 kg NaCl in 600 kg water). The organic phase was dried over anhydrous Na$_2$SO$_4$ (50 kg) for 1 hr. before filtration. The filtrate (combined with the filtrate from the batch with 30.6 kg of A3) was concentrated at 40~45° C. (jacket temperature 45~50° C.) under vacuum to 300~350 kg stage. Petroleum ether (400 kg, 2 w) was added and the mixture was concentrated under vacuum at 40~45° C. again to 350~400 kg stage again (a large amount of solid was precipitated out). Petroleum ether (780 kg, 4 w) was added. The suspension was cooled to 15~25° C. and stirred for 1 hr. The suspension was filtered. The solid was dried under vacuum at 35~45° C. for 24 h to afford 142 kg of A4 with 89.1 A % (HPLC) & 86.4 w % (by qNMR) purity in 69.6% yield as a light brown solid.

$^1$H NMR (400 MHz, DMSO) δ 10.50 (s, 1H), 7.70 (s, 1H), 7.43-7.19 (m, 5H), 7.03 (s, 1H), 6.87 (d, J=8.3 Hz, 1H), 5.58 (d, J=43.9 Hz, 2H), 5.27 (s, 1H), 5.14 (d, J=12.5 Hz, 1H), 5.05 (s, 1H).

(S)-2-(((benzyloxy)carbonyl)(methyl)amino)-2-(4-hydroxy-3-iodophenyl)acetic acid (A5)

To a 3000 L reactor, were charged DCM (920 kg, 6.5 w), A4 (142 kg, 324 mol, 1 equiv.), TFA (407 kg, 3559 mol, 11 equiv.) and Et$_3$SiH (150.5 kg, 1294 mol, 4 equiv.). The mixture was stirred at 25~30° C. for 13 hrs. (IPC on HPLC showed: 88.3 A % of A4 and 2.6 A % of A4 remained). The mixture was concentrated under vacuum at 25~45° C. (jacket temperature: 40~45° C.) to ~400 kg stage. The residue was cooled to 20~30° C. and DCM (1400 kg, 10 w) was added. Na$_2$CO$_3$ solution (140 kg of Na$_2$CO$_3$ dissolved in 1260 kg water) was added to adjust the pH of the DCM solution to ~9. The phases were separated. DCM (700 kg, 5 w) was added to aqueous and then the pH of the mixture was adjusted to ~2 with ~100 kg 30% HCl. The mixture was then stirred at 15~25° C. for ~2 hrs. before filtration. The cake was rinsed with water (140 kg, 1 w) and slurried in DCM (650 kg, 4.5 w) at 15~25° C. for ~1 hr. The slurry was centrifuged and rinsed with DCM (140 kg, 1 w). The wet cake was dried at 35~45° C. (jacket temperature: 40~45° C.) for 30 h under vacuum. About 101 kg of A5 was obtained in 70.8% yield (uncorrected) as an off-white solid (98.9 A % purity, >99% de, 91.5 w % (by qNMR) & 1.3 w % KF).

$^1$H NMR (400 MHz; DMSO; Me$_4$Si), δ (ppm): $^1$H NMR (400 MHz, dmso) δ 13.10 (s, 1H), 10.55 (s, 1H), 7.56 (s, 1H), 7.41-7.28 (m, 5H), 7.12 (d, J=8.3 Hz, 1H), 6.90 (d, J=8.3 Hz, 1H), 5.65 (s, 1H), 5.13 (s, 2H), 2.66 (s, 3H).

Example 2

Preparation of (5-((S)-2-((S)-2-aminopropanamido)-3-methoxy-3-oxopropyl)-2-(benzyloxy)phenyl)boronic acid hydrochloride (A14)

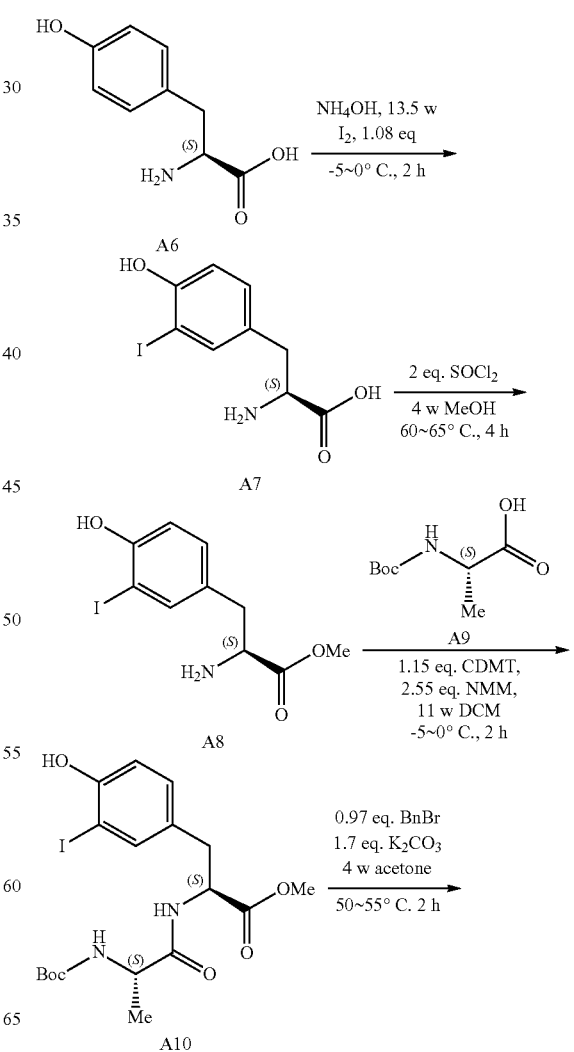

Scheme 2B

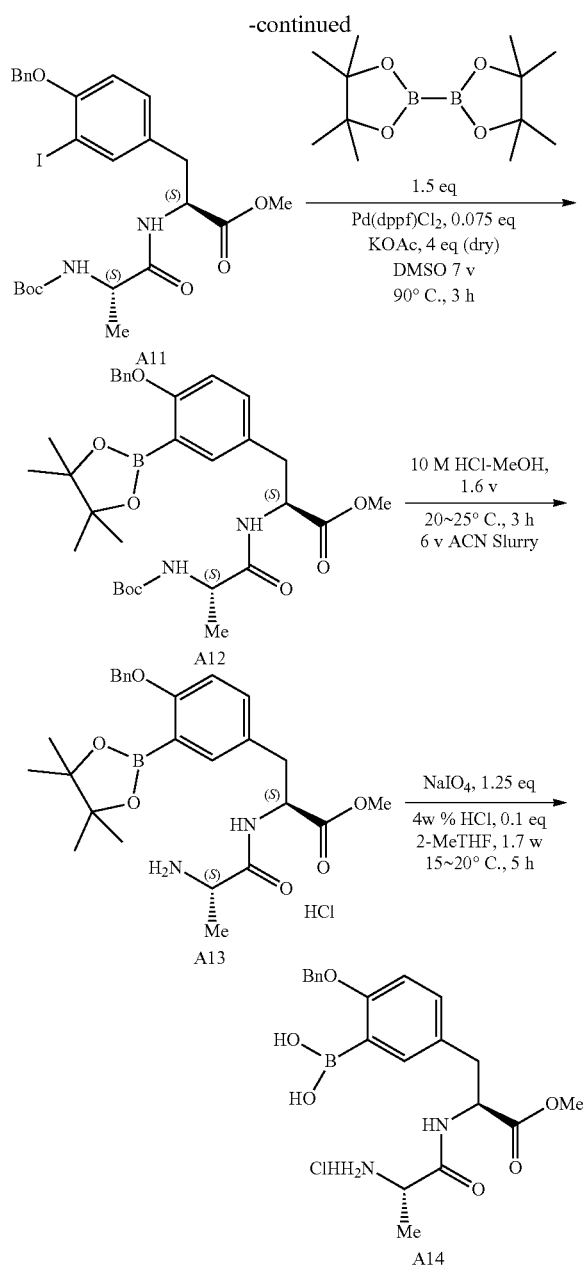

The synthesis of (5-((S)-2-((S)-2-aminopropanamido)-3-methoxy-3-oxopropyl)-2-(benzyloxy)phenyl)boronic acid hydrochloride A14 is illustrated in Scheme 2B.

(S)-2-amino-3-(4-hydroxy-3-iodophenyl)propanoic acid (A7)

To a 3000 L flask, were added A6 (147.3 kg, 813 mol, 1 equiv.) and conc. NH$_3$H$_2$O (25%, 1980 kg, 13.5 w). The white suspension was cooled to −10~0° C. I$_2$ (223 kg, 878 mol, 1.08 equiv.) was added in 40 portions over a period of ~5 hrs. at −10~0° C. The solution was stirred at −10~0° C. for ~2 hrs. (a sample was taken from the mixture and diluted with water for IPC on HPLC: 86.4 A % of A7 & 11.3 A % of bis-iodide (not shown in Scheme 2B) and 2.3 A % of A6 remained). It was then concentrated under vacuum at 0~40° C. for ~28 hrs. until the pH of the residue dropped to 9.6. The residue solution was cooled to 20~30° C. Aqueous HCl (18 w %) was added dropwise at 20~30° C. over 10 h to adjust the pH to 8 before A7 (0.25 kg) was added as seeds. After the mixture was continuously stirred for ~1 h at 20~30° C., the pH of the mixture was continuously adjusted using aqueous HCl (18 w %) to 7.4 over ~3 hrs. and 6.6 over ~1 hr., and stirred for 1 hr. at each pH stage. The resultant was stirred at 20~30° C. for 2 h (a total of ~1200 kg of 18 w % aq. HCl was used for crystallization). The slurry was centrifuged. The wet cake was washed twice with water (230 kg, 1.6 w, each) and then twice with acetone (230 kg, 1.6 w, each). The solid was dried under vacuum at 50-60° C. for ~48 hrs. to afford 156.6 kg of A7 with 96 A % purity & 2.5 w % water content as a light brown solid in 62.6% yield (uncorrected; subtract 0.25 kg of A7 seed).

(S)-methyl 2-amino-3-(4-hydroxy-3-iodophenyl)propanoate (A8)

To a 2000 L reactor, were added MeOH (640 kg, 4 w) and A7 (156 kg, 508 mol, 1 equiv.) with stirring. The reactor was degassed and re-filled with N$_2$ twice. The resulting suspension was cooled to −5° C. to 5° C. SOCl$_2$ (122 kg, 1029 mol, 2 equiv.) was added dropwise over 2.5 hrs. while maintaining I.T.<5° C. (exothermic. max 4.5° C. All solid dissolved). The rxn solution was stirred at −5° C. to 5° C. for 1 hr. and then heated to 55~65° C. slowly (~3 h) and stirred for 2 h (a sample was taken for IPC on HPLC: 96.9 A % of A8 & 0.4 A % of A7 remained). The mixture was cooled to <50° C. and concentrated under vacuum at 40~55° C. to ~450 kg of residue (solids started to be precipitate out). EtOAc (240 kg, 1.5 w) was added to the residue and the mixture was concentrated under vacuum at 40~55° C. to ~400 kg of residue. A second part of EtOAc (240 kg, 1.5 w) was added to the residue and the mixture was concentrated again under vacuum at 30~55° C. to ~400 kg of residue. A third part of EtOAc (125 kg, 0.8 w) was added to the residue and the mixture was concentrated under vacuum at 30~45° C. to ~400 kg of the final residue. EtOAc (125 kg, 0.8 w) was thus added to the residue and followed by adding petroleum ether (95 kg, 0.6 w). The suspension was cooled to 15~25° C. and stirred for ~1 hr. The mixture was filtered and the cake was rinsed with EtOAc/petroleum ether (65 kg/55 kg, 0.45 w/0.35 w). The wet cake was dried under vacuum at 40~50° C. for 36 hrs. and ~161 kg of A8 HCl salt with 96.3 A % & 86.5 w % (by qNMR) purity in 88.6% yield (uncorrected) was obtained as a white solid.

$^1$H NMR (400 MHz; DMSO; Me$_4$Si), δ (ppm): $^1$H NMR (400 MHz, dmso) δ 10.49 (s, 1H), 8.67 (s, 2H), 7.53 (d, J=1.6 Hz, 1H), 7.32 (d, J=50.0 Hz, 1H), 7.03 (dd, J=8.3, 1.6 Hz, 1H), 6.91 (d, J=8.2 Hz, 1H), 4.17 (t, J=6.2 Hz, 1H), 3.68 (s, 2H), 3.02 (qd, J=14.2, 6.4 Hz, 1H).

(S)-methyl 2-((S)-2-((tert-butoxycarbonyl)amino)propanamido)-3-(4-hydroxy-3-iodophenyl)propanoate (A10)

To a 1000 L reactor, were added DCM (780 kg, 11 w), A9 (43 kg, 227 mol, 1.15 equiv.) & CDMT (39.9 kg, 227 mol, 1.15 equiv.). The reactor was degassed and refilled with N$_2$ twice. NMM (33.9 kg, 193.3 mol, 1.7 equiv.) was then added dropwise over ~40 min, while maintaining the I.T. at −5 to 5° C. (slightly exothermic). The suspension was stirred at −5 to 5° C. for 1 hr. before use. To another 2000 L reactor, were added DCM (390 kg, 5.5 w), A8-HCl (70.6 kg, 197.4 mol, 1 equiv.) & NMM (17 kg, 167.8 mol, 0.85 equiv.). The reactor was degassed and refilled with N$_2$ twice. The suspension was cooled to −5 to 0° C. and the solution of A9/CDMT/NMM/DCM was added dropwise over 2 hrs. below 0° C. (slightly exothermic). The mixture was stirred at −5~0° C. for 2 hrs.(a sample was taken from the rxn mixture for IPC on HPLC: 75 A % of A10 & 1.9 A % of A8-HCl remaining). The rxn was quenched by adding a solution of citric acid (9 kg dissolved in 360 kg of water) dropwise over 30 min below 0° C. and stirred for additional ~30 min. before filtration. The phases (the filtrate) were separated and the organic phase was washed with aqueous NaHCO$_3$ (6 kg dissolved in 60 kg water), and then water (180 kg×2). The organic phase was concentrated under vacuum at 30~40° C. to ~100 kg of residue. Acetone (45 kg, 0.6 w) was added and the mixture was concentrated under vacuum at 35~45° C. to ~100 kg of residue again. This repeated one more time to purge DCM. More acetone (240 kg, 3.4 w) was added and the solution was cooled to 15~25° C. The A10/acetone solution (330 kg) was used directly for next step.

MS (ESI, m/z): 493 (M$^+$).

(S)-methyl 3-(4-(benzyloxy)-3-iodophenyl)-2-((S)-2-((tert-butoxycarbonyl)amino)propanamido)propanoate (A11)

To a 2000 L reactor, were added the solution of S,S-E21 in acetone (725 kg solution, calculated as 230.9 kg of A10 from 150.6 kg of A8 HCl in 100% yield), K$_2$CO$_3$ (100 kg, 723.5 mol, 1.7 equiv.) and Benyl Bromide (70 kg, 409.3 mol, 0.97 equiv.). The mixture was heated to 50~58° C. and stirred for 2 hrs. (a sample was taken for IPC on HPLC: 65 A % of A11 & nil of A10 remaining). The mixture was cooled to 25~30° C. and filtered. The cake was rinsed with DCM (250 kg, 1.7 w of A8-HCl). The combined filtrate was concentrated under vacuum at 30~50° C. to ~300 kg of residue and petroleum ether (800 kg, 5.3 w of A8-HCl) was added over 20 min. The mixture was cooled to 0~10° C. and stirred for 1 h. The slurry was filtered and the cake was rinsed with DCM/petroleum ether (45 kg/90 kg). The wet cake (~240 kg) was dissolved in DCM (500 kg, 3.3 w of A8-HCl) at 20~30° C. Petroleum ether (500 kg, 3.3 w of A8-HCl) was added dropwise over 40 min. The slurry was cooled to 0~5° C. and stirred for 1 h. The slurry was filtered. The wet cake was slurried in DCM/petroleum ether (250 kg/500 kg) at 20~30° C. for 0.5 h. The slurry was filtered and the cake was rinsed with DCM/petroleum ether (45 kg/90 kg). The wet cake was dried under vacuum at 20~40° C. (jacket temperature, 40~45° C.) for ~30 hrs. About 134.6 kg of A11 was obtained as an off-white solid with 96.6 A % purity, >99% de & 96.1 w % (by qNMR) in 54.9% yield (uncorrected) over 2 steps from 150.6 kg of A8-HCl.

$^1$H NMR (400 MHz; DMSO; Me$_4$Si), δ (ppm): $^1$H NMR (400 MHz, dmso) δ 8.09 (d, J=7.6 Hz, 1H), 7.61 (s, 1H), 7.47 (d, J=7.3 Hz, 2H), 7.38 (t, J=7.6 Hz, 2H), 7.30 (t, J=7.2 Hz, 1H), 7.17 (d, J=7.3 Hz, 1H), 6.96 (d, J=8.4 Hz, 1H), 6.81 (d, J=7.7 Hz, 1H), 5.13 (s, 2H), 4.39 (d, J=6.5 Hz, 1H), 3.99-3.85 (m, 1H), 3.56 (s, 3H), 2.98-2.77 (m, 2H), 1.35 (s, 8H), 1.10 (d, J=7.1 Hz, 3H).

MS (ESI, m/z): 583 (M$^+$).

(S)-methyl-3-(4-(benzyloxy)-3-(4,4,5,5-tetramethyl-1,3,2-dioxaborolan-2-yl)phenyl)-2-((S)-2-((tert-butoxycarbonyl)amino)propanamido)propanoate (A12)

To a 1000 L reactor, were added DMSO (460 kg, 7.5 w), A11 (61 kg, 104.7 mol, 1 equiv.), bis(pinacolato)diboron (39.9 kg, 157.1 mol, 1.5 equiv.) and KOAc (41.1 kg, 418.9 mol, 4 equiv.). The mixture was degassed with N$_2$ for 5 times. Pd(dppf)Cl$_2$ (5.75 kg, 7.9 mol, 0.075 equiv.) was added under N$_2$ and the mixture was degassed/refilled with N$_2$ for 5 times. The resulting mixture was heated to 60~90° C. and stirred for ~3 hrs. Upon the rxn completion, the reaction mixture was cooled to 25~30° C. and quenched into a mixture of water (610 kg, 10 w) & MTBE (670 kg, 11 w). The mixture was filtered through a diatomite pad (25 kg). The phases (the filtrate) were separated and the aqueous was extracted with MTBE (115 kg, 1.9 w). The combined MTBE extracts were dried over anhydrous Na$_2$SO$_4$ (50 kg) for 1 hr. before filtration. The cake was rinsed with MTBE (30 kg, 0.5 w) and the combined filtrate was concentrated under vacuum at 25~40° C. to afford 407 kg of MTBE solution which was used for next step directly.

(S)-methyl 2-((S)-2-aminopropanamido)-3-(4-(benzyloxy)-3-(4,4,5,5-tetramethyl-1,3,2-dioxaborolan-2-yl)phenyl)propanoate (A13)

To a 1000 L reactor, was added MeOH (214 kg, 1.7 w of A11) and cooled to −10~0° C. under N$_2$. Gaseous HCl (123.4 kg, 1.0 w) was charged below 0° C. over 20 hrs. To another 2000 L reactor, was added the A12/TBME solution (784 kg, from 122 kg of A11). The HCl/MeOH solution (337 kg) obtained above was added slowly at 15~25° C. over 2.5 hrs. (evolution of gas). The resulting solution was stirred at 15~25° C. for 2 hrs. Upon the rxn completion, the mixture was concentrated under vacuum at 20~45° C. to ~350~400 kgs residue (~3 w of A11). ACN (190 kg, 1.6 w of A11) was added and the mixture was distilled at 30~45° C. under vacuum until solids began to precipitate out. More ACN (920 kg, 7,5 w of A11) was added. The mixture was cooled to 10~20° C. and stirred for 1 h. The slurry was filtered and the cake was rinsed with ACN (60 kg). The wet product was dried at 30~45° C. under vacuum for 24 hrs. to give 84.3 kg of A13-HCl/A14-HCl as a light brown solid with 97.7 A % purity (34.3 A % of A13-HCl & 63.4 A % of A14-HCl) & 73.5 w % (by qNMR) in 77.3% yield (uncorrected) over 2 steps from 122 kg of A12.

$^1$H NMR (400 MHz; DMSO; Me$_4$Si), δ (ppm): $^1$H NMR (400 MHz, dmso) δ 8.99 (d, J=7.4 Hz, 1H), 8.30 (s, 3H), 7.58 (d, J=7.2 Hz, 2H), 7.52 (s, 3H), 7.43-7.31 (m, 7H), 7.27 (d, J=7.1 Hz, 4H), 6.97 (d, J=8.3 Hz, 1H), 5.08 (s, 2H), 4.37 (dd, J=13.6, 8.1 Hz, 1H), 3.80 (s, 1H), 3.58 (s, 3H), 2.94 (ddd, J=22.7, 13.9, 7.3 Hz, 2H), 2.05 (s, 1H), 1.35 (d, J=7.0 Hz, 3H), 1.28 (s, 12H).

(5-((S)-2-((S)-2-aminopropanamido)-3-methoxy-3-oxopropyl)-2-(benzyloxy)phenyl)boronic acid hydrochloride (A14)

To a 500 L reactor, were added 2-MeTHF (70 kg, 1.7 w), water (72 kg, 1.8 w), and a mixture of A13-HCl & A14-HCl (40 kg, 77.1 mol, 1 equiv., calculated as 100% S,S-A13 HCl). The mixture was stirred for ~15 min or until most of A13-HCl & A14-HCl was dissolved. NaIO$_4$ (20.6 kg, 96.4 mol, 1.25 equiv.) was added in 10 portions over 30 min at 10~15° C. and the suspension was stirred for additional 15 min. A HCl aqueous solution (4 w %, 7.4 kg, 0.105 eq.) was added slowly at 10~15° C. over 1.5 hrs. The mixture was warmed to 15~20° C. and stirred for 6 hrs (slightly exothermic). Upon the rxn completion, the mixture was filtered and the solid was rinsed with MeTHF (8 kg, 0.2 w). Aqueous NaHSO$_3$ solution (16 kg NaHSO$_3$ in 48 kg water) was added slowly to above combined filtrate below 15° C. over ~0.5 hrs.(exothermic). The phases were separated and the aqueous was extracted with MeTHF (28 kg, 0.7 w). The MeTHF extracts were combined and washed with brine (16 kg NaCl in 64 kg water). The organic phase was dried over anhydrous Na$_2$SO$_4$ (120 kg) for 2 hrs. before filtration. The cake was rinsed with MeTHF (30 kg, 0.75 w). The MeTHF solution obtained above was added slowly to TBME (460 kg, 11.5 w) over 2 hrs. with stirring at 10~15° C. (solid was precipitated out upon the completion of adding MeTHF solution). The slurry was stirred at 10~15° C. for additional 1 hr. before filtration. The wet product was dried at 5~15° C. under vacuum for ~72 hrs. to give ~26 kg of A14-HCl as a light brown solid with 96 A % purity & 90 w % (by qNMR) in 77.2% yield (uncorrected).

$^1$H NMR (400 MHz; DMSO; Me$_4$Si), δ (ppm): $^1$H NMR (400 MHz, dmso) δ 8.90 (d, J=7.3 Hz, 1H), 8.20 (s, 3H), 7.72 (s, 2H), 7.47 (dd, J=9.1, 4.6 Hz, 3H), 7.40 (t, J=7.5 Hz, 2H), 7.33 (t, J=7.0 Hz, 1H), 7.27 (d, J=8.3 Hz, 1H), 6.99 (d, J=8.4 Hz, 1H), 5.15 (s, 2H), 4.43 (dd, J=13.7, 7.9 Hz, 1H), 3.83 (s, 1H), 3.61 (s, 3H), 2.94 (ddd, J=22.9, 13.9, 7.2 Hz, 2H), 1.36 (d, J=6.9 Hz, 3H).

Example 3

Preparation of Methyl(4S,7S,10S)-26-(benzyloxy)-10-(((benzyloxy)carbonyl)(methyl)amino)-16-hydroxy-7-methyl-6,9-dioxo-5,8-diaza-1,2(1,3)-dibenzenacyclodecaphane-4-carboxylate (A16)

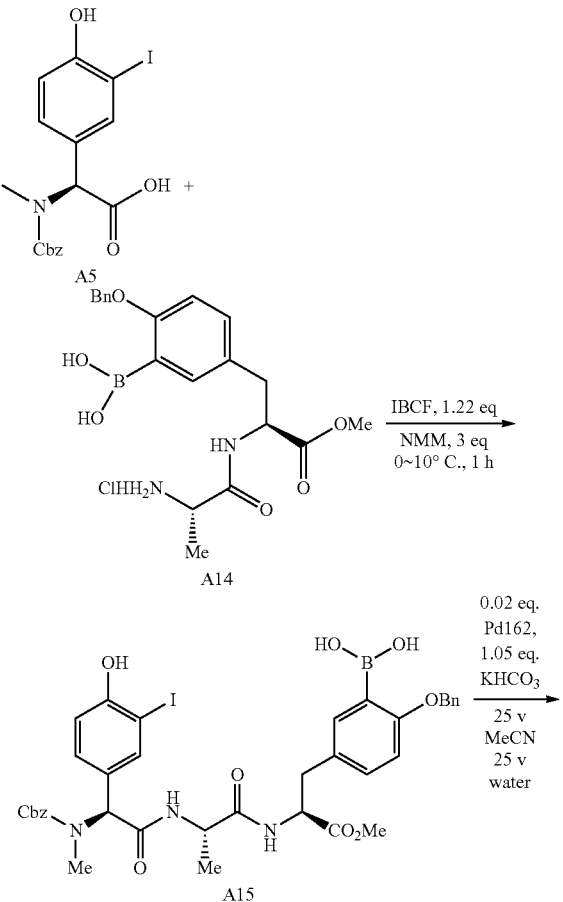

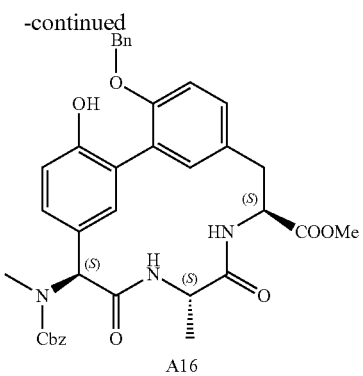

The synthesis of Methyl(4S,7S,10S)-26-(benzyloxy)-10-(((benzyloxy)carbonyl)(methyl)amino)-16-hydroxy-7-methyl-6,9-dioxo-5,8-diaza-1,2(1,3)-dibenzenacyclodecaphane-4-carboxylate (A16) is illustrated in Scheme 2C.

(2-(benzyloxy)-5-((5S,8S,11S)-5-(4-hydroxy-3-iodophenyl)-11-(methoxycarbonyl)-4,8-dimethyl-3,6,9-trioxo-1-phenyl-2-oxa-4,7,10-triazadodecan-12-yl)phenyl)boronic acid (A15)

To a 500 L reactor, were added DMA (72 kg), THF (137 kg), A14-HCl (25.64 kg, 58.7 mol, 1 equiv.) & A5 (25.91 kg, 58.7 mol, 1 equiv.) with stirring under N$_2$. The mixture was cooled to <−10° C. before NMM (17.8 kg, 176.1 mol, 3 equiv.) was added slowly over 10 min below −10° C. (slightly exothermic). The mixture was further cooled to −20 to −15° C. and a solution of IBCF (8.02 kg, 0.46 mol, 1 equiv.) in DMA/THF (48.2 kg/91.3 kg, 1.9 w/3.6 w of A14-HCl) was added slowly over 9 hrs. at −20 to −15° C. (exothermic). The mixture was stirred for 5 min and a sample was taken for IPC on HPLC: 83.9 A % of SSS-10a and 0.9 A % of A14 remaining. To a 2000 L reactor, were added water (520 kg), Na$_2$CO$_3$ (25.6 kg) & EA (230 kg). The mixture was pre-cooled to −5~0° C. before use. The rxn mixture was added slowly to the mixture of aqueous Na$_2$CO$_3$ & EA below 0° C. over 1 hr. Then, the resulting mixture was stirred for 20 min. before filtration. The phases (the filtrate) were separated. The organic phase was washed with aq NH$_4$Cl (64 kg NH$_4$Cl dissolve in 260 kgs of water), followed by brine for 3 times (50 kgs of NaCl dissolved in 250 kg water, each). The organic phase was dried over anhydrous Na$_2$SO$_4$ (30 kg). Filtered and the cake was rinsed with EA (30 kg). The Filtrate was concentrated under vacuum at 30~45° C. to ~50 kgs residue (2~2.5 w of A14-HCl). EtOH (20 kg) was added and the mixture was distilled under vacuum at 30~45° C. to ~50 kg again (2~2.5 w of A14-HCl). This operation was repeated twice (each with 20 kg EtOH) to remove EtOAc (GC: <5 A % of EA in the residue) (product began to be precipitated out during the 3$^{rd}$ time concentration). More EtOH (51.3 kg, 2 w of A14-HCl) was added. The mixture was heated to 60~65° C. and stirred for 3 hrs. (some solids was dissolved). Then, n-heptane (74 kg, 2.9 w of A14-HCl) was added slowly over 1 hr. (during the addition, the internal temperature was dropped to 35~40° C.). The mixture was stirred for 0.5 h and the internal temperature was further cooled to 15~25° C. More n-heptane (103 kg, 4 w of A14-HCl) was added slowly over 1 hr. and the resulting mixture was stirred for 2 hrs. at 15~25° C. The slurry was filtered and the cake was washed with EtOH/n-heptane (11 kg/36 kg). The wet cake was dried under vacuum at 30~45° C. for 8 hrs. to give 29.1 kgs of A15 as an off-white solid with 95.9 A % & 91.2 w % purity, 98.8% de in 60.3% yield (uncorrected).

$^1$H NMR (400 MHz; DMSO; Me$_4$Si), δ (ppm): $^1$H NMR (400 MHz, DMSO) δ 10.44 (s, 1H), 8.33 (dd, J=12.1, 7.2 Hz, 2H), 7.71 (s, 2H), 7.54-7.28 (m, 12H), 7.24 (d, J=7.5 Hz, 1H), 7.05 (d, J=7.7 Hz, 1H), 6.95 (d, J=8.4 Hz, 1H), 6.84 (d, J=8.4 Hz, 1H), 5.75 (s, 1H), 5.11 (s, 4H), 4.36 (dt, J=14.5, 7.2 Hz, 2H), 3.56 (s, 3H), 2.91 (ddd, J=21.8, 13.7, 7.2 Hz, 2H), 2.62 (s, 3H), 1.17 (s, 3H). MS (ESI, m/z): 824 (M$^+$).

Methyl(4S,7S,10S)-26-(benzyloxy)-10-(((benzyloxy)carbonyl)(methyl)amino)-16-hydroxy-7-methyl-6,9-dioxo-5,8-diaza-1,2(1,3)-dibenzenacyclodecaphane-4-carboxylate (A16)

To a flask, were charged A15 (300 g, 90.5 w %, 329.7 mmol, 1.0 equiv.), KHCO$_3$ (38.1 g, 380 mmol, 1.15 equiv.) and Pd-162 (chloro(crotyl)(tri-tert-butylphosphine)palladium(II), CAS #1334497-00-5) (3 g, 7.2 mmol, 0.02 equiv.). The rxn vessel was evacuated and backfilled with N$_2$ (5 min×3). Acetonitrile (7.5 L, 25 v) and DI water (7.5 L, 25 v) (acetonitrile & DI water evacuated and backfilled with N$_2$ 10 min×3 times respectively in advance) were added under N$_2$. The vessel containing the rxn mixture was again evacuated and backfilled with N$_2$ (15 min). The mixture was heated to 65° C. over ~1 h and stirred for additional 1.5 h or until the completion of the reaction (A15: <1.0 A % on HPLC). The rxn mixture was cooled to ambient temperature and diluted with DCM (27 v, 8 L). The phases were separated and the aqueous was extracted with DCM (~8 v, 2 L). The combined organic phase was dried with Na$_2$SO$_4$ (300 g, 1 w) for 20 min. Filtered and the cake was washed with DCM (2 L). The combined filtrate and wash was concentrated under vacuum at 45° C. to afford crude A16 (~250 g) as a brown solid with 85 A % LC purity. The crude solid was used for next step without any further purification.

$^1$H NMR(400 MHz; DMSO; Me$_4$Si), δ (ppm): 9.31 (1 H, d, J=4 Hz), 9.09 (1 H, t, J=8 Hz), 8.51-8.41 (1 H, dd, J=22 Hz) 7.44-6.68 (16 H, m), 5.97 (1 H, d, J=4 Hz), 5.16-5.12 (4 H, m), 4.84-4.82 (1 H, m), 4.72-4.77 (1 H, m), 3.37 (3 H, t, J=8 H), 3.31-3.27 (1 H, m), 3.05-2.98 (1 H, m), 2.64-2.60 (3 H, d, J=16 Hz), 1.20-1.15 (3 H, m) MS (ESI, m/z): 652 (M$^+$).

Example 4

Alternate preparation of Methyl(4S,7S,10S)-26-(benzyloxy)-10-(((benzyloxy)carbonyl)(methyl)amino)-16-hydroxy-7-methyl-6,9-dioxo-5,8-diaza-1,2(1,3)-dibenzenacyclodecaphane-4-carboxylate (A16)

Scheme 2D

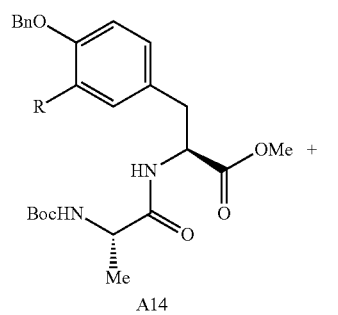

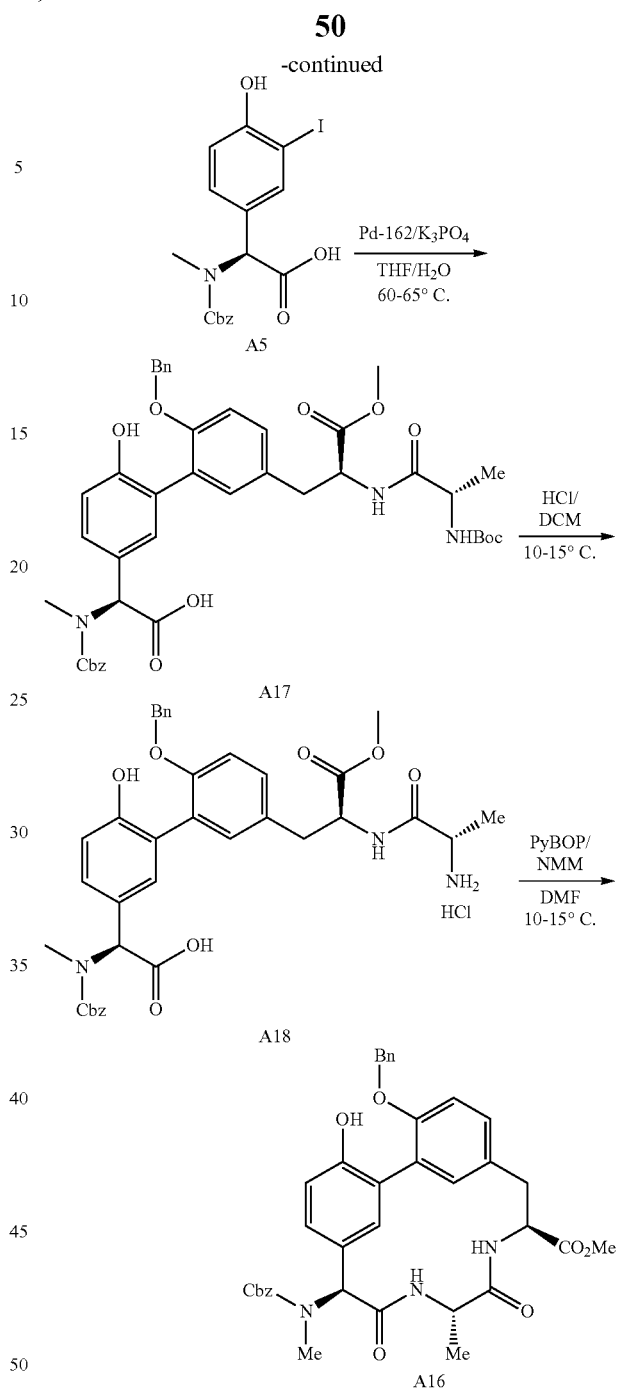

Scheme 2D illustrates an alternate route to synthesis of Methyl(4S,7S,10S)-26-(benzyloxy)-10-(((benzyloxy)carbonyl)(methyl)amino)-16-hydroxy-7-methyl-6,9-dioxo-5,8-diaza-1,2(1,3)-dibenzenacyclodecaphane-4-carboxylate (A16)

3-{6-Benzyloxy-5'-[(benzyloxycarbonyl-methylamino)-carboxy-methyl]-2'-hydroxy-biphenyl-3-yl}-2-(2-tert-butoxycarbonylamino-propionylamino)-propionic acid methyl ester (SSS-E24c)

To a flask (5 L) were added A12 (100.0 g, 226.8 mmol, 1.0 equiv), A13/A14 (130.0 g, 223.3 mmol, 0.98 equiv.), Pd-162 (5.7 g, 13.6 mmol, 0.06 equiv) and K$_3$PO$_4$(48.1 g, 226.8 mmol, 1.0 equiv.) under N$_2$. A mixture of THF & H$_2$O (1/1, 3 L, sparged with nitrogen for at least 15 min. before use) was then added under stirring. The solution was purged under vacuum and back-filled with nitrogen and repeated for three times. The reaction mixture was heated to 60~65° C. and stirred for 2 hrs. Upon the completion of the reaction (IPC by HPLC), the mixture was extracted with EtOAc (3×600 mL) and the combined organic phase was washed with 5% aq. $Na_2CO_3$ (600 mL), 1M HCl (aq. 600 mL) and then brine (600 mL×2). The organic phase was dried over $Na_2SO_4$ (100 g) and then filtered. The filtrate was concentrated under reduced pressure at 45° C. to dryness. The solid obtained was slurried in a mixture of $CH_2Cl_2$ & petroleum ether (1/2, 700 mL) for 1 h. Filtered and the cake was dried under high vacuum at ~55° C. for 4 h. It afforded the title compound A17 as a white solid (148.5 g, 0.193 mol, 98 A % HPLC purity, 85% isolated yield).

$^1$H NMR (400 MHz; DMSO; Me$_4$Si), δ (ppm): 9.23 (1H, s), 8.13 (1H, d, J=8 Hz), 7.35-6.79 (17 H, m), 5.45 (1 H, d, J=24 Hz), 5.06-5.02 (4 H, m), 4.44-4.41 (1 H, m), 3.99-3.95 (1 H, m), 3.56 (3 H,s), 2.93 (2 H,m), 2.66-2.61 (3 H,d, J=20 Hz), 1.35 (9 H,s), 1.12 (3 H,d, J=4 Hz). MS (EI, m/z): 770 (M$^+$).

2-(2-Amino-propionylamino)-3-{6-benzyloxy-5'-[(benzyloxycarbonyl-methyl-amino)-carboxy-methyl]-2'-hydroxy-biphenyl-3-yl}-propionic acid methyl ester (A18)

To a DCM solution (1.95 L, 15 vol) of A17 (130.0 g, 168.8 mmol, 1.0 equiv), was bubbled HCl (gas) at 10~15° C. for 3 hrs. Upon the completion of the reaction (IPC by HPLC), the mixture was concentrated under vacuum at 25° C. for 3 hrs. The solid was dissolved in DCM (600 mL) under stirring. TBME (1200 mL) was the added dropwise into the above solution in a period of ~10 min. The slurry was filtered and the cake was dried under high vacuum at −30-35° C. for 10 h to afford the title compound SSS-A18 (108 g, 0.153 mol, 96.6 A % HPLC purity, 95.5% isolated yield) as a yellow solid.

$^1$H NMR (400 MHz; DMSO; Me$_4$Si), δ (ppm): 13.00 (1 H, brs), 9.67 (1 H,s), 8.95 (1 H, d, J=8 Hz), 8.24 (1 H,s) 7.36-6.97 (16 H, m), 5.76-5.71 (1 H, m), 5.11 (2 H, d, J=4 Hz), 5.03 (2 H, s), 4.46-4.44 (1 H, m), 3.84 (1 H, m), 3.61 (3 H, s), 3.04-3.00 (1 H, m), 2.96-2.90 (1 H, m), 2.59-2.55 (3 H,d, J=16 Hz), 1.36 (3 H,d,J=4 Hz). MS (EI, m/z): 670 (M$^+$).

3-Benzyloxy-14-(benzyloxycarbonyl-methyl-amino)-18-hydroxy-11-methyl-10,13-dioxo-9,12-diaza-tricyclo[13.3.1.12,6]icosa-1(18),2(20),3,5,15(19),16-hexaene-8-carboxylic acid methyl ester (A16)

A solution of PyBOP (11.0 g, 2.12 mol, 1.5 equiv) & NMM (4.3 g, 4.25 mmol, 3.0 equiv.) in DMF (100 mL, 10 vol) was stirred at 40-45° C. The DMF solution (100 mL, 10 vol) of A18 (10.0 g, 1.41 mol, 1.0 equiv) was added dropwise to the above solution at 10-15° C. in a period of 4 hrs. The mixture was stirred at 10-15° C. for 0.5 hrs. The rxn was poured into water (800 mL), the precipitate was filtered. The solid was dissolved in EtOAc (200 mL) and the solution was consecutively washed with 0.1M HCl (100 mL), 5% $NaHCO_3$ (100 mL), 0.1M HCl (100 mL) and brine (100 mL×2). The organic phase was dried over anhydrous $Na_2SO_4$ (~10 g) and filtered. The filtrate was concentrated under reduced pressure at 35-40° C. to afford A16 (10.7 g, 84 A % HPLC purity, 48w % by qNMR, 71% yield) as a yellow solid.

$^1$H NMR(400 MHz; DMSO; Me$_4$Si), δ (ppm): 9.31 (1 H, d, J=4 Hz), 9.09 (1 H, t, J=8 Hz), 8.51-8.41 (1 H, dd, J=22 Hz) 7.44-6.68 (16 H, m), 5.97 (1 H, d, J=4 Hz), 5.16-5.12 (4 H, m), 4.84-4.82 (1 H, m), 4.72-4.77 (1 H, m), 3.37 (3 H, t, J=8 H), 3.31-3.27 (1 H, m), 3.05-2.98 (1 H, m), 2.64-2.60 (3 H, d, J=16 Hz), 1.20-1.15 (3 H, m). MS (EI, m/z): 652 (M$^+$).

Example 5

Preparation of ((tert-butoxycarbonyl)amino)ethoxy)-26-hydroxy-7-methyl-6,9-dioxo-5,8-diaza-1,2(1,3)-dibenzenacyclodecaphane-4-carboxylate (A23) and subsequent compounds Scheme 2E

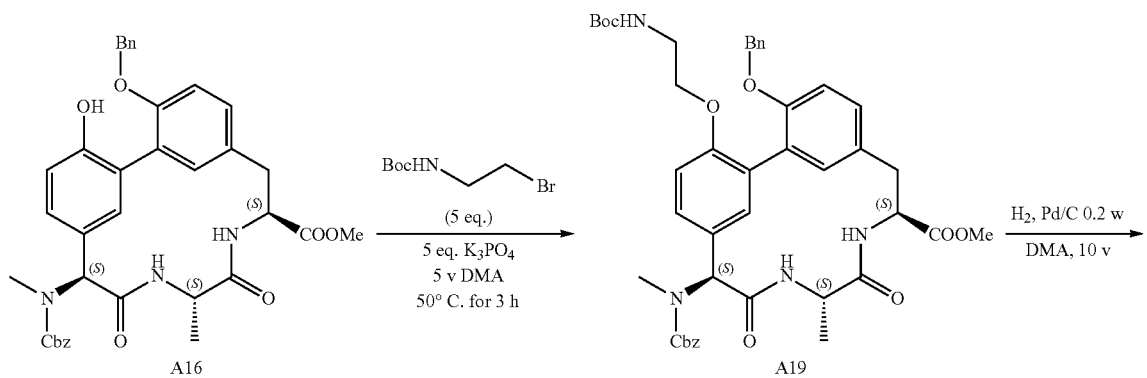

-continued
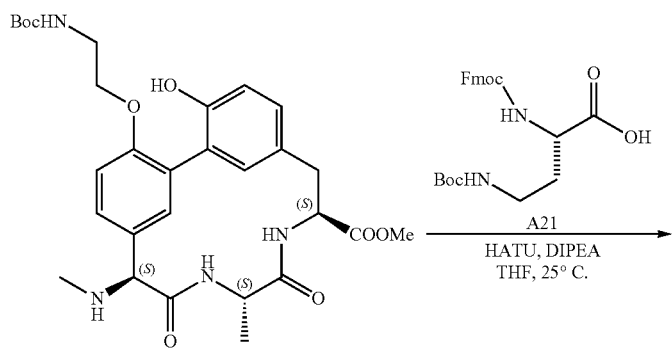
A20
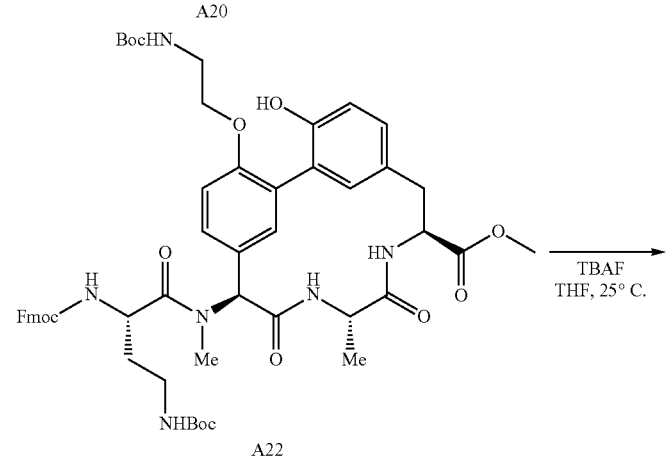
A22
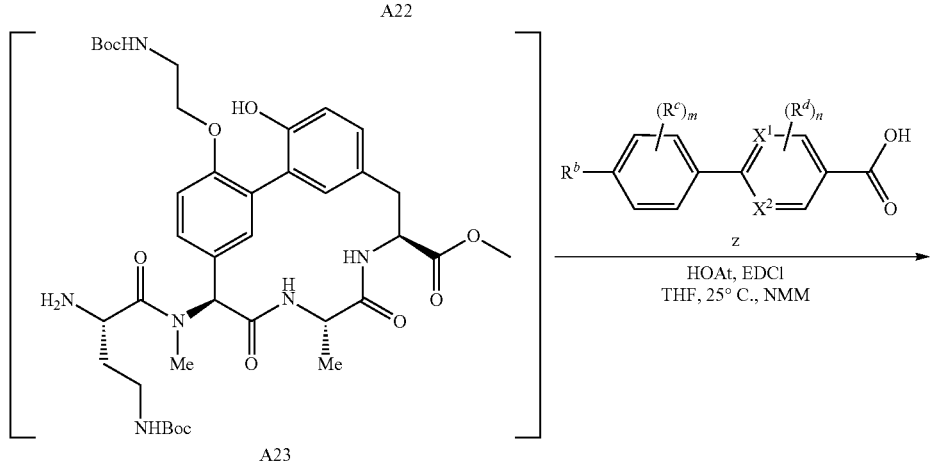
A23
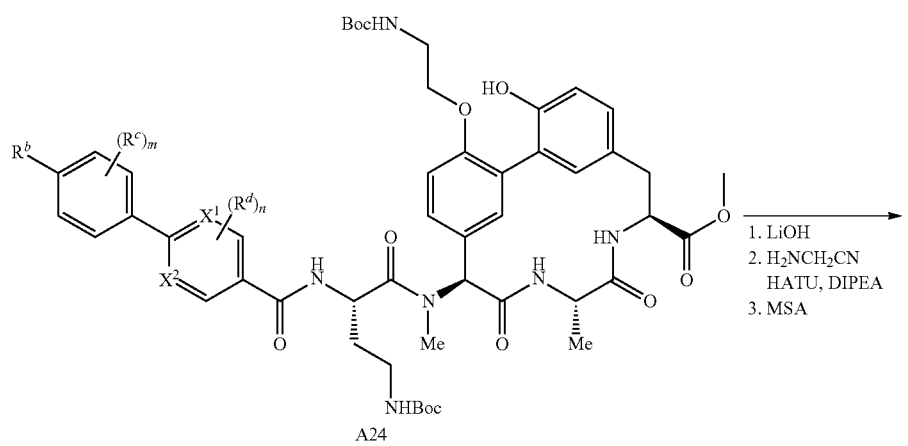
A24

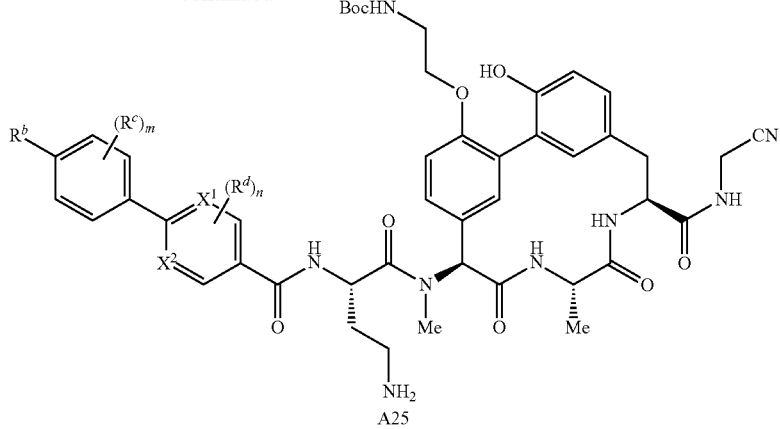

A25

The synthesis of ((tert-butoxycarbonyl)amino)ethoxy)-26-hydroxy-7-methyl-6,9-dioxo-5,8-diaza-1,2(1,3)-dibenzenacyclodecaphane-4-carboxylate (A23) and subsequent compounds is illustrated in Scheme 2D.

Methyl(4S,7S,10S)-26-(benzyloxy)-10-(((benzyloxy)carbonyl)(methyl)amino)-16-(2-((tert-butoxycarbonyl)amino)ethoxy)-7-methyl-6,9-dioxo-5,8-diaza-1,2(1,3)-dibenzenacyclodecaphane-4-carboxylate (A19)

To a rxn vessel, were added the DMA solution (9 L, 6 v related to A16) of the crude A16 (1.5 kg, the assay of A16 was calculated based on the qNMR of A15 and assumed the conversion from A15 to A16 to be 100%), $K_3PO_4$ (2.1 kg, 5.0 equiv.) and 2-bromoethane(Boc)amine (2.2 kg, 5.0 equiv.). The rxn mixture was heated to 50° C. over ~1 h and stirred for additional 3 hrs. or until the reaction completion (0.25 A % of A16 remained on HPLC). After cooling the rxn mixture gradually to ~15° C., the rxn mixture was diluted with EtOAc (45 L, 25 v related to A15) & 30 L of ID water. The phases were separated and the organic phase was washed with 10% brine (9 L×3, standing for ~1 h for each time). The filtrate and wash were combined and dried with 1.5 kg of anhydrous $Na_2SO_4$ for 30 min with stirring. Filtered and the cake was washed with EtOAc (2 L), the combined filtrate was concentrated under vacuum at 45° C. for ~3 h to afford an oil. Slurrying the oil in MeOH/EA/MTBE (3.75 L/1.5 L/3 L) at 10~20° C. for 20 h afforded a white solid. Filtered and the cake was washed with MeOH (200 mL), the wet cake was dried under vacuum at 40-50° C. for 4 h to afford 580 g of A19 with 98.8 A % LC purity in 37% overall yield (uncorrected) over two steps from 1.8 kg of A15 (90.5 w %).

$^1$H NMR (400 MHz, dmso) δ 9.15-8.97 (m, 1H), 8.46 (dd, J=23.5, 9.0 Hz, 1H), 7.21 (dddd, J=70.5, 41.8, 17.2, 8.3 Hz, 14H), 6.74-6.61 (m, 2H), 5.99 (d, J=4.8 Hz, 1H), 5.27-5.07 (m, 4H), 4.87 (s, 1H), 4.77-4.65 (m, 1H), 4.08-3.90 (m, 2H), 3.68 (s, 3H), 3.30 (d, J=21.4 Hz, 1H), 3.19 (s, 2H), 3.06-2.91 (m, 1H), 2.60 (d, J=14.3 Hz, 1H), 1.36 (d, J=17.6 Hz, 9H), 1.16 (dd, J=10.5, 6.9 Hz, 3H).

Methyl(4S,7S,10S)-16-(2-((tert-butoxycarbonyl)amino)ethoxy)-26-hydroxy-7-methyl-10-(methylamino)-6,9-dioxo-5,8-diaza-1,2(1,3)-dibenzenacyclodecaphane-4-carboxylate (A20)

To a flask, were charged DMA (2 L, 10 v), A19 (200 g, >98 A %), 10% Pd/C (40 g, 0.2 w). The vessel containing the rxn mixture was evacuated and backfilled with $H_2$ (5 min× 3). The mixture was stirred under $H_2$ at 50° C. for 16 h or until the rxn completion (97.8 A % of A15 and no A19 remained). The rxn mixture was cooled to ambient temperature and diluted with 4 L of EtOAc. The resulting mixture was washed with brine (2 L×4) and the organic phase was dried with 400 g of anhydrous $Na_2SO_4$ for 10 min. Filtered and the cake was washed with EtOAc (2 L), the combined filtrate was concentrated under vacuum at 45° C. for 3 h to afford 132 g of desired product as light yellowish solid with 98.2 A % LC purity (major impurity 1.2 A % @15.5 min on HPLC). The crudeA20 (98.2 A %) was dissolved in 2 v of i-propanol at ~40° C. to afford a gel-like solution and the solution was continuously stirred for ~1 h at 50° C. to afford a large amount of nice free-flowing white solid. About 16 v of n-heptane was then added dropwise at 30~50° C. in a period of 1.5 h. The resulting suspension was cooled with ice water to <20° C. in a period of ~40 mins. The suspension was filtered and the cake was washed with 200 mL of n-heptane. The wet solid was dried under vacuum at 50° C. for 4 h to afford 115 g of A20 as an off-white solid with 98.4 A % LC purity (major impurity @15.5 min, 0.85 A %) in 80% yield (uncorrected).

$^1$H NMR (400 MHz, dmso) δ 9.01 (d, J=8.8 Hz, 1H), 8.71 (s, 1H), 8.54 (d, J=8.8 Hz, 1H), 7.35 (dd, J=8.5, 1.9 Hz, 1H), 7.02 (dd, J=8.3, 2.2 Hz, 1H), 6.95 (d, J=8.6 Hz, 2H), 6.88 (s, 1H), 6.74 (d, J=8.1 Hz, 2H), 4.78-4.66 (m, 1H), 4.48 (t, J=9.7 Hz, 1H), 4.36 (s, 1H), 3.99 (t, J=6.2 Hz, 2H), 3.70 (s, 3H), 3.22 (q, J=6.0 Hz, 2H), 2.98 (d, J=14.4 Hz, 1H), 2.90-2.74 (m, 1H), 2.29 (s, 3H), 2.12 (s, 1H), 1.36 (s, 9H), 1.22 (d, J=6.8 Hz, 3H).

Methyl (4S,7S,10S)-10-((S)-2-((((9H-fluoren-9-yl)methoxy)carbonyl)amino)-4-((tert-butoxycarbonyl)amino)-N-methylbutanamido)-16-(2-((tert-butoxycarbonyl)amino)ethoxy)-26-hydroxy-7-methyl-6,9-dioxo-5,8-diaza-1,2(1,3)-dibenzenacyclodecaphane-4-carboxylate (A22). To a solution of Fmoc-DAB(Boc)-OH (A21) (16.0 g, 36.3 mmol) and A20 (20.73 g, 36.3 mmol, 1 equiv.) in THF (160 mL, 10 V) was added DIPEA (12.7 mL, 72.6 mmol, 2.00 equiv.), followed by HATU (14.09 g, 36.32 mmol, 1 equiv.) The reaction was stirred at 20° C. for 4 h. To the reaction mixture was added IPAc (80 mL, 5 V) followed by NaHCO₃ (5 wt %, 160 mL, 10 V). After the layers were completely separated. The both layers were separated and analyzed. The organic layer was washed with water (48 mL, 3 V). The organic layer was then concentrated and solvent-switched to THF (3×10 V) at 50° C. and under vacuum at 350 mbar to V$_{tot}$ 100 mL. At 60° C., to the solution was slowly add MeCN (100 mL) and seed was introduced. Additional 100 mL of MeCN was slowly charged. The reaction was then cooled from 60° C. to 50° C. (3 h), then to 40° C. (2 h), and then to 25° C. The solid was collected by filtrated and then washed with MeCN/THF (1:1) (70 mL), and with MeCN 3 times (90 mL+70 mL+60 mL). The white solid was then dried in the oven overnight (40° C., vacuum). 28.1 g of A22 was obtained as a white solid (78% isolated yield).

Methyl (4S,7S,10S)-10-((S)-2-amino-4-((tert-butoxycarbonyl)amino)-N-methylbutanamido)-16-(2-((tert-butoxycarbonyl)amino)ethoxy)-26-hydroxy-7-methyl-6,9-dioxo-5,8-diaza-1,2(1,3)-dibenzenacyclodecaphane-4-carboxylate (A23). To a solution of A22 (27.50 g, 27.70 mmol) in THF (275 mL, 10 V) was added TBAF (1.0 M in THF, 55 mL, 2 equiv.). The reaction was stirred at rt for 4 h. To the reaction mixture was added IPAc (38 mL, 1.4 V) and 10% aq K$_2$HPO$_4$ (192 mL, 7 V) and the layers were separated. The organic layer was treated with 10 wt % aq K$_2$HPO$_4$ (190 mL, 7 V). After the phase cut, the organic layer was then treated with 20 wt % citric acid (275 mL, 10 V), DMA (27.5 mL, 1 V) and heptane (137.5 mL, 5 V) in this order while stirring. After the phase cut, the aqueous layer was then treated with heptane (137.5 mL, 5 V). After the phase cut, to the aqueous layer was added IPAc (275 mL, 10 V) followed by 30% K$_2$CO$_3$ (175 mL, 6.4 V) to pH 9. After the phase cut, aqueous layer was washed 2×150 mL (5 V) of IPAc. The organic layers were combined and washed with 5 V of water. The organic solution of A23 was concentrated to 5 V and taken to the next step without further purification.

Compound A24. To a 40 mL scintillation vial with stir bar was added (1.0 g, 1.297 mmol, 1 equiv) of A23, 1 equiv. of compound z, HOAt (216.2 mg, 1.557 mmol, 1.2 equiv), EDCI (497.4 mg, 2.594 mmol, 2 equiv). THF (10 mL) and NMM (0.296 mL, 2.594 mmol, 2.0 equiv) were added and the mixture was stirred at ambient temperature. After 5 h, the reaction was diluted with water (10 mL), EtOAc (20 mL). The mixture was stirred vigorously and clarified. Separated phases, extracted organic phase with EtOAc (3×15 mL). Washed combined organic phases with 0.5 M aq HCl (2×10 mL). Washed combined organic phases with sat aq NaHCO$_3$ (2×10 mL). Washed combined organic phases with water (10 mL) and brine (10 mL). After concentration, the solid was dissolved in EtOAc (5 mL) and heptane was added dropwise to give a white suspension. Some gummy tan clumps clung together and had to be broke up with spatula, sonicated to give a more uniform suspension and stirred at 400 rpm overnight. The solid was collected through a filtration and dried at rt (vacuum oven) for 24 h. to give A24 as a white solid.

Compound A25 To a 40 mL scintillation vial with stir bar was added A24 (1 equiv), and THF (22 mL). After dissolution, the reaction was cooled to 0° C. To the solution was charged 1 M aq LiOH solution dropwise to control internal temperature <1.5° C. The reaction was monitored by HPLC. After >99% conversion around 1 h, the reaction was quenched with EtOAc (20 mL) and 5% brine. After the phase cut, the organic layer was acidified with 1 M aqu HCl (6.4 mL) to pH 3-4. After the phase cut, the aqueous layer was washed with EtOAc (2×25 mL). The organic phase was combined and concentrated under reduced pressure. The resulting crude carboxylate (not shown in Scheme 2E) was loaded into a 100 ml easy max reactor followed by dry MeTHF (40 ml (8 vol) and the mixture was allowed to stir at 25° C. until obtaining a clear solution. HATU (1.1 equiv.) was then added to the mixture and the slurry was stirred at 25° C. for 60 minutes. A separate solution of aminoacetonitrile was prepared by dissolving aminoacetonitrile HCl (1.1 equiv.) in DMF (5.0 ml 1 vol) followed by the addition of DIPEA (2.2 equiv.) and stirring for 30 minutes at 25° C. The aminoacetonitrile DMF solution was then added to the easy max reactor at 25° C. and the resulting mixture was allowed to stir for 60 minutes until completion. To the completed reaction was added a 2.5% NaHCO$_3$ solution in H$_2$O (5 vol) followed by MeTHF (5 vol). The resulting mixture was separated and the organics were washed with H$_2$O (5 vol) twice. The resulting organic solution was filtered through a celite pad and concentrated to dryness. The crude product was dissolved in DMF (50 ml, 10 vol) and heated to 70° C. H$_2$O (30 ml, 6 vol) was added and mixture was allowed to stir for 15 minutes and cooled to 20° C. over 14 h. The resulting slurry was filtered and washed with H$_2$O (2 vol) followed by heptane (2 vol) then dried in vacuo at 40° C. for 16 h to give the glycine nitrile warhead compound as a white solid, which was dissolved in THF and stirred at 25° C. until fully dissolved. To this mixture was added methanesulfonic acid (6.2 uL, 2 equiv.) and the resulting mixture was heated to 60° C. and stirred for 20 h. White solid precipitated and was collected by filtration to give A25.

Compounds of formula A25 prepared by the above methods are shown below in Table 1 together with $^1$H NMR data.

TABLE 1

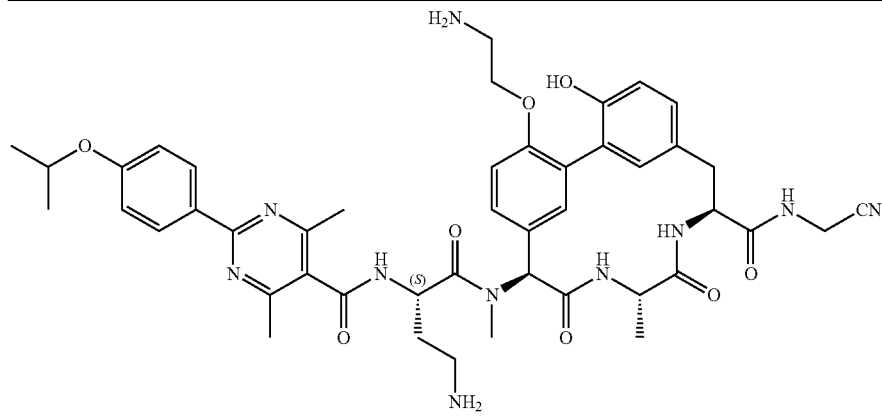

$^1$H NMR (400 MHz, MeOH-d4) δ 8.49 (brs, 1H), 8.19 (d, J = 8.0 Hz, 2H), 7.23 (d, J = 8.0 Hz, 2H), 6.99-6.83 (m, 5H), 6.62 (s, 1H), 6.51 (s, 1H), 5.34-5.24 (m, 1H), 4.82-4.68 (m, 2H), 4.50-4.35 (m, 3H), 4.25 (s, 2H), 3.42 (s, 2H), 3.14 (t, J = 7.2 Hz, 2H), 3.01 (s, 3H), 2.95-2.80 (m, 2H), 2.44 (s, 6H), 2.33-2.25 (m, 1H), 2.22-2.09 (m, 1H), 1.38-1.33 (m, 9H).

TABLE 1-continued
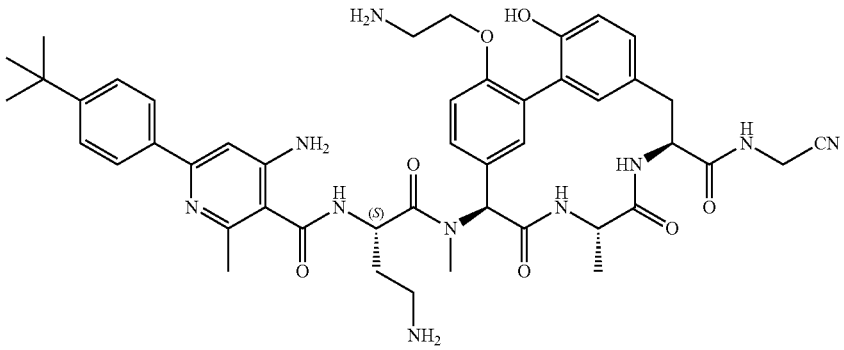
¹H NMR (400 MHz, MeOH-d4) δ 8.48 (brs, 1H), 7.73 (d, J = 8.0 Hz, 2H), 7.65 (d, J = 8.0 Hz, 2H), 7.35 (d, J = 7.2 Hz, 1H), 7.18-7.09 (m, 2H), 7.03 (s, 1H), 6.97 (s, 1H), 6.91 (d, J = 8.4 Hz, 1H), 6.80 (s, 1H), 6.47 (s, 1H), 5.12-5.09 (m, 1H), 4.85-4.70 (m, 2H), 4.43-4.33 (m, 2H), 4.21 (s, 2H), 3.62-3.43 (m, 2H), 3.26-3.09 (m, 4H), 3.00 (s, 3H), 2.61 (s, 3H), 2.29-2.19 (m, 2H), 1.45 (s, 9H), 1.43 (d, J = 7.2 Hz, 3H)
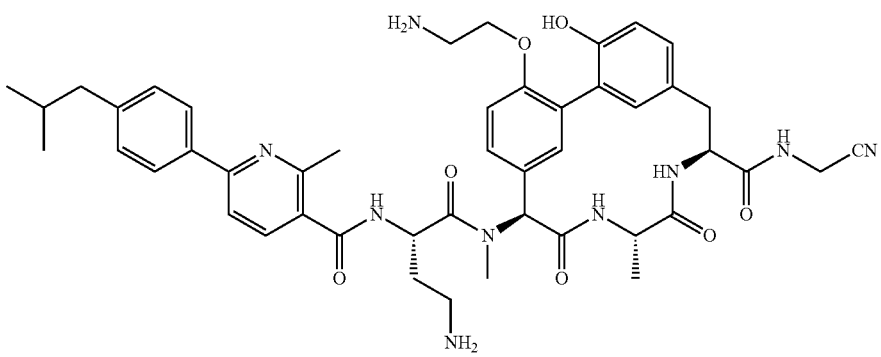 [SMILES: Cc1nc(-c2ccc(CC(C)C)cc2)ccc1C(=O)N[C@@H](CCN)C(=O)N(C)[C@@H]1C(=O)N[C@@H](C)C(=O)N[C@H](C(=O)NCC#N)Cc2ccc(O)c(c2)-c2cc1ccc2OCCN]
¹H NMR (400 MHz, MeOH-d4) δ 8.51 (brs, 2H), 7.90-7.60 (m, 4H), 7.31-7.24 (m, 3H), 7.15 (d, J = 8.0 Hz, 1H), 7.10 (d, J = 8.0 Hz, 1H), 6.90-6.80 (m, 2H), 6.70-6.45 (m, 2H), 5.19-5.16 (m, 1H), 4.82-4.59 (m, 2H), 4.40-4.28 (m, 2H), 4.20 (s, 2H), 3.36-3.32 (m, 1H) 3.27-3.24 (m, 1H), 3.15-2.96 (m, 7H), 2.65 (s, 3H), 2.55 (d, J = 8.0 Hz, 2H), 2.33-2.24 (m, 1H), 2.21-2.14 (m, 1H), 1.95-1.87 (m, 1H), 1.35 (d, J = 6.8 Hz, 3H), 0.94 (d, J = 6.8 Hz, 6H)
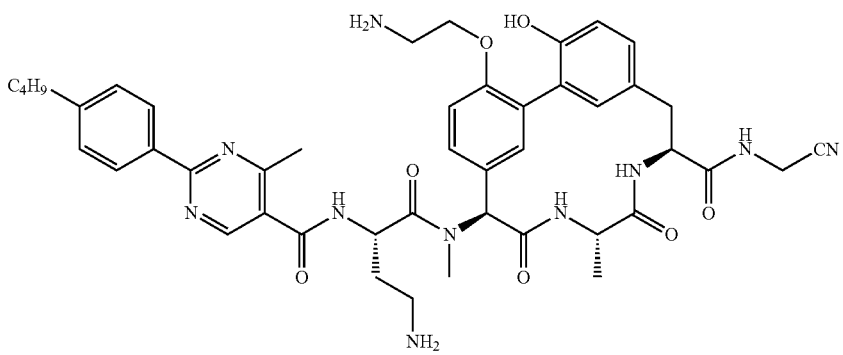
¹H NMR (400 MHz, MeOH-d4) δ 8.77 (s, 1H), 8.53 (brs, 2H), 8.25 (d, J = 7.5 Hz, 2H), 7.33-7.27 (m, 3H), 7.14 (d, J = 8.0 Hz, 1H), 7.00 (d, J = 8.0 Hz, 1H), 6.91-6.83 (m, 2H), 6.59 (s, 1H), 6.54 (s, 1H), 5.21-5.15 (m, 1H), 4.83-4.80 (m, 1H), 4.74-4.69 (m, 1H), 4.39-4.29 (m, 2H), 4.22 (s, 2H), 3.29-2.99 (m, 6H), 2.96 (s, 3H), 2.71 (t, J = 7.6 Hz, 2H), 2.64 (s, 3H), 2.35-2.25 (m, 1H), 2.22-2.14 (m, 1H), 1.73-1.61 (m, 2H), 1.46-1.32 (m, 5H), 0.98 (t, J = 7.4 Hz, 3H).

TABLE 1-continued
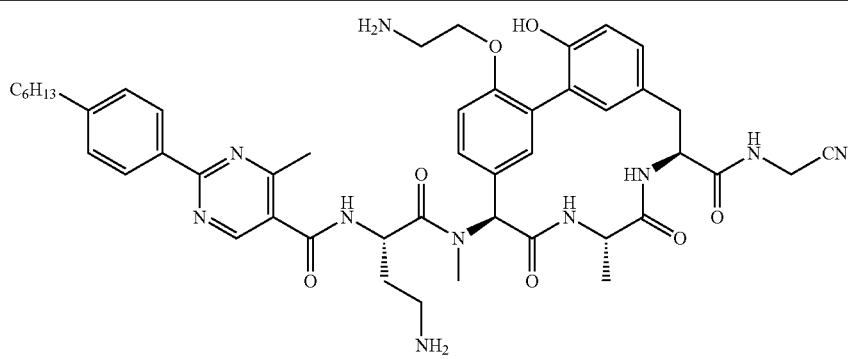
¹H NMR (400 MHz, MeOH-d4) δ 8.77 (s, 1H), 8.53 (brs, 1H), 8.27 (d, J = 8.0 Hz, 2H), 7.35-7.26 (m, 3H), 7.14 (d, J = 8.8 Hz, 1H), 7.04-6.97 (m, 1H), 6.93-6.87 (m, 1H), 6.84 (d, J = 8.4 Hz, 1H), 6.62 (s, 1H), 6.52 (s, 1H), 5.22-5.15 (m, 1H), 4.84-4.69 (m, 2H), 4.37-4.25 (m, 2H), 4.22 (s, 2H), 3.50-2.93 (m, 8H), 2.70 (t, J = 7.6 Hz, 2H), 2.40 (s, 3H), 2.33-2.18 (m, 1H), 2.18-2.05 (m, 1H), 1.74-1.62 (m, 2H), 1.40-1.35 (m, 9H), 0.93 (t, J = 6.8 Hz, 3H).
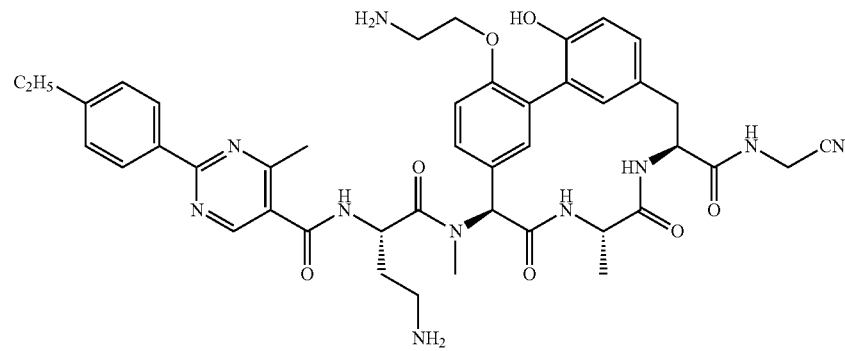
¹H NMR (400 MHz, MeOH-d4) δ 8.76 (s, 1H), 8.23 (d, J = 8.0 Hz, 2H), 7.36-7.25 (m, 3H), 7.13 (d, J = 8.8 Hz, 1H), 6.90-6.89 (m, 2H), 6.79 (d, J = 7.2 Hz, 1H), 6.65 (s, 1H), 6.51 (s, 1H), 5.15-5.12 (m, 1H), 4.81-4.79 (m, 1H), 4.67-4.59 (m, 1H), 4.24 (s, 2H), 4.20-4.05 (m, 2H), 3.10-2.80 (m, 6H), 3.00 (s, 3H), 2.73 (q, J = 7.2 Hz, 2H), 2.60 (s, 3H), 2.15-2.00 (m, 1H), 2.00-1.85 (m, 1H), 1.35 (d, J = 7.2 Hz, 3H), 1.28 (t, J = 7.2 Hz, 3H).
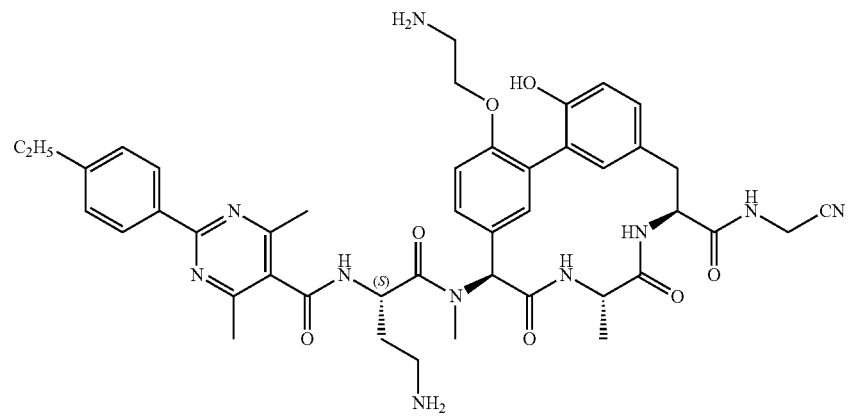
¹H NMR (400 MHz, MeOH-d4) δ 8.48 (brs, 2H), 8.21 (d, J = 7.2 Hz, 2H), 7.29 (d, J = 7.6 Hz, 2H), 7.20 (brs, 2H), 7.00-6.82 (m, 3H), 6.58 (brs, 2H), 5.32-5.27 (m, 1H), 4.85-4.75 (m, 2H), 4.50-4.40 (m, 2H), 4.24 (s, 2H), 3.50-3.30 (m, 2H), 3.20-3.05 (m, 2H), 3.00-2.85 (m, 5H), 2.70 (q, J = 7.6 Hz, 2H), 2.48 (s, 6H), 2.35-2.20 (m, 1H), 2.20-2.05 (m, 1H), 1.35 (d, J = 6.4 Hz, 3H), 1.29 (t, J = 7.2 Hz, 3H).

TABLE 1-continued
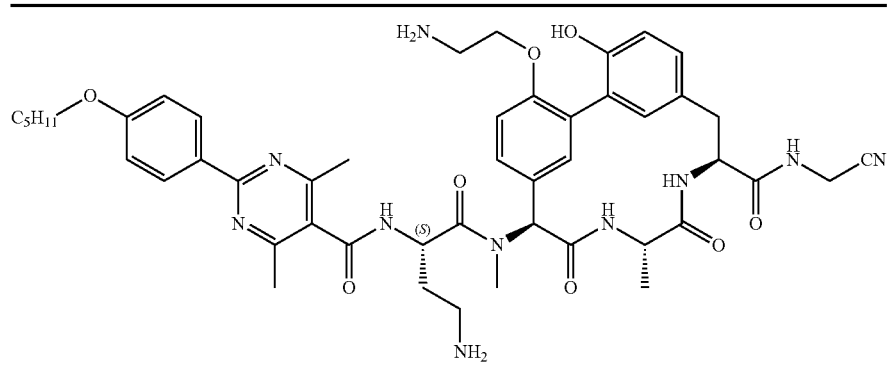
$^1$H NMR (400 MHz, MeOH-d4) δ 8.13 (d, J = 8.0 Hz, 2H), 7.26 (s, 2H), 6.94-6.86 (m, 5H), 6.73 (s, 1H), 6.37 (s, 1H), 5.38-5.34 (m, 1H), 4.83-4.78 (m, 1H), 4.56-4.53 (m, 1H), 4.47-4.43 (m, 1H), 4.29-4.21 (m, 3H), 4.08 (t, J = 6.4 Hz, 2H), 3.50-3.35 (m, 2H), 3.20-3.05 (m, 2H), 3.02 (s, 3H), 2.95-2.88 (m, 1H), 2.80-2.60 (m, 1H), 2.33 (s, 6H), 2.33-2.20 (m, 1H), 2.20-2.10 (m, 1H), 1.89-1.82 (m, 2H), 1.50-1.40 (m, 4H), 1.36 (d, J = 6.8 Hz, 3H), 1.01 (t, J = 7.2 Hz, 3H).
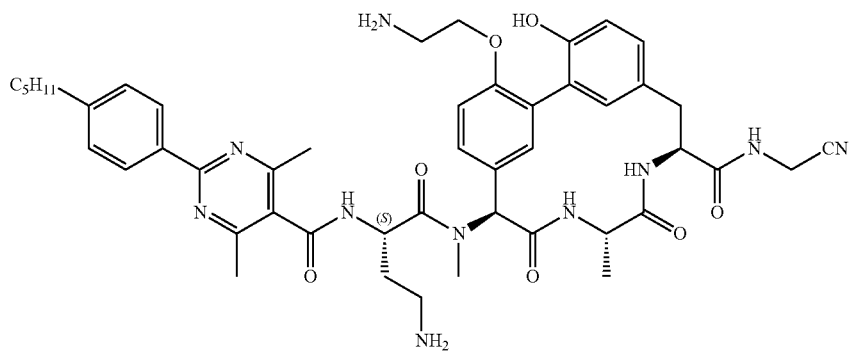
$^1$H NMR (400 MHz, MeOH-d4) δ 8.52 (brs, 1H), 8.23 (d, J = 8.0 Hz, 2H), 7.32-7.26 (m, 3H), 7.21 (d, J = 8.0 Hz, 1H), 6.98 (brs, 1H), 6.92-6.85 (m, 3H), 6.59 (brs, 2H), 5.30-5.28 (m, 1H), 4.84-4.82 (m, 2H), 4.46-4.39 (m, 2H), 4.25 (s, 2H), 3.42-3.37 (m, 2H), 3.16 (t, J = 8.0 Hz, 2H), 3.05-2.95 (m, 2H), 3.02 (s, 3H), 2.71 (t, J = 8.0 Hz, 2H), 2.51 (s, 6H), 2.34-2.20 (m, 1H), 2.20-2.05 (m, 1H), 1.70 (t, J = 6.8 Hz, 2H), 1.50-1.35 (m, 7H), 0.96 (t, J = 6.4 Hz, 3H).
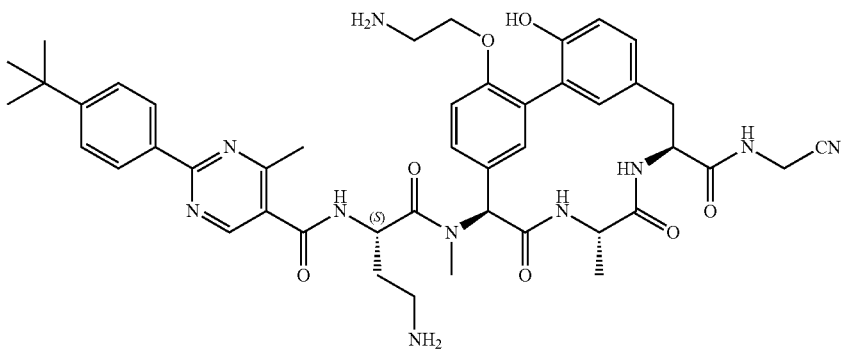
$^1$H NMR (400 MHz, MeOH-d4) δ 8.76 (s, 1H), 8.51 (brs, 1H), 8.19 (d, J = 8.4 Hz, 2H), 7.49 (d, J = 8.4 Hz, 2H), 7.27 (d, J = 8.4 Hz, 1H), 7.16 (d, J = 8.4 Hz, 1H), 6.93-6.87 (m, 1H), 6.85-6.82 (m, 2H), 6.64 (s, 1H), 6.44 (s, 1H), 5.20-5.17 (m, 1H), 4.81-4.78 (m, 1H), 4.65-4.59 (m, 1H), 4.44-4.32 (m, 2H), 4.24 (s, 2H), 3.41-3.30 (m, 2H), 3.16 (t, J = 7.6 Hz, 2H), 3.00-2.90 (m, 2H), 2.96 (s, 3H), 2.591 (s, 3H), 2.33-2.13 (m, 2H), 1.38 (s, 9H), 1.35 (d, J = 6.8 Hz, 3H).

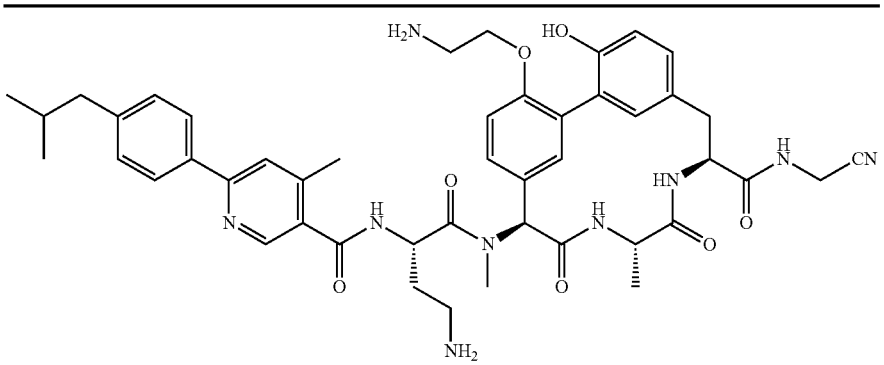
¹H NMR (400 MHz, MeOH-d4) δ 8.62 (s, 1H), 8.50 (brs, 1H), 7.69 (d, J = 8.0 Hz, 2H), 7.60 (s, 1H), 7.30-7.17 (m, 4H), 6.89-6.82 (m, 3H), 6.70 (s, 1H), 6.31 (s, 1H), 5.21-5.18 (m, 1H), 4.81-4.76 (m, 2H), 4.48-4.35 (m, 2H), 4.26 (s, 2H), 3.45-3.38 (m, 2H), 3.23-3.15 (m, 2H), 3.05-2.84 (m, 2H), 2.98 (s, 3H), 2.55 (d, J = 7.2 Hz, 2H), 2.35 (brs, 2H), 2.29-2.19 (m, 2H), 1.96-1.89 (m, 1H), 1.35 (d, J = 6.8 Hz, 3H), 0.95 (d, J = 6.8 Hz, 6H).
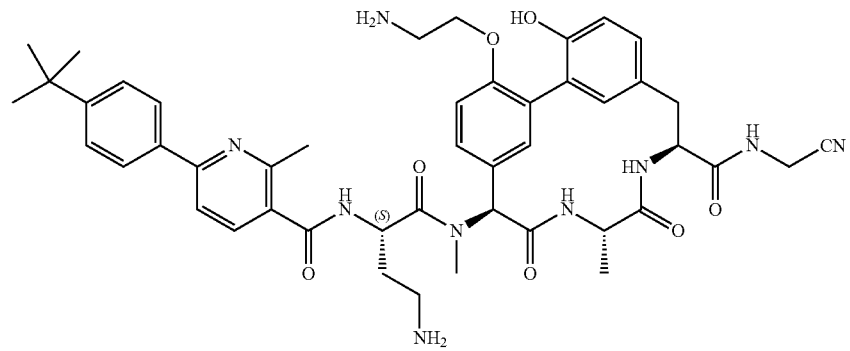
¹H NMR (400 MHz, MeOH-d4) δ 8.52 (s, 1H), 7.82 (d, J = 7.6 Hz, 2H), 7.72 (d, J = 8.0 Hz, 1H), 7.64 (d, J = 8.0 Hz, 1H), 7.50 (d, J = 8.4 Hz, 2H), 7.33-7.27 (m, 1H), 7.17 (d, J = 8.4 Hz, 1H), 7.00 (d, J = 8.0 Hz, 1H), 6.91-6.85 (m, 2H), 6.57 (brs, 2H), 5.21-5.17 (m, 1H), 4.85-4.80 (m, 1H), 4.63-4.59 (m, 1H), 4.41-4.32 (m, 2H), 4.21 (s, 2H), 3.28-3.00 (m, 6H), 2.97 (s, 3H), 2.66 (s, 3H), 2.32-2.25 (m, 1H), 2.21-2.14 (m, 1H), 1.42 (s, 9H), 1.36 (m, 12H).
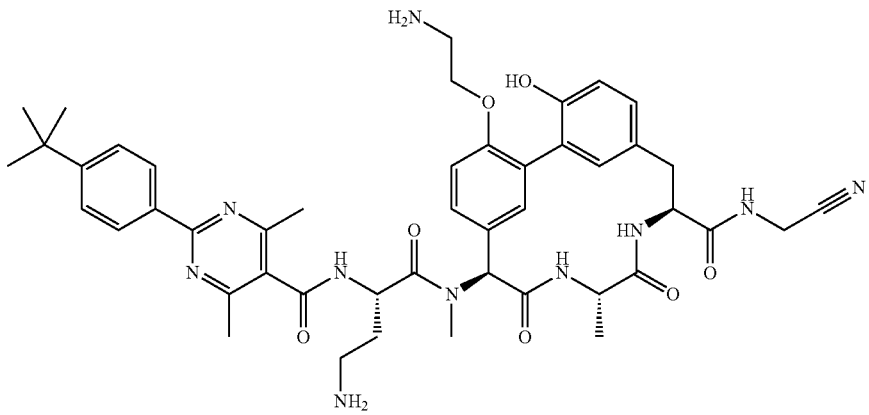 [SMILES: Cc1nc(-c2ccc(C(C)(C)C)cc2)nc(C)c1C(=O)N[C@@H](CCN)C(=O)N(C)[C@@H]1C(=O)N[C@@H](C)C(=O)N[C@H](C(=O)NCC#N)Cc2ccc(O)c(c2)-c2cc1ccc2OCCN]
¹H NMR (500 MHz, DMSO-d6) δ 9.17 (d, J = 7.3 Hz, 1H), 8.98 (d, J = 7.7 Hz, 1H), 8.71 (t, J = 5.5 Hz, 1H), 8.44 (d, J = 9.0 Hz, 1H), 8.36-8.29 (m, 2H), 7.59-7.52 (m, 2H), 7.19-7.04 (m, 3H), 6.90-6.80 (m, 2H), 6.71 (s, 1H), 6.42 (s, 1H), 5.09-5.01 (m, 1H), 4.80-4.66 (m, 2H), 4.29-4.15 (m, 4H), 3.19-3.09 (m, 3H), 3.02-2.88 (m, 6H), 2.50 (s, 6H), 2.14-2.03 (m, 1H), 2.02-1.91 (m, 1H), 1.35 (s, 9H), 1.21 (d, J = 6.6 Hz, 3H).

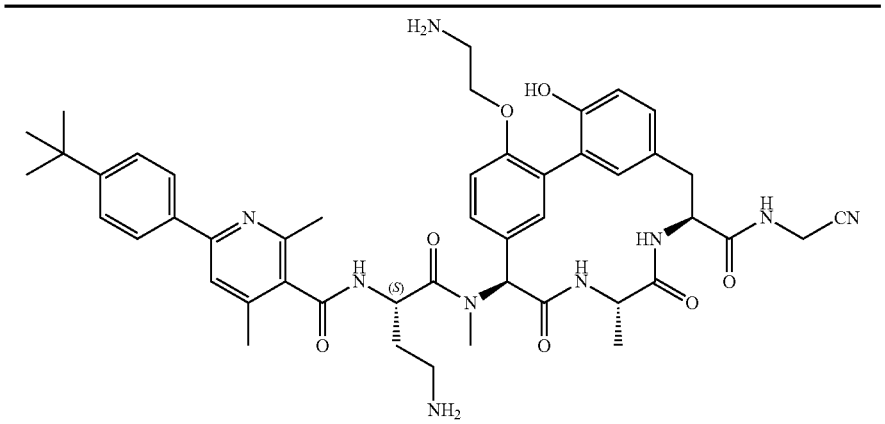

¹H NMR (400MHz, MeOH-d4) δ 8.47 (brs, 3H), 7.67 (brs, 2H), 7.54 (d, J = 7.6 Hz, 2H), 7.38 (brs, 1H), 7.24 (s, 2H), 7.00-6.75 (m, 3H), 6.89 (s, 1H), 6.36 (brs, 1H), 5.38-5.30 (m, 1H), 4.85-4.75 (m, 1H), 4.60-4.47 (m, 1H), 4.45-4.35 (m, 1H), 4.30-4.20 (m, 1H), 4.24 (s, 2H), 3.50-3.40 (m, 2H), 3.20-3.10 (m, 2H), 3.01 (s, 3H), 2.90-2.80 (m, 1H), 2.54 (s, 3H), 2.40-2.00 (m, 6H), 1.42 (s, 9H), 1.34 (d, J = 6.8 Hz, 3H).

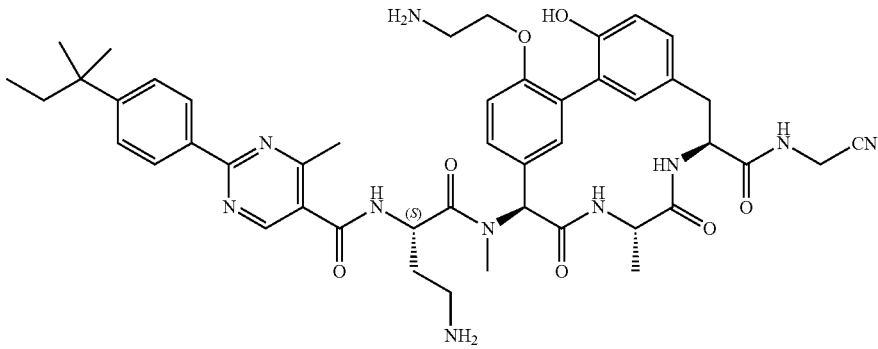

¹H NMR (400 MHz, MeOH-d4) δ 8.77 (s, 1H), 8.51 (brs, 1H), 8.27 (d, J = 8.4 Hz, 2H), 7.47 (d, J = 8.0 Hz, 2H), 7.32-7.26 (m, 1H), 7.16 (d, J = 8.4 Hz, 1H), 7.02-6.96 (m, 1H), 6.88 (brs, 1H), 6.85 (d, J = 8.4 Hz, 1H), 6.56 (brs, 2H), 5.21-5.16 (m, 1H), 4.82-4.78 (m, 1H), 4.73-4.67 (m, 1H), 4.43-4.31 (m, 2H), 4.23 (s, 2H), 3.42-3.33 (m, 2H), 3.15 (t, J = 7.6 Hz, 2H), 3.10-3.00 (m, 2H), 2.96 (s, 3H), 2.64 (s, 3H), 2.35-2.20 (m, 1H), 2.20-2.05 (m, 1H), 1.74 (q, J = 7.2 Hz, 2H), 1.36 (d, J = 6.8 Hz, 3H), 1.35 (s, 6H), 0.93 (t, J = 7.2 Hz, 3H).

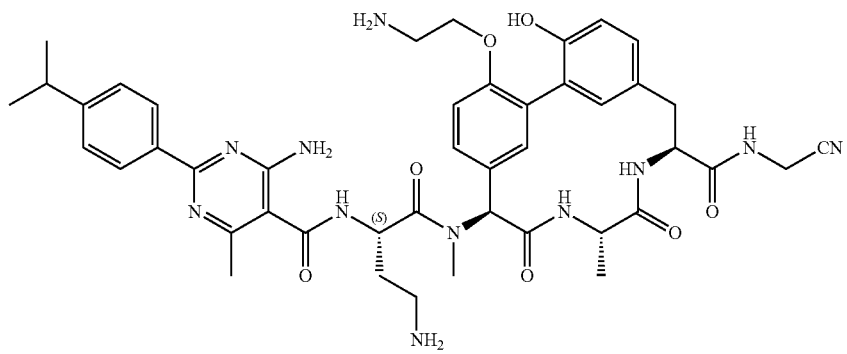

¹H NMR (400 MHz, MeOH-d4) δ 8.17 (d, J = 8.4 Hz, 1H), 8.04 (d, J = 8.4 Hz, 1H), 7.54-7.42 (m, 2H), 7.34-7.24 (m, 1H), 7.24-7.00 (m, 2H), 6.95-6.83 (m, 2H), 6.65 (s, 1H), 6.56 (brs, 1H), 5.18-5.06 (m, 1H), 4.83-4.73 (m, 2H), 4.53-4.32 (m, 2H), 4.24 (s, 2H), 3.45-3.33 (m, 2H), 3.22-3.11 (m, 2H), 3.07-2.87 (m, 1H), 3.00 (s, 3H), 2.86-2.67 (m, 1H), 2.46 (s, 3H), 2.32-2.05 (m, 2H), 1.44 (s, 9H), 1.36 (d, J = 6.8 Hz, 3H).

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

What is claimed is:

1. A method for making an arylomycin ring of formula o

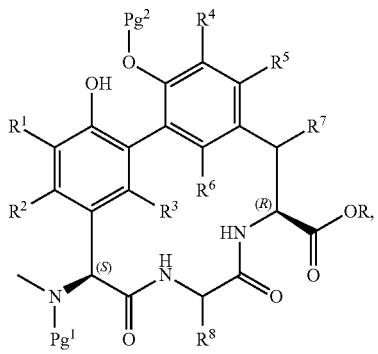

wherein:

Y is halogen;

R is: hydrogen; or $C_{1-4}$alkyl; and may be the same or different on each occurrence;

$R^1, R^2, R^3, R^4, R^5$ and $R^6$ each independently is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; cyano-$C_{1-6}$alkyl; or nitro, wherein the amino and hydroxyl moieties may optionally include a protecting group;

$R^7$ is: hydrogen; or $C_{1-4}$alkyl;

$R^8$ is: hydrogen; $C_{1-4}$alkyl; halo-$C_{1-4}$alkyl; halo; amino; amino-$C_{1-4}$alkyl; hydroxy; hydroxy-$C_{1-6}$alkyl; cyano; or cyano-$C_{1-6}$alkyl, wherein the amino and hydroxyl moieties may optionally include a protecting group;

$R^a$ is: hydrogen; or $C_{1-4}$alkyl; and may be the same or different on each occurrence, or two R groups may form a $C_{2-6}$alkylene that, together with the atoms to which they are attached, may form a five- or six-membered ring;

$Pg^1$ is an optional amine protecting group and may be the same or different on each occurrence; and $Pg^2$ is an optional hydroxyl protecting group and may be the same or different on each occurrence;

the method comprising:

reacting a phenyl boronate compound of formula m:

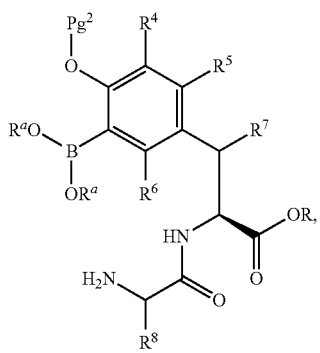

or a salt or solvate thereof, with a phenyl halide compound of formula e;

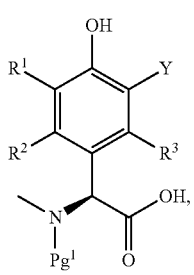

or a salt or solvate thereof, to form a compound of formula n;

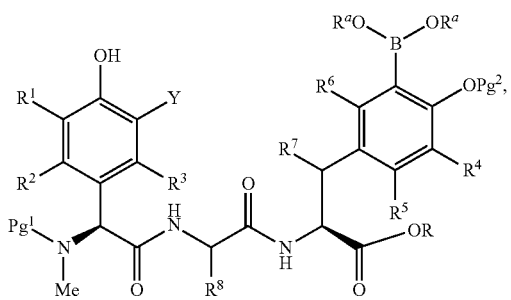

or a salt or solvate thereof; and treating the compound of formula n with chloro(crotyl)(tri-tert-butylphosphine)palladium(II), to make the compound of formula o; or a salt or solvate thereof.

2. The method of claim 1, further comprising:

reacting a compound of formula k:

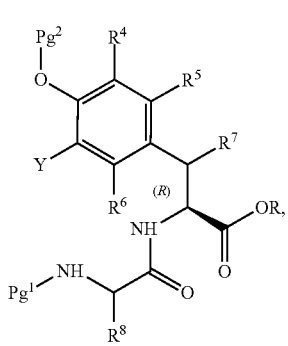

or a salt or solvate thereof, with a boronating agent to form a compound of formula 1:

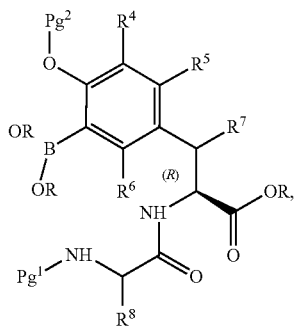

or a salt or solvate thereof; and
removing the protecting group Pg' from compound 1 to form the compound of formula m;
or a salt or solvate thereof.

3. The method of claim 2, further comprising:
reacting a compound of formula h:

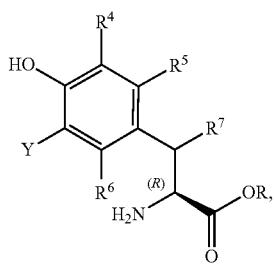

or a salt or solvate thereof,
with an amino acid of formula i:

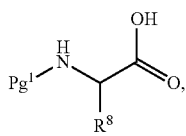

or a salt or solvate thereof,
to forma compound of formula j:

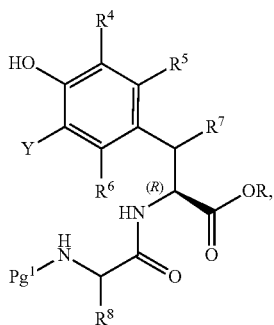

or a salt or solvate thereof; and
introducing a hydroxyl protecting group $Pg^2$ to compound j to form the compound of formula k;
or a salt or solvate thereof.

4. The method of claim 3, further comprising:
esterifying a compound of formula g:

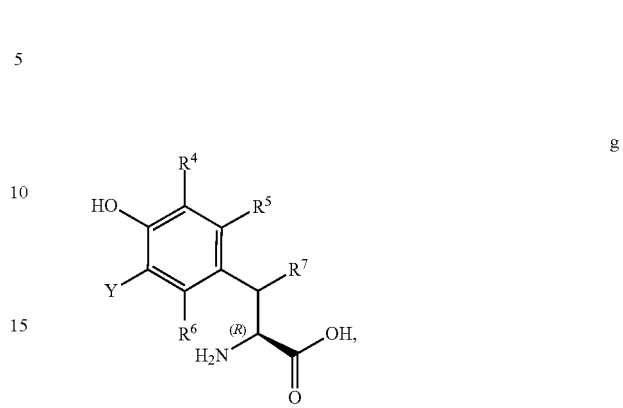

or a salt or solvate thereof,
to form the compound of formula h;
or a salt or solvate thereof.

5. The method of claim 4, further comprising:
halogenating of a compound formula f:

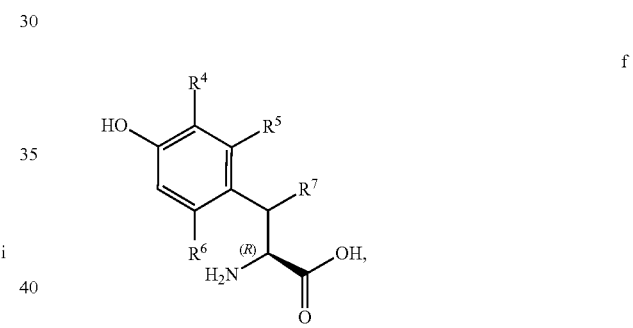

or a salt or solvate thereof,
to form the compound of formula g;
or a salt or solvate thereof.

6. The method of claim 1, further comprising:
reducing a compound of formula d:

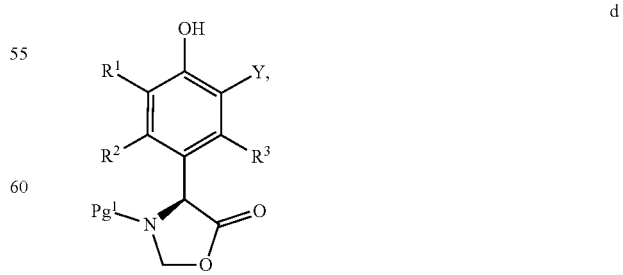

to form the compound of formula e;
or a salt or solvate thereof.

7. The method of claim 6, further comprising:
reacting a compound of formula c:

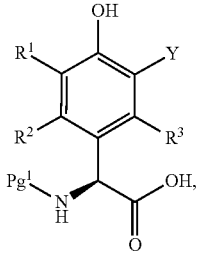

or a salt or solvate thereof,
with trioxane, to form the compound of formula d;
or a salt or solvate thereof.

8. The method of claim 7, further comprising:
halogenating a compound of formula a:

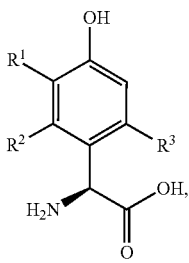

or a salt or solvate thereof,
to form a compound of formula b:

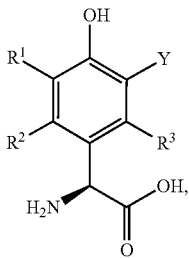

or a salt or solvate thereof; and
introducing an amine protecting group to compound b to form the compound of formula c;
or a salt or solvate thereof.

9. The method of claim 1, further comprising:
reacting the compound of formula o, or a salt or solvate thereof;
with an alkylating reagent of formula p:

$$R^9-X_p,$$

or a salt or solvate thereof, to form a compound of formula q:

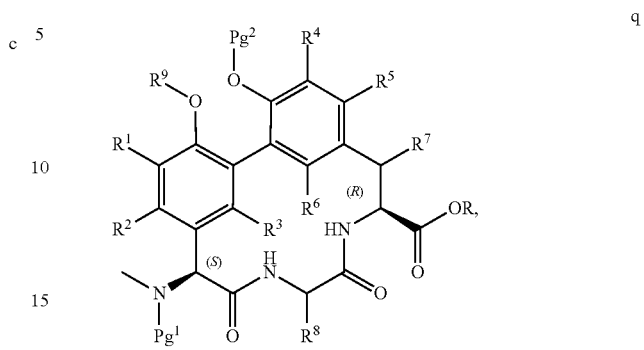

or a salt or solvate thereof;
wherein:
X is a leaving group; and
$R^9$ is: $C_{1-4}$alkyl; halo-$C_{1-4}$alky; hydroxyl-$C_{1-4}$alkyl; amino-$C_{1-4}$alkyl, aminosulfonyl-$C_{1-4}$alkyl; or $C_{1-4}$alkoxy-$C_{1-4}$alkyl, wherein the amino and hydroxyl moieties each may optionally include a protecting group.

10. The method of claim 9, further comprising:
removing the amine protecting group $Pg_1$, and optionally removing the hydroxyl protecting group $Pg^2$ from the compound of formula q, or a salt or solvate thereof, to form a compound of formula r:

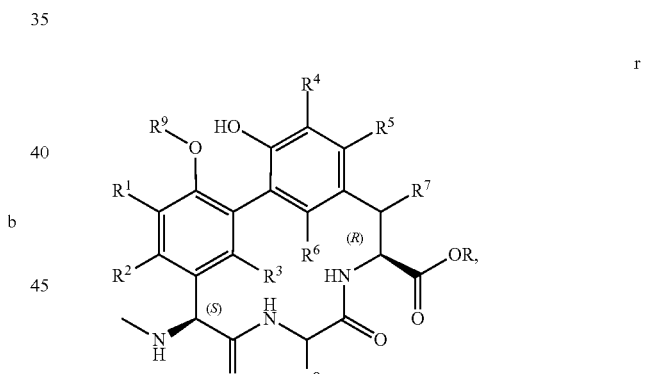

or a salt or solvate thereof.

11. The method of claim 10, further comprising:
reacting the compound of formula r, or a salt or solvate thereof;
with an amino acid reagent of formula s:

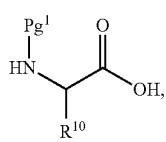

or a salt or solvate thereof;

to form a compound of formula t:
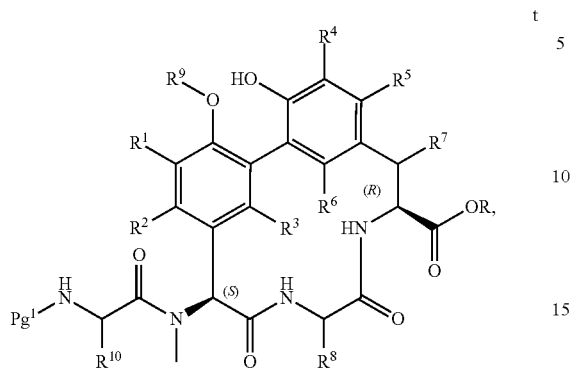
or a salt or solvate thereof.
* * * * *

UNITED STATES PATENT AND TRADEMARK OFFICE
CERTIFICATE OF CORRECTION

PATENT NO. : 11,192,924 B2
APPLICATION NO. : 16/581116
DATED : December 7, 2021
INVENTOR(S) : Filip Petronijevic et al.

It is certified that error appears in the above-identified patent and that said Letters Patent is hereby corrected as shown below:

On the Title Page

In Column 2, item (57), under Abstract, Line 3, delete "$R^9$, $R^5$, $R^{10}$" and insert -- $R^9$, $R^{10}$ --, therefor.

In the Claims

In Column 69, Claim 1, Line 26, delete "$R^4$ ,$R^5$" and insert -- $R^4$ , $R^5$ --, therefor.

In Column 69, Claim 1, Line 37, delete "two R groups" and insert -- two $R^a$ groups --, therefor.

In Column 71, Claim 2, Line 1, delete "formula 1" and insert -- formula I --, therefor.

In Column 71, Claim 2, Lines 4-15, delete " 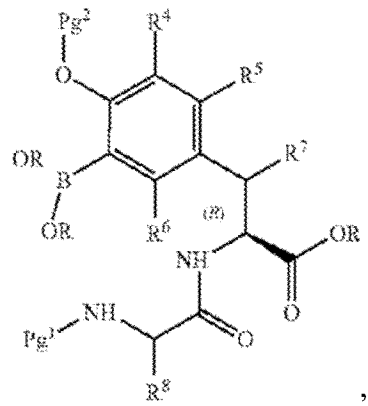 " and insert

Signed and Sealed this
Second Day of April, 2024

Katherine Kelly Vidal
*Director of the United States Patent and Trademark Office*

CERTIFICATE OF CORRECTION (continued)
U.S. Pat. No. 11,192,924 B2

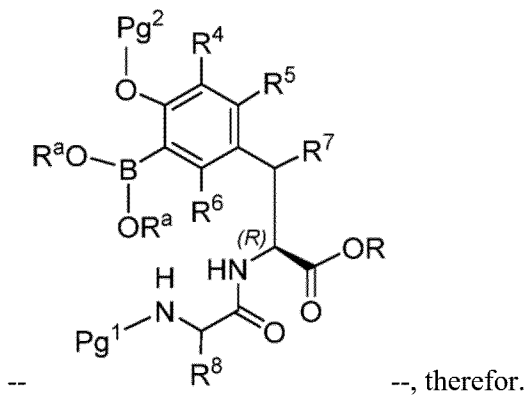

-- , therefor.

In Column 71, Claim 2, Line 18, delete "Pg'" and insert -- $Pg^1$ --, therefor.

In Column 71, Claim 2, Line 18, delete "compound 1" and insert -- compound I --, therefor.

In Column 71, Claim 2, Line 46, delete "forma" and insert -- form a --, therefor.

In Column 71, Claim 2, Line 46, delete "formula i" and insert -- formula j --, therefor.

In Column 73, Claim 9, Line 65, delete "$R^9$-$X_p$," and insert -- $R^9$-X $_p$, --, therefor.

In Column 74, Claim 9, Line 24, delete "halo-$C_{1-4}$alky;" and insert -- halo-$C_{1-4}$alkyl; --, therefor.

In Column 74, Claim 10, Line 30, delete "$Pg_1$" and insert -- $Pg^1$ --, therefor.